(12) United States Patent
David

(10) Patent No.: US 9,839,591 B2
(45) Date of Patent: Dec. 12, 2017

(54) ANIONIC DYE OR BRIGHTENER BEARING AN AMMONIUM OR PHOSPHONIUM COUNTERION, DYE COMPOSITION COMPRISING THEM AND PROCESS FOR DYEING KERATIN FIBRES USING THESE DYES

(71) Applicant: L'OREAL, Paris (FR)

(72) Inventor: Herve David, La Varenne Saint Hilarie (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/403,360

(22) PCT Filed: May 24, 2013

(86) PCT No.: PCT/EP2013/060792
§ 371 (c)(1),
(2) Date: Nov. 24, 2014

(87) PCT Pub. No.: WO2013/175002
PCT Pub. Date: Nov. 28, 2013

(65) Prior Publication Data
US 2015/0113742 A1 Apr. 30, 2015

Related U.S. Application Data

(60) Provisional application No. 61/666,782, filed on Jun. 29, 2012.

(30) Foreign Application Priority Data

May 24, 2012 (FR) .................................. 12 54758

(51) Int. Cl.
| | | |
|---|---|---|
| *A61Q 5/10* | (2006.01) | |
| *A61K 8/49* | (2006.01) | |
| *A61K 8/41* | (2006.01) | |
| *A61Q 5/06* | (2006.01) | |

(52) U.S. Cl.
CPC ............ *A61K 8/49* (2013.01); *A61K 8/41* (2013.01); *A61K 8/416* (2013.01); *A61K 8/4913* (2013.01); *A61K 8/4933* (2013.01); *A61K 8/4946* (2013.01); *A61Q 5/065* (2013.01); *A61Q 5/10* (2013.01); *A61K 2800/434* (2013.01)

(58) Field of Classification Search
CPC ........ A61Q 5/065; A61K 8/466; A61K 8/416; A61K 8/494; A61K 8/4946; A61K 8/498; A61K 8/49

USPC ................................................................ 8/405
See application file for complete search history.

(56) References Cited

U.S. PATENT DOCUMENTS 7,217,803 B2* 5/2007 Feiler .................. C09B 29/3617
524/93
2008/0184497 A1* 8/2008 Ruch ..................... C08K 5/0041
8/506

FOREIGN PATENT DOCUMENTS

| DE | 3434920 A1 | 5/1986 |
|---|---|---|
| DE | 102006011271 A1 | 9/2007 |
| EP | 0553705 A1 | 8/1993 |
| EP | 1199065 A2 | 4/2002 |
| WO | 2012/066028 A2 | 5/2012 |

OTHER PUBLICATIONS

STIC Search Report dated Mar. 17, 2015.*
STIC Search Report dated May 23, 2016.*
International Search Report for PCT/EP2013/060792.
Kirk Othmer Encyclopedia of Chemical Technology—"Hair Preparation," pt. 4, p. 18, published online: Sep. 18, 2009, DOI: 10.1002/0471238961.0801091816150812.a01.pub2.
Ullmann's Encyclopedia of Industrial Chemistry, "Hair Preparation," pt 5.2.3 p. 21; published online Jul. 15, 2006, DOI: 10.1002/14356007.a12-571.pub2.
English language abstract for DE 3434920 (May 7, 1986).
English language abstract for DE 102006011271 (Sep. 13, 2007).
English language abstract for EP 1199065 (Apr. 24, 2002).

* cited by examiner

*Primary Examiner* — Eisa Elhilo
(74) *Attorney, Agent, or Firm* — The Marbury Law Group, PLLC

(57) ABSTRACT

The invention relates to the dyeing of human keratin fibres, especially the hair, using anionic direct dyes bearing a particular ammonium or phosphonium counterion of formula (Ia) and/or optical brighteners of formula (Ib) $\text{Col}^{(-)}{}_m[X^+]_n$ (Ia) $\text{Azu}^{(-)}{}_m[X^+]_n$ (Ib) in which formulae (Ia) and (Ib): Azu/Col$^{(-)}$m, $R_1$, $R_2$, $R_3$, $R_4$, m and n are as defined in the description. The invention relates to a dye composition comprising an anionic compound of formula (Ia) and/or (Ib), and to a process for dyeing keratin fibres such as the hair, using the said composition. Similarly, the invention relates to novel anionic compounds of formula (Ia) or (Ib) and to the uses thereof for dyeing keratin fibres. This composition makes it possible to obtain chromatic, powerful and particularly fast coloration on keratin fibres and particularly lightening coloration via an optical effect on dark hair.

13 Claims, No Drawings

ANIONIC DYE OR BRIGHTENER BEARING AN AMMONIUM OR PHOSPHONIUM COUNTERION, DYE COMPOSITION COMPRISING THEM AND PROCESS FOR DYEING KERATIN FIBRES USING THESE DYES

CROSS REFERENCE TO RELATED APPLICATIONS

This is a national stage application of PCT/EP2013/060792, filed internationally on May 24, 2013, which claims priority to U.S. Provisional Application No. 61/666,782, filed on Jun. 29, 2012, as well as French Application No. 1254758, filed on May 24, 2012.

The invention relates to the dyeing of human keratin fibres using anionic direct dyes/optical brighteners bearing a particular ammonium or phosphonium counterion.

It is known practice to dye keratin fibres, especially the hair, by direct dyeing. The process conventionally used in direct dyeing consists in applying to keratin fibres direct dyes, which are coloured and colouring molecules that have affinity for the fibres, leaving them to diffuse and then rinsing the fibres.

The direct dyes that are conventionally used are, for example, dyes of the nitrobenzene type, anthraquinone dyes, nitropyridines and dyes of the azo, xanthene, acridine, azine or triarylmethane type. These dyes may be anionic, cationic or neutral. Anionic dyes or "acid dyes" are known as not being remanent on keratin fibres and for having poor dyeing power. In addition, they are more readily absorbed by the skin than by the hair, the effect of which is to dye the scalp during the dyeing of the hair. For these reasons, anionic dyes are sparingly used as dyes for hair dyeing (see, for example, *Kirk Othmer Encyclopedia of Chemical Technology*—"Hair Preparation", pt. 4, p. 18; Published Online: 18 Sep. 2009, DOI: 10.1002/0471238961.0801091816150812.a01.pub2; *Ullmann's Encyclopedia of Industrial Chemistry*, "Hair Preparation", pt 5.2.3 p. 21; Published Online: 15 Jul. 2006, DOI: 10.1002/14356007.a12_571.pub2). It is known practice to use dyes (A), (B) and (C) as defined below, which are anionic direct dyes bearing an ammonium or morpholinium counterion, for dyeing paper (DE 34 34 920).

The aim of the present invention is to provide novel dyes for human keratin fibres, such as the hair, which have improved dyeing properties, especially powerful, chromatic and/or remanent coloration of the hair with respect to external attacking factors, especially shampooing, without causing excessive staining of the scalp. The invention is also directed towards providing hair dyes which show little dyeing selectivity between the root and the end, which do not degrade keratin fibres, which do not impair their cosmetic properties and which stain the skin less. Another aim of the invention is to render hair more mat or less glossy or dull, and/or to discolor the white hair which turn yellow without the use of chemical oxidizing agent. Optic brightener can be used, but in general the uptake of the latter is not satisfactory.

These aims are achieved with the present invention, one subject of which is anionic dyes and optical brighteners chosen from those of formulae (Ia) and (Ib) below:

$$Col^{(-)}{}_m[X^+]_n \qquad (Ia)$$

$$Azu^{(-)}{}_m[X^+]_n \qquad (Ib)$$

and also the optical isomers and geometrical isomers thereof, and solvates thereof such as hydrates;

in which formulae (Ia) and (Ib):

$Col^{(-)}$ represents the anionic part of an anionic direct dye or "acid" dye comprising in its structure at least one sulfonate group and/or at least one carboxylate group and/or at least one phosphonate group comprising m anionic charge(s);

$Azu^{(-)}$ represents the anionic part of an anionic optical brightener comprising in its structure at least one sulfonate group and/or at least one carboxylate group and/or at least one phosphonate group comprising m anionic charge(s);

m and n represent an integer between 1 and 10 inclusive;

$X^+$ represents a monocationic or polycationic, in particular mono-, di- or tricationic, counterion or mixture of counterions chosen from:

a) the ammoniums and phosphoniums of formulae (1) and (2) below:

(1)

(2)

b) optionally substituted heteroaromatic groups bearing exocyclic or endocyclic, preferably endocyclic, cationic charge(s), such as (benz)imidazolium, indolinium, (benzo)triazolium, (benzo)pyrylium and (benzo)pyridinium groups, especially of formulae (3) and (4) below:

(3)

(4)

c) symmetrical or dissymmetrical, preferably symmetrical, dimers of formulae (1), (2), (3) and (4) such as those of formulae (1') to (8"):

(1')

-continued

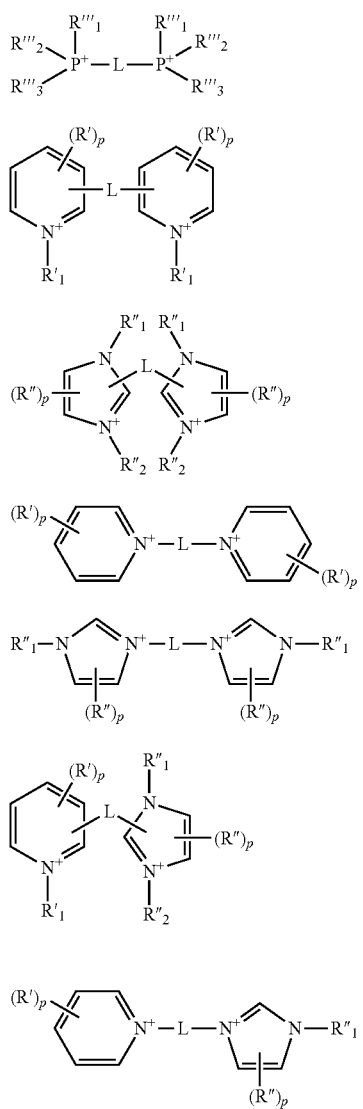

d) metallic cations of copper, iron, lithium, magnesium, manganese, gold and zinc, chosen from: $Cu^+$, $Cu^{2+}$, $Fe^{2+}$, $Fe^{3+}$, $Li^+$, $Mg^{2+}$, $Mn^{4+}$, $Au^{3+}$ and $Zn^{2+}$; and e) cationic oligomers or polymers;

$R_1$, $R_2$, $R_3$ and $R_4$, which may be identical or different, represent a group chosen from i) linear or branched $(C_1-C_{20})$alkyl; ii) $(C_2-C_{20})$alkenyl; iii) (hetero)aryl$(C_1-C_{20})$alkyl; (hetero)cycloalkyl$(C_1-C_{20})$alkyl or iv) (hetero)aryl; the alkyl or alkenyl group of the groups of i), ii), iii) or iv) possibly being interrupted with one or more identical or different heteroatoms chosen from an oxygen or sulfur atom, the amino —N(R)—, ammonium —$N^+(R_a)(R_b)$—, —C(O)—, —C(S)— group or a combination thereof, with R, $R_a$ and $R_b$, which may be identical or different, representing a hydrogen atom or an alkyl group;

preferentially, $R_1$, $R_2$, $R_3$ and $R_4$ represent a linear $(C_1-C_{20})$alkyl group substituted with at least one hydroxyl group, a $C_1-C_{10}$ alkylcarbonyloxy group, a $C_1-C_{10}$ alkoxy group, a hydroxycarbonyl group or a $(C_1-C_2)$alkylcarbonyloxy, carbamoyloxy or tri$(C_1-C_2)$alkylsilyl group;

or alternatively the radicals $R_1$ and $R_2$ form, together with the quaternized nitrogen or phosphorus atom, a saturated 5- or 6-membered heterocycle, the said heterocycle being optionally partially unsaturated, optionally interrupted with a heteroatom chosen from the oxygen atom, the group —N(R)—, or ammonium —$N^+(R_a)(R_b)$— with R, $R_a$ and $R_b$ as defined previously and/or the said heterocycle possibly being substituted with one or more groups such as $(C_1-C_6)$alkyl; preferentially, $R_1$ and $R_2$ are borne by a quaternized nitrogen atom, and in particular they form, together with the quaternized nitrogen atom, a pyrrolidinium, morpholinium, piperazinium or piperidinium group;

$R'_1$, $R''_1$ and $R''_2$, which may be identical or different, represent a group chosen from i) linear or branched $(C_1-C_{20})$alkyl; ii) $(C_2-C_{20})$alkenyl; the alkyl or alkenyl group of the groups of i) and ii) possibly being interrupted with one or more identical or different heteroatoms chosen from an oxygen or sulfur atom or ammonium —$N^+(R_a)(R_b)$—, —C(O)—, —C(S)— or a combination thereof, with R, $R_a$ and $R_b$ as defined previously;

$R'_1$, $R''_1$ and $R''_2$, which may be substituted with at least one hydroxyl, hydroxycarbonyl or carboxyl, $(C_1-C_6)$alkoxycarbonyl, alkyl$(C_1-C_6)$carbonyloxy, carbamoyloxy, (di)$(C_1-C_6)$(alkyl)silyl or tri$(C_1-C_5)$alkylsilyl group;

preferentially, $R'_1$ and $R''_1$ represent a linear or branched $(C_1-C_{10})$alkyl group optionally substituted with at least one hydroxyl group, a hydroxycarbonyl group or a $(C_1-C_2)$alkylcarbonyloxy, carbamoyloxy or tri$(C_1-C_2)$alkylsilyl group;

R' and R" represent a group chosen from i) $(C_1-C_5)$alkyl optionally substituted with one or more radicals chosen from hydroxyl radicals, ii) $(C_1-C_5)$alkoxycarbonyl, iii) hydroxyl, iv) halogen, v) $(C_1-C_5)$alkoxy, vi) (poly)hydroxy$(C_1-C_5)$alkoxy, vii) (di)$(C_1-C_5)$(alkyl)amino, viii) nitro, ix) acylamino (—N(R)—C(O)R') with R representing a hydrogen atom or a (hydroxy)$(C_1-C_5)$ alkyl radical, x) carbamoyl $((R)_2N—C(O)—)$ with R as defined for ix), xi) carboxylic acid or ester, (—O—C(O)R') or (—C(O)OR') with R' as defined for ix) the carboxylic radical possibly being in acid or salified form, preferably with an alkali metal or a substituted or unsubstituted ammonium, xii) alkylsulfonylamino (R'S(O)_2—N(R)—) or aminosulfonyl $((R)_2N—S(O)_2—)$ with R as defined for ix), xiii) (poly)haloalkyl, preferentially trifluoromethyl $(CF_3)$; preferably, R' and R" are chosen from $(C_1-C_5)$alkyl and $((R)_2N—C(O)—)$;

or alternatively when p is greater than or equal to 2, two groups R" or R" borne by two contiguous carbon atoms together form a (hetero)cycle or a (hetero)aryl, preferably a benzo group;

$R'''_1$, $R'''_2$, $R'''_3$ and $R'''_4$, which may be identical or different, represent a group chosen from i) linear or branched $(C_1-C_{20})$alkyl; ii) $(C_2-C_{20})$alkenyl; the alkyl or alkenyl group of the groups of i) and ii) possibly being substituted and/or interrupted with one or more identical or different heteroatoms chosen from oxygen and sulfur, the amino —N(R)—, ammonium —$N^+(R_a)(R_b)$—, —CO—, —C(S)— group or a combination thereof, with R, $R_a$ and $R_b$, which may be identical or different, representing a hydrogen atom or an alkyl group;

in particular, $R'''_1$, $R'''_2$, $R'''_3$ and $R'''_4$, which may be identical or different, represent a $(C_1-C_{20})$alkyl radical; preferentially, $R'''_1$, $R'''_2$, $R'''_3$ and $R'''_4$, which may be identical or different, represent a $(C_1$-$C_{14})$ alkyl group;

p is equal to 0, 1, 2, 3 or 4;

L represents a linear or branched, saturated or unsaturated divalent $C_1$-$C_{30}$ and preferably $C_2$-$C_{20}$ hydrocarbon-based chain, optionally interrupted and/or optionally terminated at one or both of its ends with one or more divalent groups or combinations thereof chosen from: —N($R_a$)—; —N$^+$($R_a$)($R_b$)—, Q$^-$; —O—; —S—; —S(O)—, —S(O)$_2$—, —C(O)— and —C(S)— with $R_a$ and $R_b$, which may be identical or different, chosen from a hydrogen atom and a $C_1$-$C_4$ alkyl, hydroxy($C_1$-$C_8$)alkyl or amino($C_1$-$C_8$)alkyl radical and Q$^-$ represents an organic or mineral anionic counterion;

an aromatic or non-aromatic saturated or unsaturated, fused or non-fused, cationic or non-cationic (hetero) cyclic radical, optionally comprising one or more identical or different heteroatoms, optionally substituted with one or more alkyl radicals preferably chosen from methyl and ethyl, preferably phenylene optionally substituted especially with one or more methyl radicals;

preferentially, the divalent group(s) or combinations thereof are chosen from —S—, —O—; —N($R_a$)—; —C(O)— with $R_a$ chosen from a hydrogen atom and a $C_1$-$C_4$ alkyl radical;

it being understood that:

when the dyes of formula (Ia) are such that $R_1$, $R_2$, $R_3$ and $R_4$, which may be identical or different, represent i) linear or branched $(C_1$-$C_{20})$alkyl; ii) $(C_2$-$C_{20})$alkenyl; the alkyl or alkenyl group of the groups of i) and ii) possibly being interrupted with one or more identical or different heteroatoms chosen from an oxygen or sulfur atom or the amino —N(R)— group, then at least one of the said radicals $R_1$, $R_2$, $R_3$ and $R_4$ is substituted with at least one hydroxyl, hydroxycarbonyl or carboxyl, $(C_1$-$C_6)$alkoxycarbonyl, $(C_1$-$C_6)$alkylcarbonyloxy, carbamoyloxy, (di)$(C_1$-$C_6)$(alkyl)silyl or tri$(C_1$-$C_5)$alkylsilyl group; preferentially $R_1$, $R_2$, $R_3$ and $R_4$ represent a linear $(C_1$-$C_{20})$alkyl group substituted with at least one hydroxyl group, a hydroxycarbonyl group or a $(C_1$-$C_2)$alkylcarbonyloxy, carbamoyloxy or tri$(C_1$-$C_2)$ alkylsilyl group;

when p is equal to 2, 3 or 4, then the groups R' are identical or different and R" are identical or different;

when the anionic part of the anionic direct dye or of the anionic optical brightener contains a sulfonate group or a carboxylate group, then m=n=1; and when the anionic part of the anionic direct dye or of the anionic optical brightener contains anionic groups other than the sulfonate or carboxylate group, it is combined with one or more organic or mineral cationic counterions or X$^+$ for affording the electrical neutrality of formula (Ia) or (Ib);

the compound of formula (Ia) cannot represent compounds (A), (B) or (C);

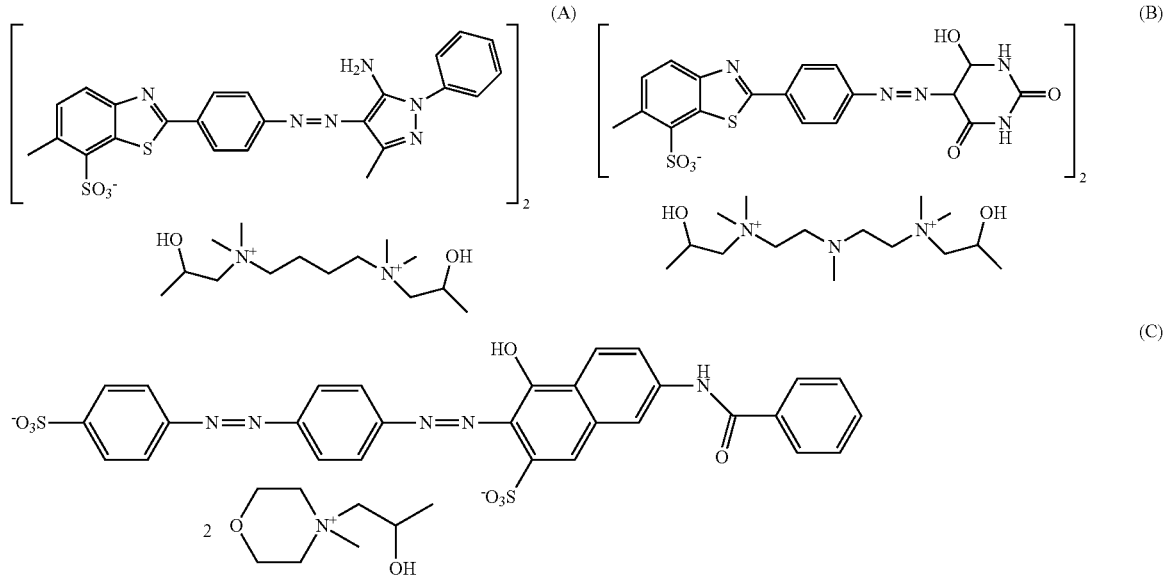

Another subject of the invention is a dye composition comprising, in a suitable cosmetic medium, at least one anionic dye of formula (Ia) and/or at least one optical brightener of formula (Ib) as defined previously, it being understood that the compound(s) of formula (Ia) cannot represent compounds (A), (B) or (C) as defined previously.

Another subject of the invention concerns a process for dyeing keratin fibres, using at least one or more anionic dyes of formula (Ia) and/or at least one optical brightener (Ib) as defined previously.

Another subject of the invention concerns the use of at least one anionic dye of formula (Ia) and/or at least one optical brightener of formula (Ib) as defined previously for dyeing keratin fibres such as the hair.

Another subject of the invention concerns the use of at least one fluorescent anionic dye of formula (Ia) as defined, particularly in the orange range, for optically lightening dark keratin fibres such as hair with a tone depth of less than or equal to 6 and preferentially less than or equal to 4, even in the absence of a chemical oxidizing agent other than atmospheric oxygen.

Another subject of the invention concerns the use of at least one optical brightener of formula (Ib) as defined, particularly in the blue range, for optically lightening dark keratin fibres such as hair with a tone depth of greater than or equal to 6 and preferentially greater than or equal to 8, even in the absence of a chemical oxidizing agent other than atmospheric oxygen.

Another subject of the invention concerns the use of at least one fluorescent anionic dye of formula (Ia) as defined previously, particularly in the orange range, combined with at least one optical brightener of formula (Ib) as defined previously, for optically lightening dark keratin fibres such as hair with a tone depth of less than or equal to 6 and preferentially less than or equal to 4, even in the absence of a chemical oxidizing agent other than atmospheric oxygen.

With the dyes of the invention, it is possible to improve the dyeing properties of anionic dyes especially in terms of chromaticity, power and fastness by replacing the "standard" cationic counterions such as alkali metal or alkaline-earth metal cations with one or more organic or mineral (poly)cations $X^+$ as defined previously. It has also been found that the optical lightening can be improved by using dye(s) of formula (Ia) as defined previously and/or optical brightener(s) of formula (Ib) as defined previously.

The anionic compounds of formulae (Ia) and (Ib) according to the invention are moreover stable with respect to oxidizing agents, and show satisfactory solubility in cosmetic dyeing media.

Thus, the compounds of formulae (Ia) and (Ib) make it possible especially to significantly improve the remanence, in particular with respect to shampooing, and/or the optical lightening of dark keratin fibres.

The term "dark keratin fibres", especially dark hair, means fibres which are naturally or artificially dark and whose tone depth is less than or equal to 6 (dark blond) and preferably less than or equal to 4 (chestnut-brown). The notion of "tone" is based on the classification of natural shades, one tone separating each shade from the shade immediately following or preceding it. This definition and the classification of natural shades are well known to hairstyling professionals and are published in the book *Sciences des traitements capillaires* [Hair treatment sciences] by Charles Zviak, 1988, published by Masson, pp. 215 and 278. The tone depths range from 1 (black) to 10 (very light blond), one unit corresponding to one tone; the higher the figure, the lighter the shade.

For the purposes of the present invention, and unless otherwise indicated:
a "hydrocarbon-based chain" is "unsaturated" when it comprises one or more double bonds and/or one or more triple bonds;
the "aryl" or "heteroaryl" radicals or the aryl or heteroaryl part of a radical may be substituted with at least one substituent borne by a carbon atom, chosen from:
  a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
  a halogen atom such as chlorine, fluorine or bromine;
  a hydroxyl group;
  a $C_1$-$C_2$ alkoxy radical;
  a $C_2$-$C_4$ (poly)hydroxyalkoxy radical;
  an amino radical;
  nitro;
  a 5- or 6-membered heterocycloalkyl radical;
  an optionally cationic 5- or 6-membered heteroaryl radical, preferentially imidazolium, optionally substituted with a ($C_1$-$C_4$)alkyl radical, preferentially methyl;
  an amino radical substituted with one or two identical or different $C_1$-$C_6$ alkyl radicals, optionally bearing at least:
    i) a hydroxyl group;
    ii) one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom;
  an acylamino radical (—N(R)—C(O)R') in which the radical R is a hydrogen atom or a $C_1$-$C_4$ alkyl radical optionally bearing at least one hydroxyl group and the radical R' is a $C_1$-$C_2$ alkyl radical;
  a carbamoyl radical ((R)$_2$N—C(O)—) in which the radicals R, which may be identical or different, represent a hydrogen atom or a $C_1$-$C_4$ alkyl radical optionally bearing at least one hydroxyl group;
  a carboxylic acid or ester radical, (—O—C(O)R') or (—C(O)OR'), in which the radical R' is a hydrogen atom or a $C_1$-$C_4$ alkyl radical optionally bearing at least one hydroxyl group, and the radical R' is a $C_1$-$C_2$ alkyl radical;
  the carboxylic radical possibly being in acid or salified form (preferably with an alkali metal or a substituted or unsubstituted ammonium);
  an alkylsulfonylamino radical (R'S(O)$_2$—N(R)—) in which the radical R represents a hydrogen atom or a $C_1$-$C_4$alkyl radical optionally bearing at least one hydroxyl group and the radical R' represents a $C_1$-$C_4$ alkyl radical, or a phenyl radical;
  an aminosulfonyl radical ((R)$_2$N—S(O)$_2$—) in which the radicals R, which may be identical or different, represent a hydrogen atom or a $C_1$-$C_4$ alkyl radical optionally bearing at least one hydroxyl group,
  a cyano group (CN);
  a (poly)haloalkyl group, preferentially trifluoromethyl (CF$_3$);
the cyclic or heterocyclic part of a non-aromatic radical may be substituted with at least one substituent borne by a carbon atom, chosen from the groups:
hydroxyl,
$C_1$-$C_4$ alkoxy or $C_2$-$C_4$ (poly)hydroxyalkoxy,
alkylcarbonylamino ((RC(O)—NR'—) in which the radical R' is a hydrogen atom or a $C_1$-$C_4$ alkyl radical optionally bearing at least one hydroxyl group, and the radical R is a $C_1$-$C_2$ alkyl radical or an amino radical substituted with two $C_1$-$C_4$ alkyl groups, which may be identical or different, optionally bearing at least one hydroxyl group, the said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy ((RC(O)—O—) in which the radical R is a $C_1$-$C_4$ alkyl radical or an amino radical substituted with two identical or different $C_1$-$C_4$ alkyl groups optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl ((RO—C(O)—) in which the radical R is a $C_1$-$C_4$ alkyl radical or an amino radical substituted with two identical or different $C_1$-$C_4$ alkyl groups optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups;

an "aryl" radical represents a fused or non-fused monocyclic or polycyclic group containing from 6 to 22 carbon atoms, and in which at least one ring is aromatic; in particular, the aryl radical is a phenyl, biphenyl, naphthyl, indenyl, anthracenyl or tetrahydronaphthyl and more preferentially phenyl;

a "heteroaryl" radical represents a 5- to 22-membered, fused or non-fused monocyclic or polycyclic group, comprising from 1 to 6 heteroatoms chosen from nitrogen, oxygen, sulfur and selenium, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof;

a "cyclic" radical is a "cycloalkyl" radical, i.e. a non-aromatic, monocyclic or polycyclic, fused or non-fused radical, containing from 5 to 22 carbon atoms, which may comprise one or more unsaturations, such as cyclohexyl or cyclopentyl;

a "heterocyclic" radical is a non-aromatic, monocyclic or polycyclic, fused or non-fused 5- to 22-membered radical, comprising from 1 to 6 heteroatoms chosen from nitrogen, oxygen, sulfur and selenium atoms, morpholinyl, thiomorpholinyl, piperidyl, piperazinyl, pyrrolidinyl, tetrahydrofuryl, tetrahydrothiophenyl, azepanyl, thioazepanyl; preferentially pyrrolidinyl and morpholino;

a "cationic heteroaryl radical" is a heteroaryl group as defined previously, which comprises an endocyclic or exocyclic cationic group, when the charge is endocyclic, it is included in the electron delocalization via the mesomeric effect, for example it is a pyridinium, imidazolium or indolinium group:

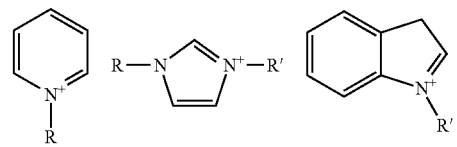

with R and R' being a heteroaryl substituent as defined previously and particularly a (hydroxy)($C_1$-$C_8$)alkyl group such as methyl;

when the charge is exocyclic, it is not included in the electron delocalization via the mesomeric effect, for example it is an ammonium or phosphonium substituent $R^+$ such as trimethylammonium, which is outside the heteroaryl such as pyridyl, indolyl, imidazolyl or naphthalimidyl in question:

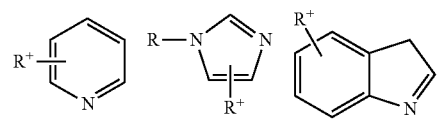

with R being a heteroaryl substituent as defined previously and $R^+$ an ammonium $R_aR_bR_cN^+$—, phosphonium $R_aR_bR_cP^+$— or ammonium $R_aR_b$ $R_cN^+$—($C_1$-$C_6$)alkylamino group with $R_a$, $R_b$ and $R_c$, which may be identical or different, representing a hydrogen atom or a ($C_1$-$C_8$)alkyl group such as methyl;

an "alkyl" radical is a linear or branched $C_1$-$C_{16}$ and preferably $C_1$-$C_8$ hydrocarbon-based radical; particularly $C_1$-$C_4$ such as methyl or ethyl;

an "alkenyl" radical is a linear or branched $C_2$-$C_{20}$ hydrocarbon-based radical comprising one or more conjugated or unconjugated double bonds, in particular a $C_4$-$C_{10}$ radical comprising one, two or three double bonds, preferentially only one double bond;

the term "optionally substituted" attributed to the alkyl radical means that the said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, the said alkyl radicals possibly forming, with the nitrogen atom that bears them, a 5- to 7-membered heterocycle, optionally comprising another nitrogen or non-nitrogen heteroatom;

an "alkoxy" radical is an alkyl-oxy or alkyl-O— radical for which the alkyl radical is a linear or branched $C_1$-$C_{16}$ and preferentially $C_1$-$C_8$ hydrocarbon-based radical; particularly $C_1$-$C_4$ such as methoxy or ethoxy, and when the alkoxy group is optionally substituted, this means that the alkyl group is optionally substituted as defined above;

a "(poly)haloalkyl" radical is an "alkyl" radical as defined previously, in which one or more hydrogen atoms are substituted or replaced with one or more halogen atoms such as the fluorine, chlorine or bromine atom; a polyhaloalkyl that may be mentioned is the trifluoromethyl group;

an "alkylthio" radical is a radical alkyl-S— for which the alkyl radical is a linear or branched $C_1$-$C_{16}$ and preferentially $C_1$-$C_8$ hydrocarbon-based radical; particularly $C_1$-$C_4$ such as methylthio or ethylthio, and when the alkylthio group is optionally substituted, this means that the alkyl group is optionally substituted as defined above;

a cationic counterion is organic or mineral and preferentially chosen from alkali metal or alkaline-earth metal cations such as Na, Mg, K and Ca, and organic cations such as ammonium $NH_4^+$;

when the expression "at least one" is used, "one or more" is implied.

Furthermore, unless otherwise indicated, the limits delimiting the extent of a range of values are included in this range of values.

According to the present invention, the term "dye" means a compound which has the capacity of colouring and which is in the form of a coloured compound that may be observed with the naked eye, i.e. absorbing light at a wavelength in the UV and visible radiation range, at a wavelength $\lambda_{abs}$ of between 250 and 800 nm, particularly in the visible spectrum between 400 and 700 nm.

The term "fluorescent dye" means a dye as defined previously, which, besides the fact that it is coloured, is fluorescent, i.e. it has the capacity of re-emitting at least part of the absorbed light, preferably at least the majority of the absorbed light, in the visible region at a wavelength higher than the absorbed wavelength. In particular, the fluorescent dye is capable of absorbing UV or visible radiation at a wavelength $\lambda_{abs}$ of between 250 and 800 nm and capable of re-emitting in the visible range at an emission wavelength $\lambda_{em}$ of between 400 and 800 nm. Preferably, the fluorescent dye is a dye in the orange, violet, blue and green range. More preferentially, the fluorescent dye(s) (Ia) are dyes in the orange range.

The term "optical brightener" means a colourless or very weakly coloured organic compound which absorbs light in the ultraviolet spectrum, i.e. at a wavelength $\lambda_{abs}$ of between 300 and 430 nm, in particular in the UVA range between 300 and 400 nm, and which re-emits at least part and preferably the majority of the absorbed light in the blue range, i.e. at an emission wavelength $\lambda_{em}$ of between 400 and 525 nm and in particular between 400 and 500 nm.

I. Dyes of Formula (Ia) and Optical Brighteners (Ib)

The Cationic Counterion $X^+$

According to a preferred embodiment of the invention, $X^+$ represents an ammonium belonging to formula (1) as defined previously. More particularly, $X^+$ is chosen from the ammoniums 1 to 17:

| | |
|---|---|
| N,N,N-trimethyl-1-hexanaminium | 1 |
| N,N-dimethylpyrrolidinium | 2 |
| 1-ethyl-1-methylpyrrolidinium | 3 |
| N-ethyl-N-methyl-N-(1-methylethyl)-2-propanaminium | 4 |
| N,N,N-tributyl-1-heptanaminium | 5 |
| N,N,N-tributyl-1-hexanaminium | 6 |
| N,N,N-triethyl-1-octanaminium | 7 |
| 1-methyl-1-pentylpyrrolidinium | 8 |
| 1-hexyl-1-methylpyrrolidinium | 9 |
| N,N,N-trimethyl-1-octanaminium | 10 |
| cocoalkylpentaethoxymethylammonium | 11 |
| N-hexyl-N,N,N-triethylammonium | 12 |
| Cetyltrimethylammonium | 13 |
| N,N,N-triethyl-1-heptanaminium | 14 |
| N,N,N-tributyl-1-hexanaminium | 15 |
| N-ethyl-N,N-bis(1-methylethyl)-1-heptanaminium | 16 |
| N,N,N-tributyl-1-octanaminium | 17 |

Choline and derivatives thereof, betaines and derivatives thereof and carnitine and derivatives thereof as defined below are also suitable for use:

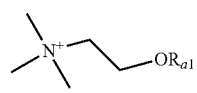
17a

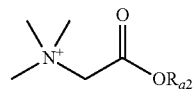
17b

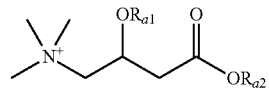
17c with:
- $R_{a1}$ representing a hydrogen atom or a $(C_1$-$C_{10})$alkyl or $(C_1$-$C_{10})$alkylcarbonyl radical;
- $R_{a2}$ representing a hydrogen atom or a $(C_1$-$C_{10})$alkyl radical;

According to a particular mode of the invention, the anionic compound is of formula (Ib) and the cationic counterion is of ammonium type $N^+R_1R_2R_3R_4$ with $R_1$, $R_2$, $R_3$ and $R_4$, which may be identical or different, representing a group chosen from i) $(C_1$-$C_{20})$alkyl; ii) $(C_2$-$C_{20})$alkenyl; the alkyl or alkenyl group of the groups of i) and ii) possibly being interrupted with one or more identical or different heteroatoms chosen from oxygen, sulfur or $N(R\alpha)$ with $R\alpha$ representing a hydrogen atom or an alkyl group; preferentially, $R_1$, $R_2$, $R_3$ and $R_4$ are identical and more particularly represent a linear $(C_1$-$C_6)$alkyl group, such as methyl, ethyl, propyl or butyl.

According to a preferred embodiment of the invention, $X^+$ represents a dimer associated with the ammoniums belonging to formula (1') as defined previously. More particularly, $X^+$ is chosen from the diammoniums 18 to 58:

| | |
|---|---|
| $(CH_3)_3N^+$—$(CH_2)_5$—$N^+(CH_3)_3$ | 18 |
| $(CH_3)_3N^+$—$(CH_2)_6$—$N^+(CH_3)_3$ | 19 |
| $(CH_3)_3N^+$—$(CH_2)_7$—$N^+(CH_3)_3$ | 20 |

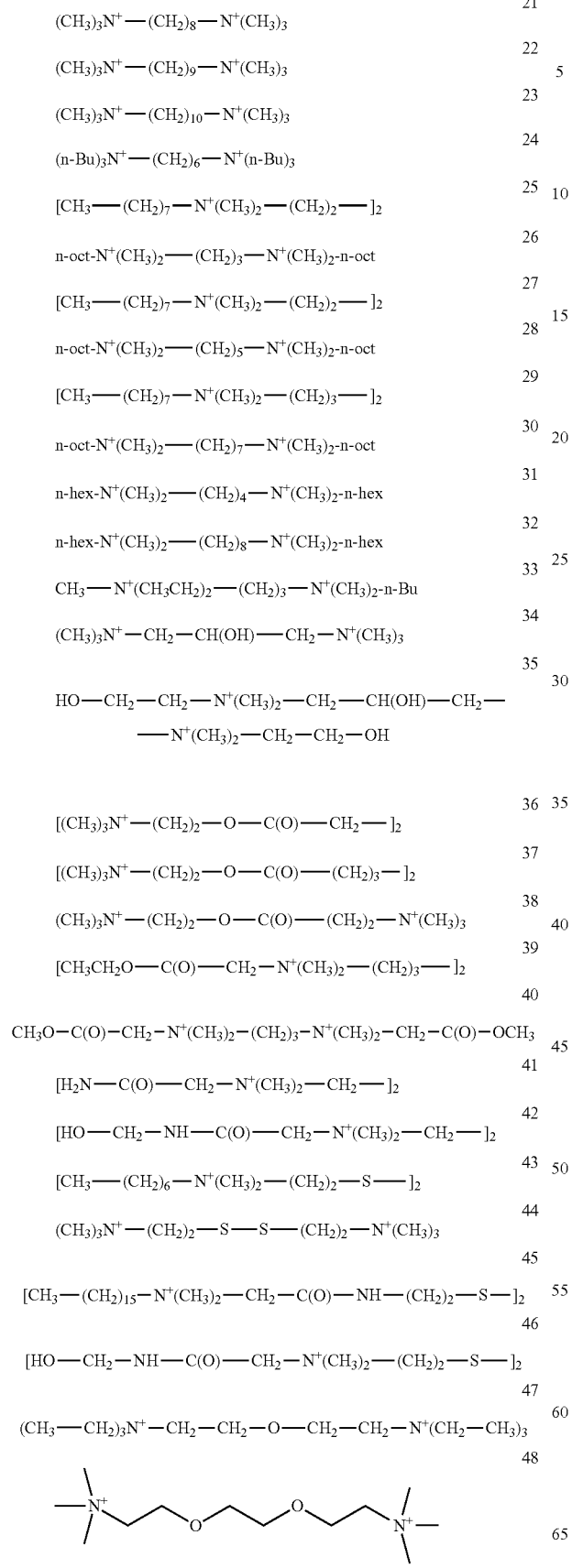
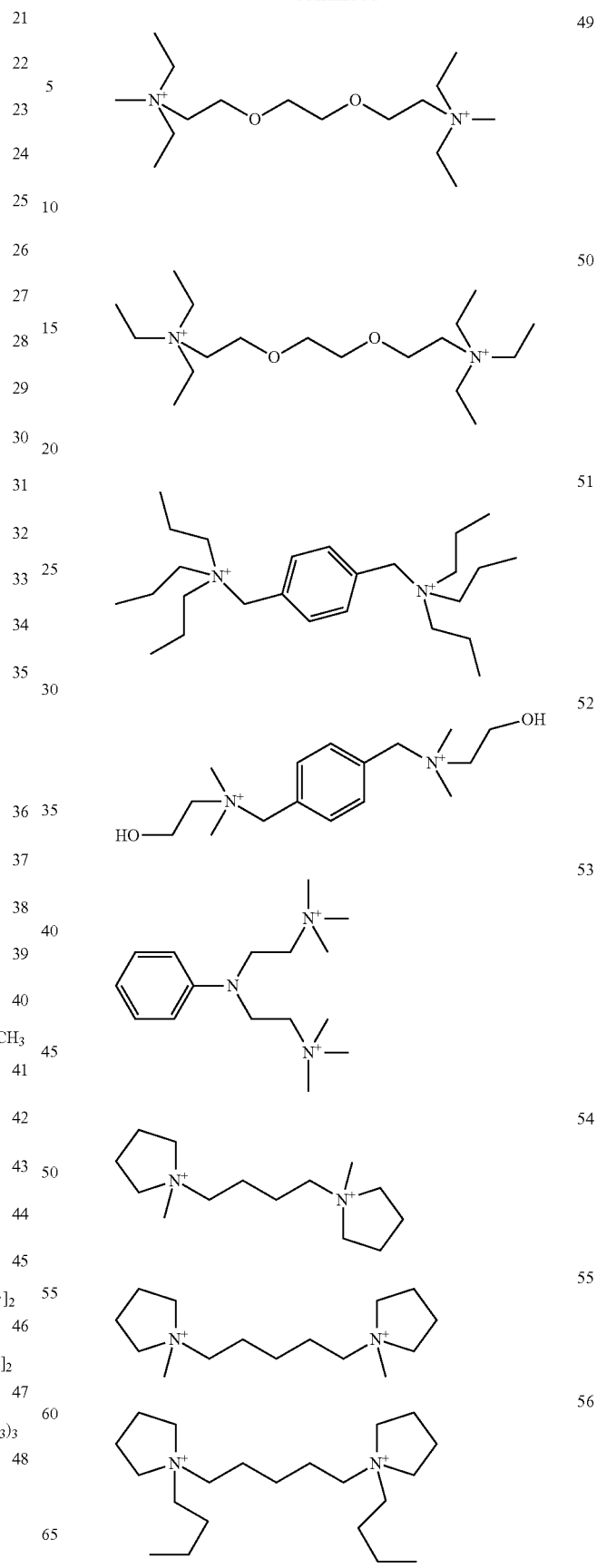

-continued

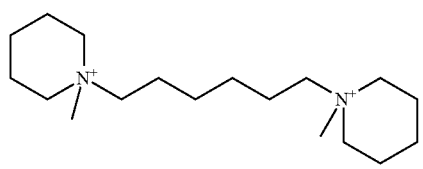
57

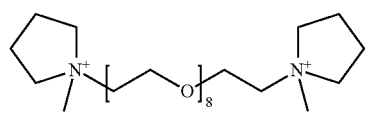
58

According to a preferred embodiment of the invention, X⁺ represents a pyridinium belonging to formula (3) as defined previously. More particularly, X⁺ is chosen from the pyridiniums 59 to 72:

N-ethylpyridinium  59

1-ethyl-3-methylpyridinium  60

N-butylpyridinium  61

4-(dimethylamino)-1-ethylpyridinium  62

1-ethylnicotinic acid ethyl ester  63

1-hexyl-3-methylpyridinium  64

1-butyl-3-methylpyridinium  65

1-hexyl-3,5-dimethylpyridinium  66

4-(dimethylamino)-1-hexypyridinium  67

1-butylnicotinic acid butyl ester  68

1-methyl-3-octylpyridinium; 1-  69

1-hexyl-3-methyl-4-(dimethylamino)pyridinium  70

1-hexyl-4-(4-methylpiperidino)pyridinium  71

1-hexyl-4-(4-methylpiperidino)pyridinium  72

According to a preferred embodiment of the invention, X⁺ represents a dimer associated with the pyridiniums belonging to formula (3') as defined previously. More particularly, X⁺ is chosen from the dipyridiniums 73 to 116:

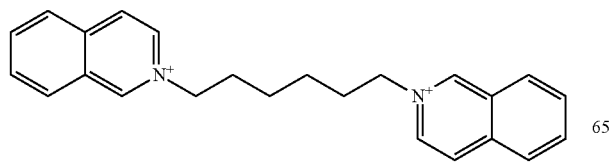
73

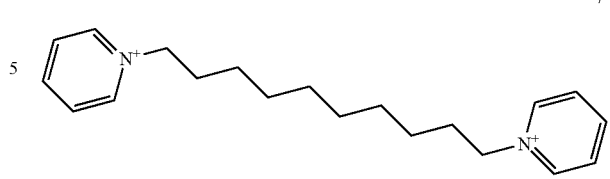
74

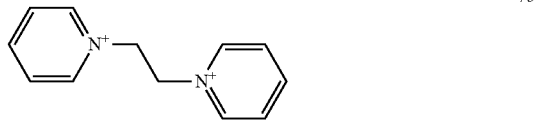
75

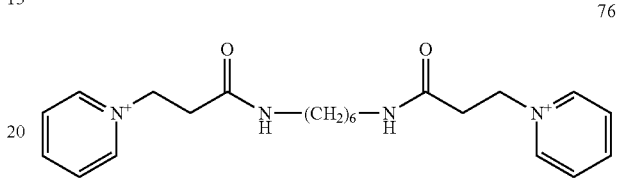
76

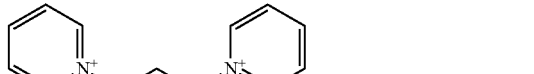
77

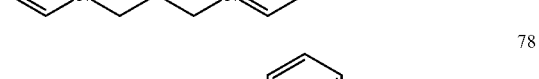
78

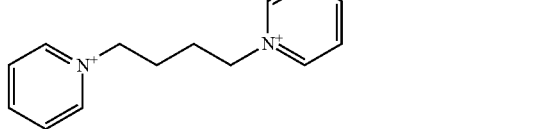
79

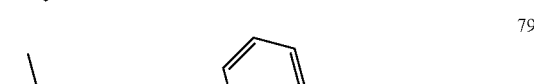
80

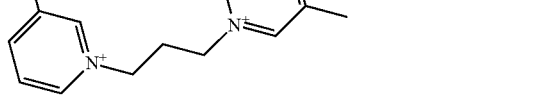
81

82

83
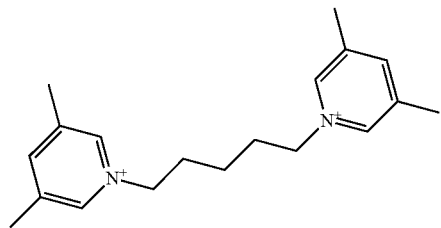
84
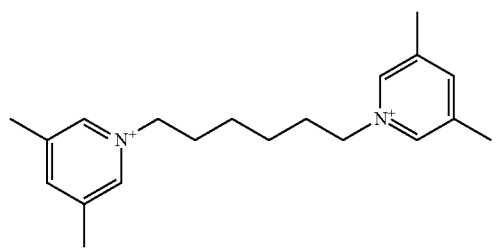
85
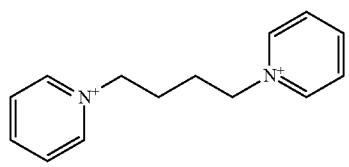
86
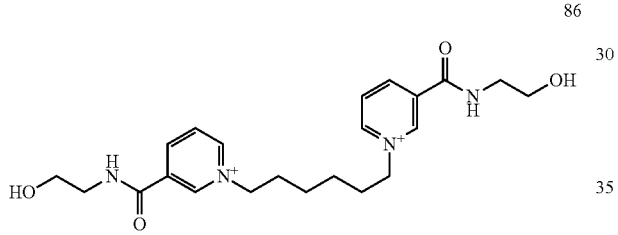
87
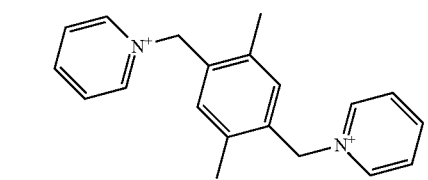
88
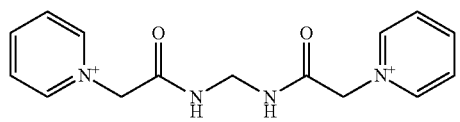
89
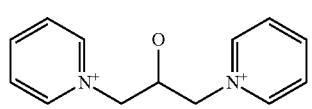
90
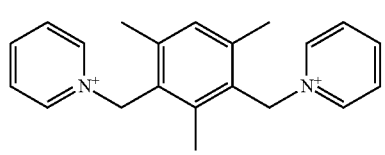
91
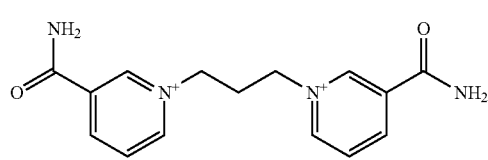
92
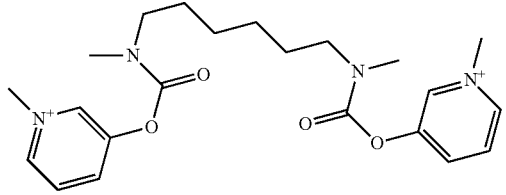
93
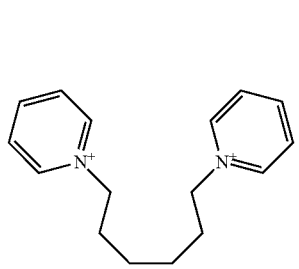
94
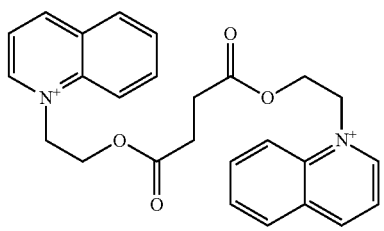
95
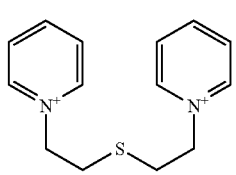
96
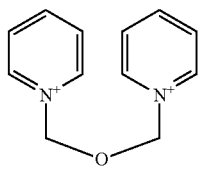
97
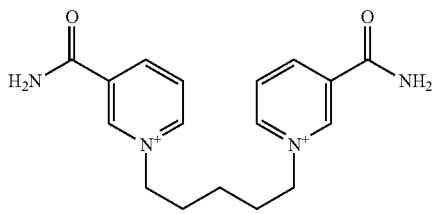
98
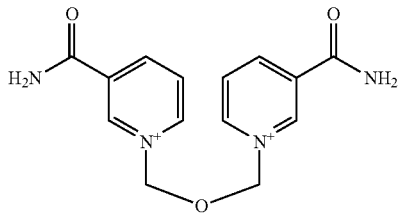

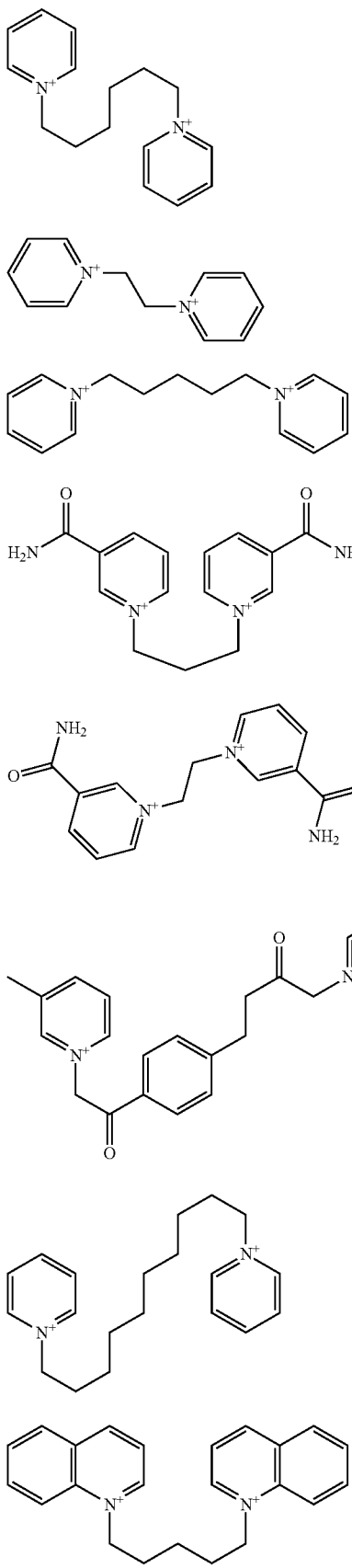

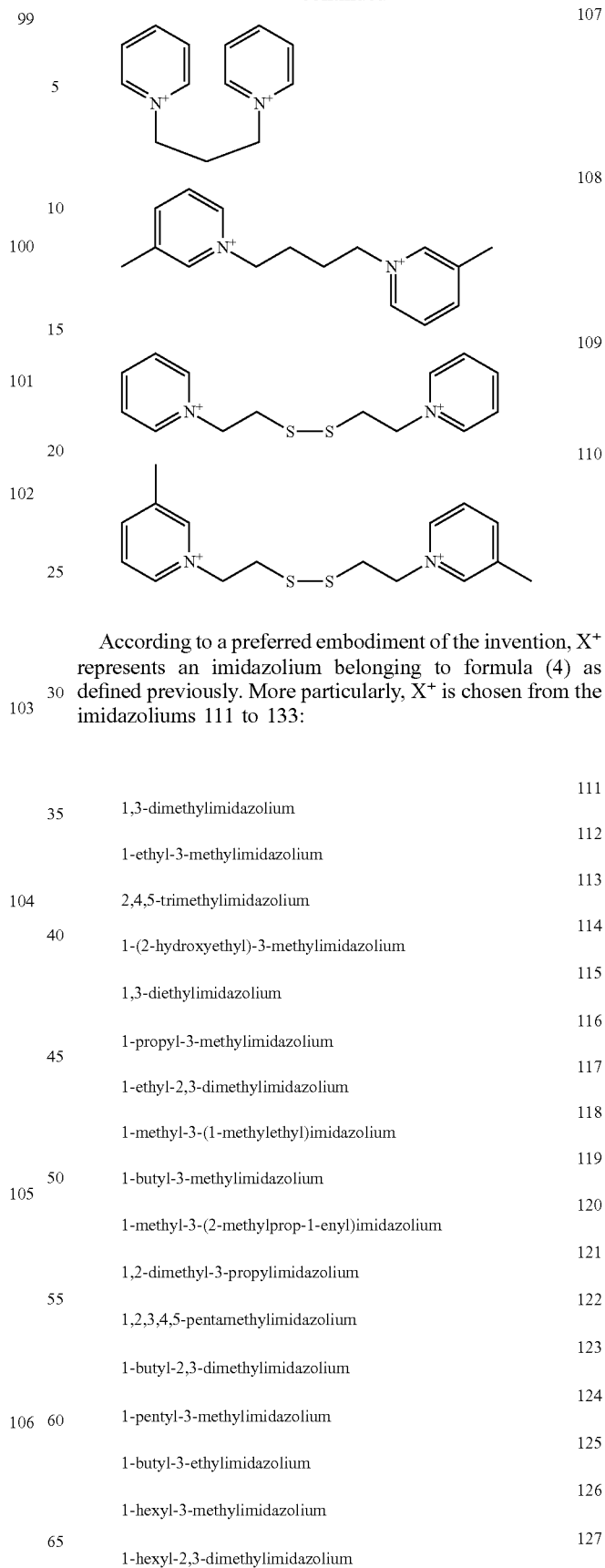

According to a preferred embodiment of the invention, X⁺ represents an imidazolium belonging to formula (4) as defined previously. More particularly, X⁺ is chosen from the imidazoliums 111 to 133:

| | |
|---|---|
| 1,3-dimethylimidazolium | 111 |
| 1-ethyl-3-methylimidazolium | 112 |
| 2,4,5-trimethylimidazolium | 113 |
| 1-(2-hydroxyethyl)-3-methylimidazolium | 114 |
| 1,3-diethylimidazolium | 115 |
| 1-propyl-3-methylimidazolium | 116 |
| 1-ethyl-2,3-dimethylimidazolium | 117 |
| 1-methyl-3-(1-methylethyl)imidazolium | 118 |
| 1-butyl-3-methylimidazolium | 119 |
| 1-methyl-3-(2-methylprop-1-enyl)imidazolium | 120 |
| 1,2-dimethyl-3-propylimidazolium | 121 |
| 1,2,3,4,5-pentamethylimidazolium | 122 |
| 1-butyl-2,3-dimethylimidazolium | 123 |
| 1-pentyl-3-methylimidazolium | 124 |
| 1-butyl-3-ethylimidazolium | 125 |
| 1-hexyl-3-methylimidazolium | 126 |
| 1-hexyl-2,3-dimethylimidazolium | 127 |

| | |
|---|---|
| 1-heptyl-3-methylimidazolium | 128 |
| 1-octyl-3-methylimidazolium | 129 |
| 1-methyl-3-nonylimidazolium | 130 |
| 1-decyl-3-methylimidazolium | 131 |
| 1-dodecyl-3-methylimidazolium | 132 |
| 1-dodecyl-3-methylimidazolium | 133 |

According to a preferred embodiment of the invention, $X^+$ represents a dimer associated with the imidazoliums belonging to formula (4') as defined previously. More particularly, $X^+$ is chosen from the diimidazoliums 134 to 167:

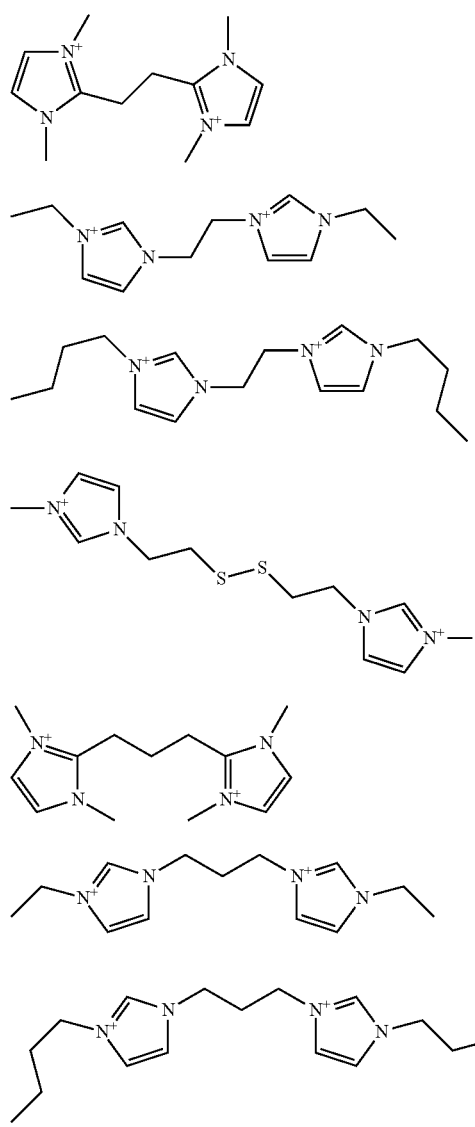
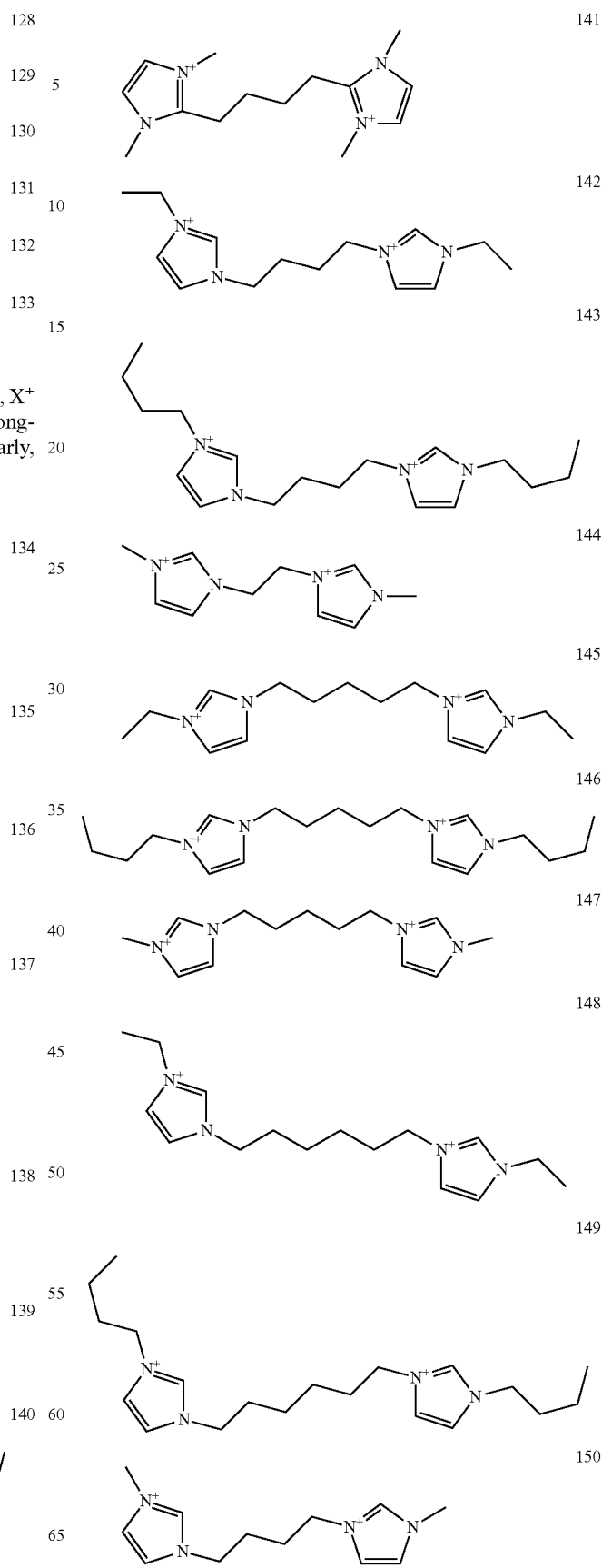

23
-continued
151
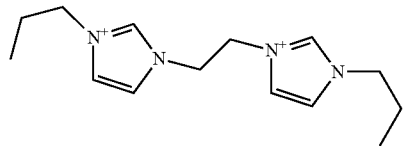
152
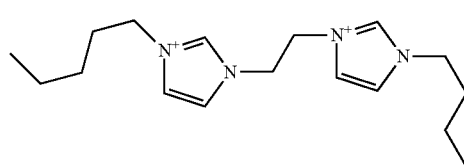
153
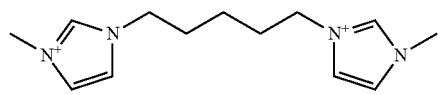
154
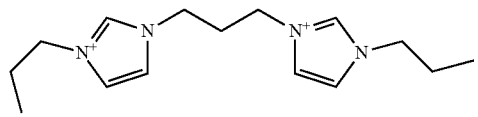
155
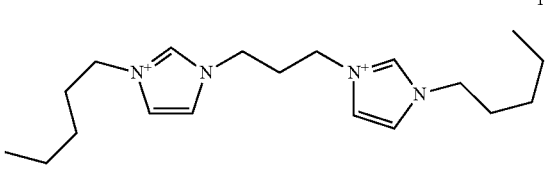
156
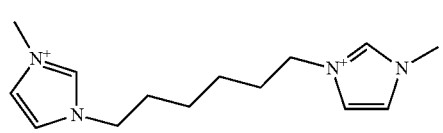
157
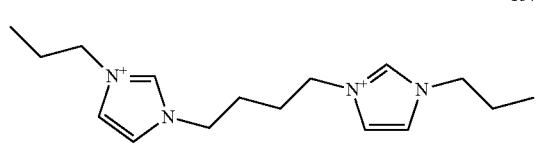
158
159
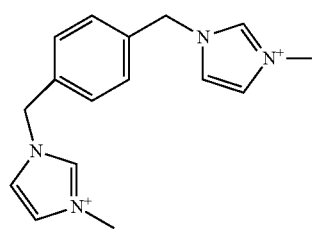
160
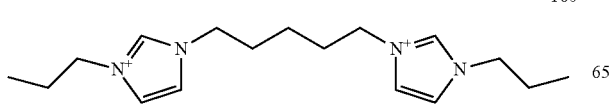
24
-continued
161
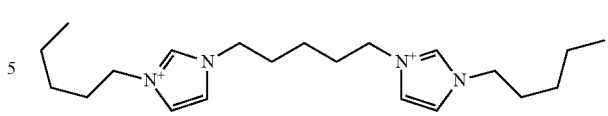
162
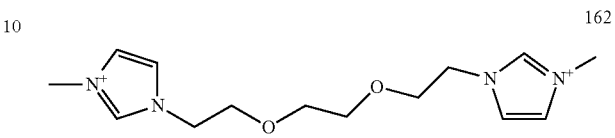
163
164
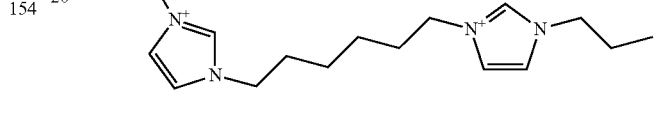
165
166
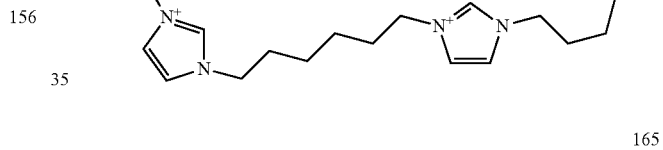
167
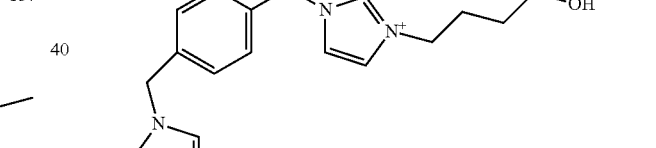
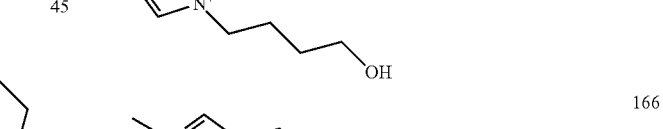
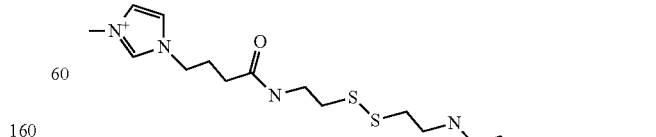

According to a preferred embodiment of the invention, $X^+$ represents a phosphonium belonging to formula (2) as defined previously. More particularly, $X^+$ is chosen from the phosphoniums 168 to 172:

triisobutylmethylphosphonium   168 trihexyl(tetradecyl)phosphonium   169 tetrabutylphosphonium   170 tri-i-butyl(methyl)phosphonium   171 tributyl(tetradecyl)phosphonium   172

According to a preferred embodiment of the invention, $X^+$ represents a metal cation chosen from copper, iron, lithium, magnesium, manganese, gold and zinc and mineral salts such as magnesium sulfates and organic salts such as manganese gluconate.

According to a preferred embodiment of the invention, $X^+$ represents a cationic oligomer or polymer. The term "cationic oligomers or polymers" means oligomers or polymers derived from the alkylation of non-protonated heteroatoms. In other words, a polymer such as protonated Primene ($81H^+$) is not a cationic polymer within the meaning of the invention.

When $X^+$ represents a cationic oligomer or polymer, any oligomer or polymer bears at least one cationic charge. The following are envisaged as examples of cationic oligomers or polymers:

Polyquaterniums such as Polyquaternium-11, hydroxypropyl trimonium (guar) chloride, Polyquaternium-7, Polyquaternium-10 and Polyquaternium-4 ionenes cationic glycans cationic dextrans cationic silicones such as amodimethicone (and) trideceth-12 (and) cetrimonium chloride, amodimethicone (and) trideceth-6 (and) cetrimonium chloride.

The Anionic Part Col⁻ or Azu⁻

The anionic direct dyes of formula (Ia) according to the invention are "derived" from dyes commonly known as "acid dyes" for their affinity with alkaline substances (see, for example, "*Industrial Dyes, Chemistry, Properties, Application*", Klaus Hunger Ed. Wiley-VCH Verlag GmbH & Co KGaA, Weinheim 2003). Anionic or acid dyes are known in the literature (see, for example, "*Ullman's Encyclopedia of Industrial Chemistry*", Azo Dyes, 2005 Wiley-VCH Verlag GmbH & Co. KGaA, Weinheim 10.1002/14356007.a03 245, point 3.2; ibid, Textile Auxiliaries, 2002 Wiley-VCH Verlag GmbH & Co. KGaA, Weinheim 10.1002/14356007.a26 227 and "*Ashford's Dictionary of Industrial Chemicals*", Second Edition, p. 14-p. 39, 2001).

The term "anionic direct dyes" means any direct dye comprising in its structure at least one sulfonate group $SO_3^-$ and/or at least one carboxylate group $C(O)O^-$ and/or at least one phosphonate group $P(=O)O^-O^-$ and optionally one or more anionic groups $G^-$ with $G^-$, which may be identical or different, representing an anionic group chosen from alkoxide $O^-$, thioalkoxide $S^-$, phosphonate, carboxylate and thiocarboxylate: $C(Q)Q'^-$ with Q and Q', which may be identical or different, representing an oxygen or sulfur atom; preferably, $G^-$ represents a carboxylate, i.e. Q and Q' represent an oxygen atom.

In formula (Ia) of the invention, the radical $Col^{(-)}m$ represents the anionic part of the "acid dyes" or of the anionic direct dyes that is "derived from" the said acid dyes or from the said anionic direct dyes.

The dyes of the invention derived from direct dyes or acid dyes or from the said anionic direct dyes thus comprise at least one cationic counterion $X^+$ as defined previously.

Preferentially, $Col^{(-)}m$ comprises in its structure:

at least one sulfonate group and at least one (hetero)aryl group, it being understood that at least one sulfonate group is directly bonded to a (hetero)aryl group, preferentially an aryl group such as phenyl or benzo; and optionally one or more anionic groups $G^-$ as defined previously.

According to another preferred embodiment of the invention, $Col^{(-)}m$ comprises in its structure:

at least one carboxylate group and at least one (hetero)aryl group, it being understood that at least one carboxylate group is directly bonded to a (hetero)aryl group, preferentially an aryl group such as phenyl or benzo; and optionally one or more anionic groups $G^-$ as defined previously.

According to yet another preferred embodiment of the invention, $Col^{(-)}m$ comprises in its structure:

at least one phosphonate group and at least one (hetero)aryl group, it being understood that at least one phosphonate group is directly bonded to a (hetero)aryl group, preferentially an aryl group such as phenyl or benzo; and optionally one or more anionic groups $G^-$ as defined previously.

According to one particular embodiment of the invention, the dyes of formula (Ia) are such that m is equal to n.

One variant of the invention concerns the dyes of formula (Ia) for which m and n represent an integer between 1 and 50 and preferably between 1 and 10.

The preferred anionic dyes of formula (Ia) of the invention are chosen from acidic nitro direct dyes, acidic azo dyes, acidic azine dyes, acidic triarylmethane dyes, acidic indoamine dyes, acidic anthraquinone dyes, anionic styryl dyes, and indigoids and acidic natural dyes; each of these dyes containing at least one sulfonate, phosphonate or carboxylate group bearing a cationic counterion $X^+$ as defined previously; preferentially sulfonate or carboxylate of $X^+$.

The optical brighteners (Ib) according to the invention are "derived" from optical brighteners (see, for example, "*Ullman's Encyclopedia of Industrial Chemistry*", Optical Brighteners, 2005 Wiley-VCH Verlag GmbH & Co. KGaA, Weinheim 10.1002/14356007.a18 153, points 2.2 to 2.9).

The term "anionic optical brighteners" means any brightener comprising in its structure at least one sulfonate group $SO_3^-$ and/or at least one carboxylate group $C(O)O^-$ and/or at least one phosphonate group $P(=O)O^-O^-$ and optionally one or more anionic groups $G^-$ with $G^-$, which may be identical or different, representing an anionic group chosen from alkoxide $O^-$, thioalkoxide $S^-$, phosphonate, carboxylate and thiocarboxylate: $C(Q)Q'^-$ with Q and Q', which may be identical or different, representing an oxygen or sulfur atom; preferably, $G^-$ represents a carboxylate, i.e. Q and Q' represent an oxygen atom.

The optical brighteners of the invention (Ib) derived from anionic optical brighteners thus comprise at least one cationic counterion $X^+$ as defined previously.

Preferentially, $Azu^{(-)}m$ comprises in its structure:
- at least one sulfonate group and at least one (hetero)aryl group, it being understood that at least one sulfonate group is directly bonded to a (hetero)aryl group, preferentially an aryl group such as phenyl or benzo; and
- optionally one or more anionic groups $G^-$ as defined previously.

According to another preferred embodiment of the invention, $Azu^{(-)}m$ comprises in its structure:
- at least one carboxylate group and at least one (hetero)aryl group, it being understood that at least one carboxylate group is directly bonded to a (hetero)aryl group, preferentially an aryl group such as phenyl or benzo; and
- optionally one or more anionic groups $G^-$ as defined previously.

According to yet another preferred embodiment of the invention, $Azu^{(-)}m$ comprises in its structure:
- at least one phosphonate group and at least one (hetero)aryl group, it being understood that at least one phosphonate group is directly bonded to a (hetero)aryl group, preferentially an aryl group such as phenyl or benzo; and
- optionally one or more anionic groups $G^-$ as defined previously.

According to one particular embodiment of the invention, the optical brighteners of formula (Ib) are such that m is equal to n.

One variant of the invention concerns the optical brighteners of formula (Ib) for which m and n represent an integer between 1 and 50 and preferably between 1 and 10.

Among the optical brighteners that are most especially suitable for use in the invention, mention may be made of stilbene derivatives, coumarin derivatives, (benz)oxazole derivatives, (benz)imidazole derivatives, (benzo)furan derivatives, pyrazoline derivatives, coumarin derivatives and naphthalimide derivatives.

More particularly, mention may be made of:
the stilbene derivative of naphthotriazole (Tinopal GS from Ciba), 4,4'-distyrylbiphenyl sulfonate (CTFA name: disodium distyrylbiphenyl disulfonate; Tinopal CBS-X from Ciba=sodium 4,4'-bis[(4,6-dianilino-1,3,5-triazin-2-yl)amino]stilbene-2,2'-disulfonate), the cationic derivative of aminocoumarin (Tinopal SWN Conc. from Ciba), diethylaminomethylcoumarin, 4-methyl-7-diethylcoumarin, sodium 4,4'-bis[(4,6-dianilino-1,3,5-triazin-2-yl)amino]stilbene-2,2'-disulfonate (Tinopal SOP from Ciba), 4,4'-bis[(4-anilino-6-bis(2-hydroxyethyl)amino-1,3,5-triazin-2-yl)amino]stilbene-2,2'-disulfonic acid (Tinopal UNPA-GX from Ciba), disodium 4,4'-bis[(4-anilino-6-(2-hydroxyethyl)methylamino-1,3,5-triazin-2-yl)amino]stilbene-2,2'-sulfonate (Tinopal 5BM-GX from Ciba),
the anionic derivative of 2,5-thiophenediylbis(5-tert-butyl-1,3 benzoxazole) (Uvitex OB from Ciba), and
the anionic derivative of diaminostilbene (dispersion in water, Leucophor BSB Liquid from Clariant.

The optical brighteners that may be used in the present invention may thus be in the form of copolymers, for example of acrylates and/or methacrylates, grafted via optical brightener groups and comprising at least one carboxylate group directly bonded to a (hetero)aryl group, preferably an aryl such as phenyl or benzo; and optionally comprising at least one anionic group $G^-$ as defined previously, as described in patent application FR 99/10942.

According to a very advantageous embodiment of the invention, the optical brightener (Ib) is in the presence of a fluorescent dye in particular of formula (Ia) and the said brightener (Ib) is chosen such that the wavelength of the light re-emitted by at least one optical brightener corresponds to the absorption wavelength of at least one fluorescent compound present.

The preferred anionic optical brighteners of formula (Ib) of the invention are chosen from triazine stilbene brighteners, these dyes containing at least one sulfonate, phosphonate or carboxylate group bearing a cationic counterion $X^+$ as defined previously; preferentially a sulfonate of $X^+$.

As anionic dyes of formula (Ia) according to the invention, mention may be made of the dyes of formulae (II), (II'), (III), (III'), (IV), (IV'), (V), (V'), (VI), (VII), (VIII) and (IX), and, as anionic optical brighteners of formula (Ib) according to the invention, mention may be made of the compounds of formulae (X) and (X') below:

a) The Diaryl Anionic Azo Dyes of Formula (II) or (II'):

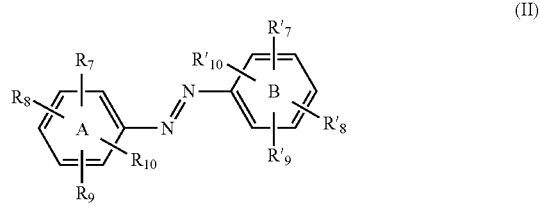

(II)

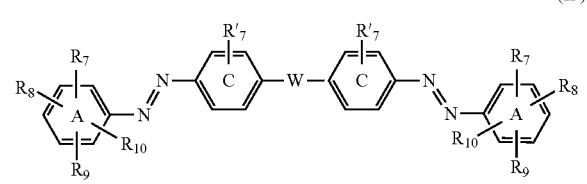

(II')

in which formulae (II) and (II'):
$R_7$, $R_8$, $R_9$, $R_{10}$, $R'_7$, $R'_8$, $R'_9$ and $R'_{10}$, which may be identical or different, represent a hydrogen atom or a group chosen from:
alkyl;
alkoxy, alkylthio;
hydroxyl, mercapto;
nitro;
$R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $X^+$ with $X^+$ as defined previously;
$(O)CO^-$—, $X^+$ with $X^+$ as defined previously;
$(O)P(O_2^-)$—, $2X^+$ with $X^+$ as defined previously;
R"—$S(O)_2$—, with R" representing a hydrogen atom or an alkyl, aryl, (di)(alkyl)amino or aryl(alkyl)amino group; preferentially a phenylamino or phenyl group;
R'''—$S(O)_2$—X'— with R''' representing an alkyl or optionally substituted aryl group, X' as defined previously;
(di)(alkyl)amino;
aryl(alkyl)amino optionally substituted with one or more groups chosen from i) nitro; ii) nitroso; iii) $(O)_2S(O^-)$—, $X^+$ and iv) alkoxy with $X^+$ as defined previously;

optionally substituted heteroaryl; preferentially a benzothiazolyl group;
cycloalkyl; especially cyclohexyl,
Ar—N═N— with Ar representing an optionally substituted aryl group, preferentially a phenyl optionally substituted with one or more alkyl, $(O)_2S(O^-)$—, $X^+$ or phenylamino groups;

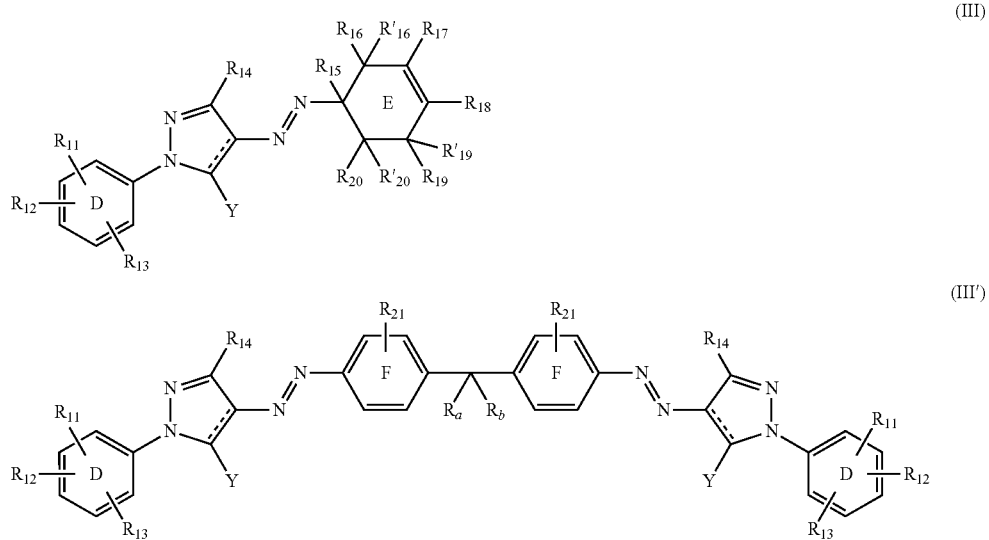

(III)

(III')

or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O^-)$—, $X^+$; iv) hydroxyl; v) mercapto; vi) (di)(alkyl)amino; vii) $R°$—$C(X)$—$X'$—; viii) $R°$—$X'$—$C(X)$—; ix) $R°$—$X'$—$C(X)$—$X''$—; x) Ar—N═N— and xi) optionally substituted aryl(alkyl)amino; with $X^+$, $R°$, X, X', X'' and Ar as defined previously;

W represents a sigma bond σ, an oxygen or sulfur atom, or a divalent radical i) —NR— with R as defined previously, or ii) methylene —$C(R_a)(R_b)$— with $R_a$ and $R_b$, which may be identical or different, representing a hydrogen atom or an aryl group, or alternatively $R_a$ and $R_b$ form, together with the carbon atom that bears them, a spiro cycloalkyl; preferentially W represents a sulfur atom or $R_a$ and $R_b$ together form a cyclohexyl;

it being understood that formulae (II) and (II') comprise at least one sulfonate $(O)_2S(O^-)$—, $X^+$ or phosphonate $(O)P(O_2^-)$ $2X^+$ or carboxylate $(O)C(O^-)$—, $X^+$ radical on one of the rings A, A', B, B' or C with $X^+$ as defined previously;

As examples of dyes of formula (II), mention may be made of the salts derived from: Acid Red 1, Acid Red 4, Acid Red 13, Acid Red 14, Acid Red 18, Acid Red 27, Acid Red 32, Acid Red 33, Acid Red 35, Acid Red 37, Acid Red 40, Acid Red 41, Acid Red 42, Acid Red 44, Acid Red 68, Acid Red 73, Acid Red 135, Acid Red 138, Acid Red 184, Food Red 1, Food Red 13, Food Red 17, Acid Orange 6, Acid Orange 7, Acid Orange 10, Acid Orange 19, Acid Orange 20, Acid Orange 24, Acid Yellow 9, Acid Yellow 36, Acid Yellow 199, Food Yellow 3; Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Pigment Red 57;

and as examples of dyes of formula (II'), mention may be made of the ammonium salts derived from: Acid Red 111, Acid Red 134, Acid yellow 38;

b) The Pyrazolone Anionic Azo Dyes of Formulae (III) and (III'):

in which formulae (III) and (III):
$R_{11}$, $R_{12}$ and $R_{13}$, which may be identical or different, represent a hydrogen or halogen atom, an alkyl group or —$(O)_2S(O^-)$, $X^+$ with $X^+$ as defined previously;
$R_{14}$ represents a hydrogen atom, an alkyl group, a group —$C(O)O^-$, $X^+$ or a phosphonate group $(O)P(O_2^-)$—, $2X^+$ with $X^+$ as defined previously;
$R_{15}$ represents a hydrogen atom;
$R_{16}$ represents an oxo group, in which case $R'_{16}$ is absent, or alternatively $R_{15}$ with $R_{16}$ together form a double bond;
$R_{17}$ and $R_{18}$, which may be identical or different, represent a hydrogen atom or a group chosen from:
$(O)_2S(O^-)$—, $X^+$ with $X^+$ as defined previously;
Ar—O—$S(O)_2$— with Ar representing an optionally substituted aryl group, preferentially a phenyl optionally substituted with one or more alkyl groups;
$R_{19}$ and $R_{20}$ together form either a double bond, or a benzo group D', which is optionally substituted;
$R'_{16}$, $R'_{19}$ and $R'_{20}$, which may be identical or different, represent a hydrogen atom or an alkyl or hydroxyl group;
$R_{21}$ represents a hydrogen atom or an alkyl or alkoxy group;
$R_a$ and $R_b$, which may be identical or different, are as defined previously, preferentially $R_a$ represents a hydrogen atom and $R_b$ represents an aryl group;
Y represents either a hydroxyl group or an oxo group;
---- represents single bond when Y is an oxo group; and represents a double bond when Y represents a hydroxyl group;
it being understood that formulae (III) and (III') comprise at least one sulfonate group $(O)_2S(O^-)$—, $X^+$ on one of the rings D or E or formulae (III) and (III') comprise at least one carboxylate group (O)C(O⁻)—, X⁺ on one of the rings D or E or formulae (III) and (III') comprise at least one phosphonate group (O)P(O₂⁻)—, 2X⁺ on one of the rings D or E with X+ as defined previously; preferentially comprise at least one sulfonate group (O)₂S(O⁻)—, X⁺ on one of the rings D or E;

As examples of dyes of formula (III), mention may be made of the salts derived from: Acid Red 195, Acid Yellow 23, Acid Yellow 27, Acid Yellow 76, and, as examples of dyes of formula (III'), mention may be made of the ammonium salt derived from Acid Yellow 17;

c) The Anthraquinone Dyes of Formulae (IV) and (IV'):

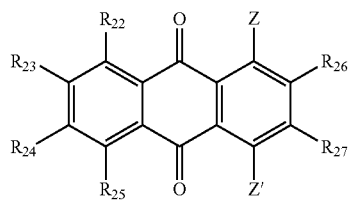

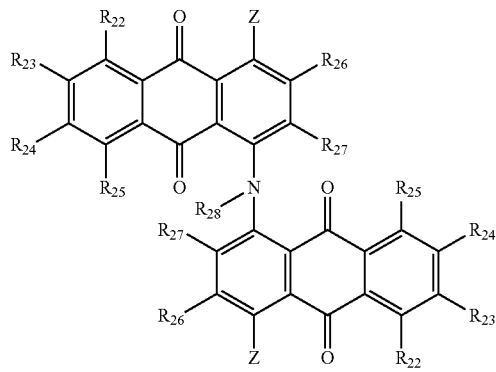

in which formulae (IV) and (IV'):
$R_{22}$, $R_{23}$, $R_{24}$, $R_{25}$, $R_{26}$ and $R_{27}$, which may be identical or different, represent a hydrogen or halogen atom or a group chosen from:
alkyl;
hydroxyl, mercapto;
alkoxy, alkylthio;
aryloxy or arylthio optionally substituted, preferentially substituted with one or more groups chosen from alkyl and (O)₂S(O⁻)—, X⁺ with X⁺ as defined previously;
aryl(alkyl)amino optionally substituted with one or more groups chosen from alkyl and (O)₂S(O⁻)—, X⁺ with X⁺ as defined previously;
(di)(alkyl)amino;
(di)(hydroxyalkyl)amino;
(O)₂S(O⁻)—, X⁺ with X⁺ as defined previously;
Z' represents a hydrogen atom or a group NR₂₈R₂₉ with R₂₈ and R₂₉, which may be identical or different, representing a hydrogen atom or a group chosen from:
alkyl;
polyhydroxyalkyl such as hydroxyethyl;
aryl optionally substituted with one or more groups, particularly i) alkyl such as methyl, n-dodecyl, n-butyl; ii) (O)₂S(O⁻)—, X⁺ with X⁺ as defined previously; iii) R°—C(X)—X'—, R°—X'—C(X)—, R°—X'—C(X)—X"— with R°, X, X' and X" as defined previously, preferentially R° represents an alkyl group;
cycloakyl; especially cyclohexyl;
Z represents a group chosen from hydroxyl and NR'₂₈R'₂₉ with R'₂₈ and R'₂₉, which may be identical or different, representing the same atoms or groups as R₂₈ and R₂₉ as defined previously;
it being understood that formulae (IV) and (IV') comprise at least one sulfonate group (O)₂S(O⁻)—, X⁺ with X⁺ as defined previously;

As examples of dyes of formula (IV), mention may be made of the salts derived from: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3;
and as examples of dyes of formula (IV'), mention may be made of the salt derived from Acid Black 48;

d) The Nitro Dyes of Formulae (V) and (V'):

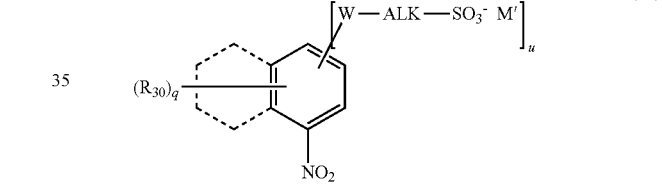

in which formulae (V) and (V'):
$R_{30}$, $R_{31}$ and $R_{32}$, which may be identical or different, represent a hydrogen or halogen atom, or a group chosen from:
alkyl;
alkoxy optionally substituted with one or more hydroxyl groups, alkylthio optionally substituted with one or more hydroxyl groups;
hydroxyl, mercapto;
nitro, nitroso;
(poly)haloalkyl;
R°—C(X)—X'—, R°—X'—C(X)—, R°—X'—C(X)—X"— with R°; X, X' and X" as defined previously;
(O)₂S(O⁻)—, X⁺ with X⁺ as defined previously;
(O)CO⁻—, X⁺ with X⁺ as defined previously;
(di)(alkyl)amino;
(di)(hydroxyalkyl)amino;
heterocycloalkyl such as piperidino, piperazino or morpholino;
in particular, $R_{30}$, $R_{31}$ and $R_{32}$ represent a hydrogen atom;
$R_c$ and $R_d$, which may be identical or different, represent a hydrogen atom or an alkyl group;
W is as defined previously; W particularly represents a group —NH—;
ALK represents a linear or branched divalent $C_1$-$C_6$ alkylene group; in particular, ALK represents a group —CH₂—CH₂—;

n is 1 or 2;
p represents an integer between 1 and 5 inclusive;
q represents an integer between 1 and 4 inclusive;
u is 0 or 1;
when n is 1, J represents a nitro or nitroso group; particularly nitro;
when n is 2, J represents an oxygen or sulfur atom, or a divalent radical —S(O)$_m$— with m representing an integer 1 or 2; preferentially J represents a radical —SO$_2$—;
$M^+$ is as defined previously for $X^+$;

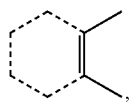

which may be present or absent, represents a benzo group optionally substituted with one or more groups $R_{30}$ as defined previously;
it being understood that formulae (V) and (V') comprise at least one sulfonate group (O)$_2$S(O$^-$)—, $X^+$ or carboxylate group (O)C(O$^-$)—, $X^+$ with $X^+$ as defined previously;

As examples of dyes of formula (V), mention may be made of the salts derived from: Acid Brown 13; Acid Orange 3; as examples of dyes of formula (V'), mention may be made of: Acid Yellow 1, sodium salt of 2,4-dinitro-1-naphthol-7-sulfonic acid, 2-piperidino 5-nitrobenzenesulfonic acid, 2-(4'-N,N(2"-hydroxyethyl)amino-2'-nitro)anilineethanesulfonic acid, 4-β-hydroxyethylamino-3-nitrobenzenesulfonic acid;

d) The Triarylmethane Dyes of Formula (VI):

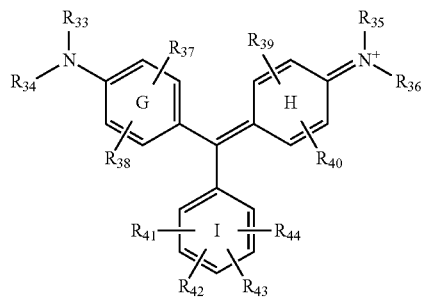

in which formula (VI):
$R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl group and benzyl optionally substituted with a group (O)$_m$S(O$^-$)—, $X^+$ with $X^+$ and m as defined previously;
$R_{37}$, $R_{38}$, $R_{39}$, $R_{40}$, $R'_{41}$, $R'_{42}$, $R'_{43}$ and $R'_{44}$, which may be identical or different, represent a hydrogen atom or a group chosen from:
alkyl;
alkoxy, alkylthio;
(di)(alkyl)amino;
hydroxyl, mercapto;
nitro, nitroso;
$R^\circ$—C(X)—X'—, $R^\circ$—X'—C(X)—, $R^\circ$—X'—C(X)—X"— with $R^\circ$ representing a hydrogen atom or an alkyl or aryl group; X, X' and X", which may be identical or different, representing an oxygen or sulfur atom, or NR with R representing a hydrogen atom or an alkyl group;
(O)$_2$S(O$^-$)—, $X^+$ with $X^+$ as defined previously;
(O)CO$^-$—, $X^+$ with $X^+$ as defined previously;
or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) (O)$_2$S(O$^-$)—, $X^+$; iv) hydroxyl; v) mercapto; vi) (di)(alkyl)amino; vii) $R^\circ$—C(X)—X'—; viii) $R^\circ$—X'—C(X)—; ix) $R^\circ$—X'—C(X)—X"—; with $M^+$, $R^\circ$, X, X', X" as defined previously;
particularly, $R_{37}$ to $R_{40}$ represent a hydrogen atom, and $R_{41}$ to $R_{44}$, which may be identical or different, represent a hydroxyl group or (O)$_2$S(O$^-$)—, $X^+$; and when $R_{43}$ with $R_{44}$ together form a benzo group, it is preferentially substituted with a group (O)$_2$S(O$^-$)—;
it being understood that at least one of the rings G, H, I or I' comprises at least one sulfonate group (O)$_2$S(O$^-$)—, $X^+$ or carboxylate (O)C(O$^-$)—, $X^+$ group;

As examples of dyes of formula (VI), mention may be made of the salts derived from: Acid Blue 1; Acid Blue 3; Acid Blue 7, Acid Blue 9; Acid Violet 49; Acid Green 50;

e) The Xanthene-Based Dyes of Formula (VII):

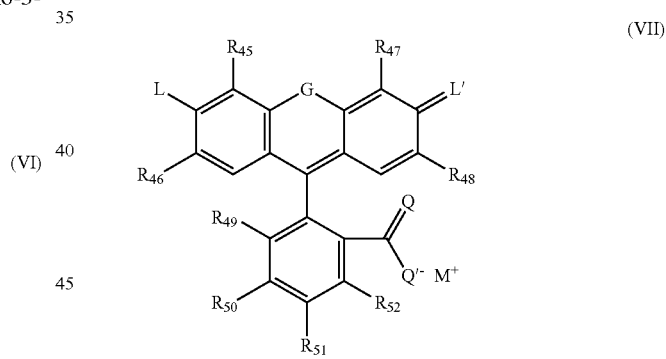

in which formula (VII):
$R_{45}$, $R_{46}$, $R_{47}$ and $R_{48}$, which may be identical or different, represent a hydrogen or halogen atom;
$R_{49}$, $R_{50}$, $R_{51}$ and $R_{52}$, which may be identical or different, represent a hydrogen or halogen atom or a group chosen from:
alkyl;
alkoxy, alkylthio;
hydroxyl, mercapto;
nitro, nitroso;
(O)$_2$S(O$^-$)—, $X^+$ with $X^+$ as defined previously;
(O)CO$^-$—, $X^+$ with $X^+$ as defined previously; particularly $R_{45}$ $R_{46}$, $R_{47}$ and $R_{48}$ represent a hydrogen or halogen atom;
G represents an oxygen or sulfur atom or a group $NR_e$ with $R_e$ as defined previously; particularly G represents an oxygen atom;

L represents an alkoxide O⁻, X⁺; a thioalkoxide S⁻, X⁺ or a group NR$_f$, with R$_f$ representing a hydrogen atom or an alkyl group and X⁺ as defined previously;

L' represents an oxygen or sulfur atom or an ammonium group: N⁺R$_f$R$_g$, with R$_f$ and R$_g$, which may be identical or different, representing a hydrogen atom, an alkyl group, optionally substituted aryl; L' represents particularly an oxygen atom or a phenylamino group optionally substituted with one or more alkyl or (O)$_m$S(O⁻)—, X⁺ groups with m and X⁺ as defined previously;

Q and Q', which may be identical or different, represent an oxygen or sulfur atom; particularly Q and Q' represent an oxygen atom;

X⁺ is as defined previously;

it being understood that formula (VII) comprises at least one sulfonate group (O)$_2$S(O⁻)—, X⁺ or carboxylate group (O)C(O⁻)—, X⁺ with X⁺ as defined previously;

As examples of dyes of formula (VII), mention may be made of the salts derived from: Acid Yellow 73; Acid Red 51; Acid Red 52, Acid Red 87; Acid Red 92; Acid Red 95; Acid Violet 9;

f) The Indole-Based Dyes of Formula (VIII) or (VIII'):

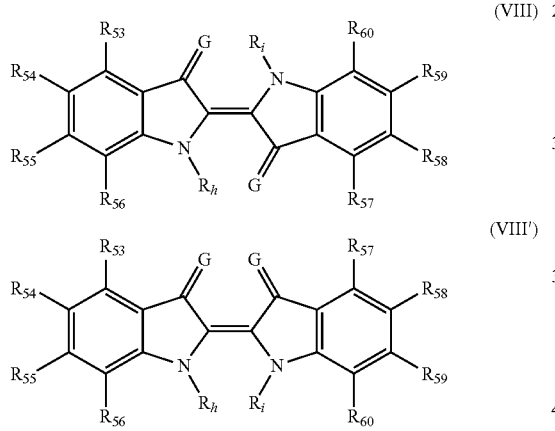

in which formulae (VIII) and (VIII'):

R$_{53}$, R$_{54}$, R$_{55}$, R$_{56}$, R$_{57}$, R$_{58}$, R$_{59}$ and R$_{60}$, which may be identical or different, represent a hydrogen atom or a group chosen from:

alkyl;
alkoxy, alkylthio;
hydroxyl, mercapto;
nitro, nitroso;
R°—C(X)—X'—, R°—X'—C(X)—, R°—X'—C(X)—X"— with R° representing a hydrogen atom or an alkyl or aryl group; X, X' and X", which may be identical or different, representing an oxygen or sulfur atom, or NR with R representing a hydrogen atom or an alkyl group;

(O)$_2$S(O⁻)—, X⁺ with X⁺ as defined previously;
(O)CO⁻—, X⁺ with X⁺ as defined previously;

G represents an oxygen or sulfur atom or a group NR$_e$ with R$_e$ as defined previously; particularly G represents an oxygen atom;

R$_i$ and R$_h$, which may be identical or different, represent a hydrogen atom or an alkyl group;

it being understood that formulae (VIII) and (VIII') comprise at least one sulfonate group (O)$_2$S(O⁻)—, X⁺ or carboxylate group (O)C(O⁻)—, X⁺ with X⁺ as defined previously;

As examples of dyes of formula (VIII), mention may be made of the salt derived from: Acid Blue 74, indigo carmine.

g) The Quinoline-Based Dyes of Formula (IX):

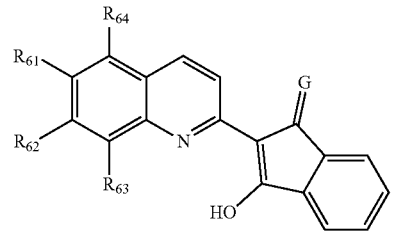

in which formula (IX):

R$_{61}$ represents a hydrogen or halogen atom or an alkyl group;

R$_{62}$, R$_{63}$ and R$_{64}$, which may be identical or different, represent a hydrogen atom or a group (O)$_2$S(O⁻)—, X⁺ with X⁺ as defined previously;

or alternatively R$_{61}$ with R$_{62}$, or R$_{61}$ with R$_{64}$, together form a benzo group optionally substituted with one or more groups (O)$_2$S(O⁻)—, X⁺ with X⁺ as defined previously;

G represents an oxygen or sulfur atom or a group NR$_e$ with R$_e$ as defined previously; particularly G represents an oxygen atom;

it being understood that formula (IX) comprises at least one sulfonate group (O)$_2$S(O⁻)—, X⁺ with X⁺ as defined previously;

As examples of dyes of formula (IX), mention may be made of the salts derived from: Acid Yellow 2, Acid Yellow 3 and Acid Yellow 5.

h) The Stilbene Derivatives of Formulae (X) and (X'):

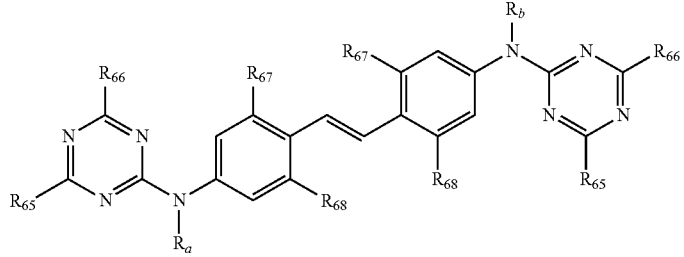

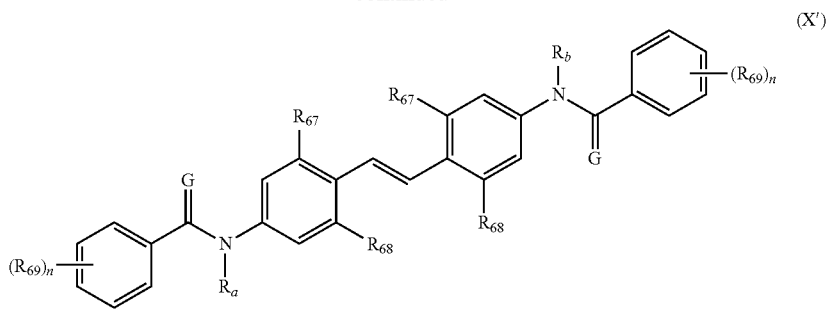

in which formulae (X) and (X'):
- $R_a$ and $R_b$, which may be identical or different, represent a hydrogen atom or a $(C_1\text{-}C_6)$alkyl group;
- $R_{65}$ and $R_{66}$, which may be identical or different, represent a group chosen from:
  - an amino group $NR_hR_i$, in which $R_h$ and $R_i$ represent a hydrogen atom, a $C_1$-$C_6$ alkyl radical optionally substituted with at least one hydroxyl radical, a $C_1$-$C_5$ alkoxy radical, a phenyl radical optionally substituted with at least one hydroxyl group, a group $(O)_2S(O^-)$—, $X^+$ with $X^+$ as defined previously; the radicals $R_hR_i$ possibly a 5- or 6-membered saturated ring optionally containing a heteroatom such as oxygen;
  - a $C_1$-$C_6$ alkoxy group;
  - an aryloxy group such as phenoxy which is not substituted on the aromatic nucleus;
- $R_{67}$ and $R_{68}$, which may be identical or different, represent a hydrogen atom or a group $(O)_2S(O^-)$—, $X^+$ with $X^+$ as defined previously;
- $R_{69}$, which may be identical or different, represent a hydroxyl group or a $C_1$-$C_2$ alkoxy radical;
- G, which may be identical or different, represents an oxygen or sulfur atom or a group $NR_e$ with $R_e$ as defined previously; particularly G represents an oxygen atom;

it being understood that formulae (X) and (X') comprise at least one sulfonate group $(O)_2S(O^-)$—, $X^+$ with $X^+$ as defined previously; preferably, these brighteners comprise as counterion $X^+$ at least one ammonium cation of formula (1) as defined previously, tetrabutylammonium, and/or mixtures thereof.

As examples of optical brighteners of formulae (X) and (X'), mention may be made of salts derived from: Fluorescent Brightener 264, 4,4'-bis[[2,6-bis(p-sulfonatoanilino)-1,3,5-triazin-2-yl]amino]stilbene-2,2'-disulfonate, Fluorescent Brightener 113, Tinopal LPW, Fluorescent Brightener 87, Fluorescent Brightener 85, Fluorescent Brightener 71, Fluorescent Brightener 134, 2,2'-(1,2-ethenediyl)bis(5-(4,6-diphenoxy)-2-(1,3,5-triazinylamino)benzenesulfonic acid, Fluorescent Brightener 251, Fluorescent Brightener 210, Tinopal SFP, Fluorescent Brightener 34, 4,4'-bis[[6-anilino-4-[(2-hydroxyethyl)methylamino]-1,3,5-triazin-2-yl]amino]stilbene-2,2'-disulfonate, 4,4'-bis(2-o-oxyanilino-4-m-sulfoanilino-1,3,5-triazyl-6)stilbene-2,2'-disulfonate.

The optical brighteners preferentially used according to the invention are those derived from sodium 4,4'-bis[(4,6-dianilino-1,3,5-triazin-2-yl)amino]stilbene-2,2'-disulfonate, disodium distyryl-4,4'-biphenylsulfonate or Fluorescent Brightener 71, preferably in which the cationic counterion is an ammonium of formula (1) or (4), for instance tetrabutylammonium, and/or mixtures thereof.

More particularly, the dyes of formulae (II) to (X') that are useful in the invention are chosen from the following salt derivatives:

| | |
|---|---|
| (C.I. 45380) | Acid Red 87 (VII) |
| (C.I. 10316) | salts of 2,4-dinitro-1-naphthol-7-sulfonic acid (V') |
| (C.I. 10383) | Acid Orange 3 (V) |
| (C.I. 13015) | Acid Yellow 9/Food Yellow 2 (II) |
| (C.I. 14780) | /Direct Red 45/Food Red 13 (II) |
| (C.I. 13711) | Acid Black 52 (II) |
| (C.I. 13065) | Acid Yellow 36 (II) |
| (C.I. 14700) | salt of 1-hydroxy-2-(2',4'-xylyl-5-sulfonatoazo)-naphthalene-4-sulfonic acid/Food Red 1 (II) |
| (C.I. 14720) | Acid Red 14/Food Red 3/Mordant Blue 79 (II) |
| (C.I. 14805) | salt of 4-hydroxy-3-[(2-methoxy-5-nitrophenyl)diaza]-6-(phenylamino)naphthalene-2-sulfonic acid/Acid Brown 4 (II) |
| (C.I. 15510) | Acid Orange 7/Pigment Orange 17/Solvent Orange 49 (II) |
| (C.I. 15985) | Food Yellow 3/Pigment Yellow 104 (II) |
| (C.I. 16185) | Acid Red 27/Food Red 9 (II) |
| (C.I. 16230) | Acid Orange 10/Food Orange 4 (II) |
| (C.I. 16250) | Acid Red 44 (II) |
| (C.I. 17200) | Acid Red 33/Food Red 12 (II) |
| (C.I. 15685) | Acid Red 184 (II) |
| (C.I. 19125) | Acid Violet 3 (II) |
| (C.I. 18055) | salt of 1-hydroxy-2-(4'-acetamidophenylazo)-8-acetamidonaphthalene-3,6-disulfonic acid/Acid Violet 7/Food Red 11 (II) |

-continued

| | |
|---|---|
| (C.I. 18130) | Acid Red 135 (II) |
| (C.I. 19130) | Acid Yellow 27(III) |
| (C.I. 19140) | Acid Yellow 23/Food Yellow 4 (III) |
| (C.I. 20170) | 4'-(sulfonato-2″,4″-dimethyl)bis(2,6-phenylazo)-1,3-dihydroxybenzene/ Acid Orange 24 (II) |
| (C.I. 20470) | salt of 1-amino-2-(4'-nitrophenylazo)-7-phenylazo-8-hydroxynaphthalene-3,6-disulfonic acid/Acid Black 1 (II) |
| (C.I. 23266) | (4-((4-methylphenyl)sulfonyloxy)phenylazo)-2,2'-dimethyl-4-((2-hydroxy-5,8-disulfonato)naphthylazo)biphenyl/Acid Red 111 (II') |
| (C.I. 27755) | Food Black 2 (II) |
| (C.I. 25440) | 1-(4'-sulfonatophenylazo)-4-((2″-hydroxy-3″-acetylamino-6″,8″-disulfonato)naphthylazo)-6-sulfonatonaphthalene (tetrasodium salt)/Food Black 1 (II) |
| (C.I. 42090) | Acid Blue 9 (VI) |
| (C.I. 60730) | Acid Violet 43 (IV) |
| (C.I. 61570) | Acid Green 25 (IV) |
| (C.I. 62045) | salt of 1-amino-4-cyclohexylamino-9,10-anthraquinone-2-sulfonic acid/ Acid Blue 62 (IV) |
| (C.I. 62105) | Acid Blue 78 (IV) |
| (C.I. 14710) | salt of 4-hydroxy-3-((2-methoxyphenyl)azo)-1-naphthalenesulfonic acid/ Acid Red 4 (II) |
| | 2-piperidino-5-nitrobenzenesulfonic acid (V') |
| | 2-(4'-N,N-(2″-hydroxyethyl)amino-2'-nitro)anilineethanesulfonic acid (V') |
| | 4-β-hydroxyethylamino-3-nitrobenzene sulfonic acid (V') |
| (C.I. 42640) | Acid Violet 49 (VI) |
| (C.I. 42080) | Acid Blue 7 (VI) |
| (C.I. 58005) | salts of 1,2-dihydroxy-3-sulfoanthraquinone/Mordant Red 3 (IV) |
| (C.I. 62055) | salt of 1-amino-9,10-dihydro-9,10-dioxo-4-(phenylamino)-2-anthracenesulfonic acid/Acid Blue 25 (IV) |
| (C.I. 14710) | salt of 4-hydroxy-3-((2-methoxyphenyl)azo)-1-naphthalenesulfonic acid/ Acid Red 4 (II) |
| (C.I. 47005) | Acid Yellow 3 (IX) |
| (C.I. 16035) | Food Red 17 (II) |
| (C.I. 16255) | Acid Red 18 (II) |
| (C.I. 45100) | Acid Red 52 (VII) |
| (C.I. 15850) | Pigment Red 57 (II) |
| (C.I. 45410) | Acid Red 92 (VII) |
| (C.I. 75781) | Acid blue 74 (VIII) |
| (C.I. 73020) | salt of indigotetrasulfonic acid (VIII) |
| (C.I. 40623) | Fluorescent Brightener 264 (X) |
| (CI 40622) | Tinopal LPW (X) |
| (C.I. Fluorescent Brightener 87) | Fluorescent Brightener 87 (X) |
| C.I. 406225 | Fluorescent Brightener 85 (X) |
| (C.I. Fluorescent Brightener 71) | Fluorescent Brightener 71 (X) |
| (C.I. Fluorescent Brightener 134) | Fluorescent Brightener 134 (X) |
| | 2,2'-(1,2-ethenediyl)bis(5-(4,6-diphenoxy)-2-(1,3,5-triazinylamino)benzenesulfonic acid (X) |
| (C.I. Fluorescent Brightener 251) | Fluorescent Brightener 251 (X) |
| (C.I. Fluorescent Brightener 210) | Fluorescent Brightener 210 (X) |
| | Tinopal SFP (X) Fluorescent Brightener 34 (X') |
| | 4,4'-bis[[6-anilino-4-[(2-hydroxyethyl)methylamino]-1,3,5-triazin-2-yl]amino]stilbene-2,2'-disulfonate acid (X) |
| | 4,4'-bis(2-o-oxyanilino-4-m-sulfoanilino-1,3,5-triazyl-6)stilbene-2,2'-disulfonate acid (X) |

Most of these dyes are described in particular in the *Colour Index* published by The Society of Dyers and Colourists, P.O. Box 244, Perkin House, 82 Grattan Road, Bradford, Yorkshire, BD1 2JB England.

The anionic dyes and anionic optical brighteners according to the invention may be obtained by exchanging the cationic counterion with one or more cationic counterions of the type $X^+$ with $X^+$ as defined previously.

The anionic dyes most particularly preferred whose cationic counterions may be replaced are the dyes designated in the Colour Index under the code C.I. 58005 (monosodium salt of 1,2-dihydroxy-9,10-anthraquinone-3-sulfonic acid), C.I. 60730 (monosodium salt of 2-[(9,10-dihydro-4-hydroxy-9,10-dioxo-1-anthracenyl)amino]-5-methylbenzenesulfonic acid), C.I. 15510 (monosodium salt of 4-[(2-hydroxy-1-naphthyl)azo]benzenesulfonic acid), C.I. 15985 (disodium salt of 6-hydroxy-5-[(4-sulfophenyl)azo]-2-naphthalenesulfonic acid), C.I. 17200 (disodium salt of 5-amino-4-hydroxy-3-(phenylazo)-2,7-naphthalenedisulfonic acid), C.I. 20470 (disodium salt of 1-amino-2-(4'-nitrophenylazo)-7-phenylazo-8-hydroxy-3,6-naphthalenedisulfonic acid), C.I. 42090 (disodium salt of N-ethyl-N-[4-[[4-[ethyl[3-sulfophenyl)methyl]amino]phenyl](2-sulfophenyl)methylene]-2,5-cyclohexadien-1-ylidene]-3-sulfobenzenemethanaminium hydroxide, inner salt), C.I. 61570 (disodium salt of 2,2'-[(9,10-dihydro-9,10-dioxo-1,4-anthracenediyl)diimino]bis[5-methyl]-benzenesulfonic acid).

It is also possible to use compounds corresponding to the mesomeric or tautomeric forms of structures (II) to (X').

More preferentially, the anionic compounds of formula (Ia) according to the invention are chosen from those of formulae (II), (III), (IV), (VI), (VII), (VII), (VIII') and (IX).

According to a particular embodiment of the invention, the dyes are chosen from (IIa), (IIIa) and (IVa) below:

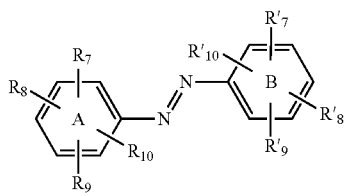
(IIa)

in which formula (IIa):
R$_7$, R$_8$, R$_9$, R$_{10}$, R'$_7$, R'$_8$, R'$_9$ and R'$_{10}$, which may be identical or different, represent a hydrogen atom or a group chosen from:
hydroxyl;
nitro, nitroso;
(di)(alkyl)amino;
(O)$_2$S(O$^-$)—, M$^+$ with M$^+$ representing a hydrogen atom or a cationic counterion or X$^+$ as defined previously; and
Ar—N=N— with Ar representing an optionally substituted aryl group, preferentially a phenyl optionally substituted with one or more alkyl or (O)$_2$S(O$^-$)—, M$^+$ groups;
or alternatively two contiguous groups R$_7$ with R$_8$ or R$_8$ with R$_9$ or R$_9$ with R$_{10}$ together form a fused benzo group A'; and R'$_7$ with R'$_8$ or R'$_8$ with R'$_9$ or R'$_9$ with R'$_{10}$ together form a fused benzo group B'; with A' and B' optionally substituted with one or more groups chosen from a) (O)$_2$S(O$^-$)—, M$^+$; b) hydroxyl; c) Ar—N=N—; with M$^+$ and Ar as defined previously;
it being understood that formula (IIa) comprises at least one sulfonate radical (O)$_2$S(O$^-$)—, X$^+$ on one of the rings A, A', B, B' with R$_1$R$_2$R$_3$R$_4$ as defined previously; preferentially tetrabutylammonium sulfonate;

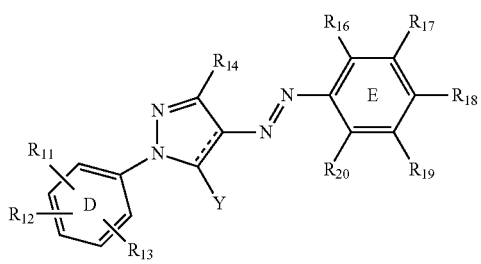
(IIIa)

in which formula (IIIa):
R$_{11}$, R$_{12}$ and R$_{13}$, which may be identical or different, represent a hydrogen or halogen atom, an alkyl group or —(O)$_2$S(O$^-$), M$^+$ with M$^+$ as defined previously;
R$_{14}$ represents a hydrogen atom, an alkyl group or a group —C(O)O—, M$^+$ with M$^+$ as defined previously;
R$_{16}$, R$_{17}$, R$_{18}$, R$_{19}$ and R$_{20}$, which may be identical or different, represent a hydrogen atom, an alkyl or hydroxyl group or (O)$_2$S(O$^-$)—, M$^+$ with M$^+$ as defined previously;
Y represents either a hydroxyl group or an oxo group;
---- represents a single bond when Y is an oxo group; and represents a double bond when Y represents a hydroxyl group;
it being understood that formula (IIIa) comprises at least one sulfonate group (O)$_2$S(O$^-$)—, X$^+$ on one of the rings D or E or carboxylate (O)C(O$^-$)—, X$^+$ as defined previously; preferentially X$^+$ sulfonate;

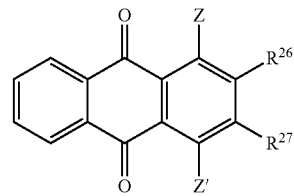
(IVa)

in which formula (IVa):
Z' represents a group NR$_{28}$R$_{29}$ with R$_{28}$ representing a hydrogen atom or an alkyl group and R$_{29}$ representing i) an aryl group optionally substituted particularly with one or more groups chosen from i) alkyl such as methyl and ii) (O)$_2$S(O$^-$)—, M$^+$ with M$^+$ as defined previously or ii) a cycloalkyl group; especially cyclohexyl;
Z represents a group chosen from hydroxyl and NR'$_{28}$R'$_{29}$ with R'$_{28}$ and R'$_{29}$, which may be identical or different, representing the same atoms or groups as R$_{28}$ and R$_{29}$ as defined previously;
R$^{26}$ and R$^{27}$, which may be identical or different, represent a hydrogen atom or a sulfonate group (O)$_2$S (O$^-$)—, X$^+$ with X$^+$ as defined previously;
it being understood that formulae (IVa) comprises at least one sulfonate group (O)$_2$S(O$^-$)—, X$^+$ with X$^+$ as defined previously; preferentially X$^+$ sulfonate.

Examples that may be mentioned include the following anionic dyes:

| Anionic part "derived" from a commercial dye | Corresponding structures |
| --- | --- |
| Acid Orange 7 | 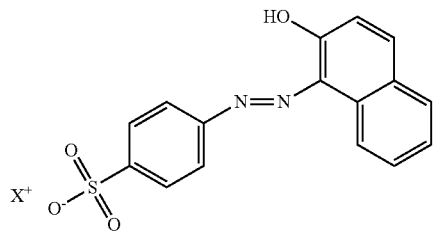 |
| | (belongs to formulae (II) and (IIa)) |

-continued
| Anionic part "derived" from a commercial dye | Corresponding structures |
|---|---|
| Acid Black 1 | 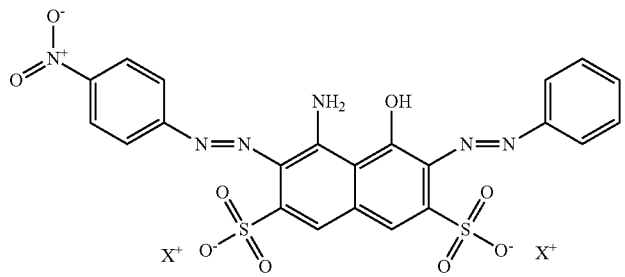<br>(belongs to formulae (II) and (IIa)) |
| Acid Red 33 | 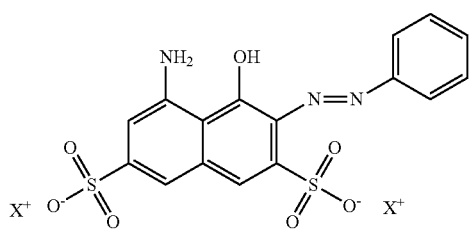<br>(belongs to formulae (II) and (IIa)) |
| Acid Red 18 | 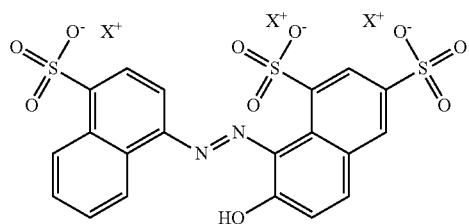<br>(belongs to formulae (II) and (IIa)) |
| Food Red 17 | 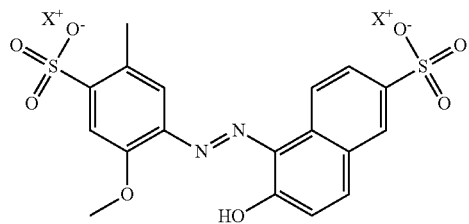<br>(belongs to formulae (II) and (IIa)) |
| Pigment Red 57 | 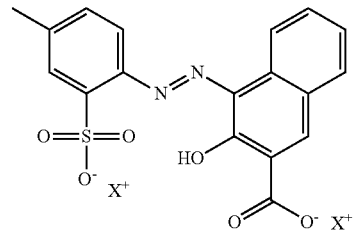<br>(belongs to formulae (II) and (IIa)) |

-continued
| Anionic part "derived" from a commercial dye | Corresponding structures |
|---|---|
| Acid Yellow 23 | 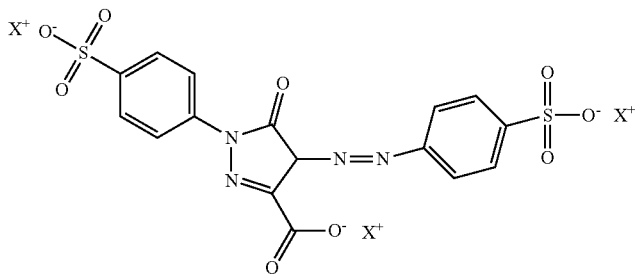 (belongs to formulae (III) and (IIIa)) |
| Acid Violet 43 | 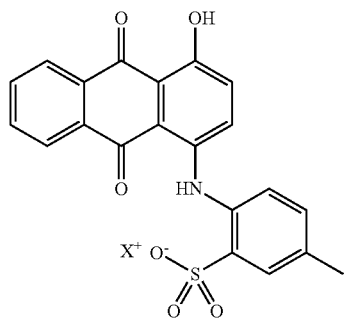 (belongs to formulae (IV) and (IVa)) |
| Acid Green 25 | 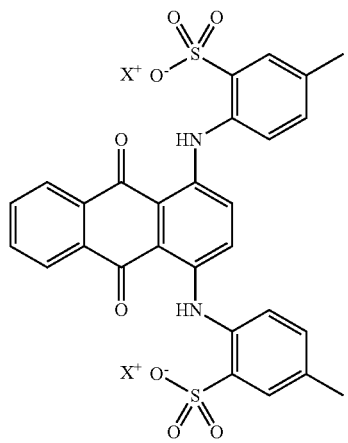 (belongs to formulae (IV) and (IVa)) |
| Acid Blue 62 | 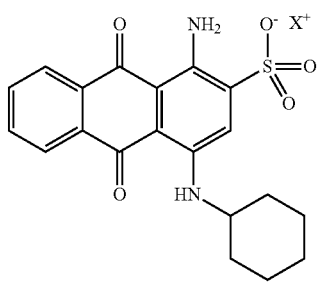 (belongs to formulae (IV) and (IVa)) |

-continued
| Anionic part "derived" from a commercial dye | Corresponding structures |
|---|---|
| Acid Blue 9 | 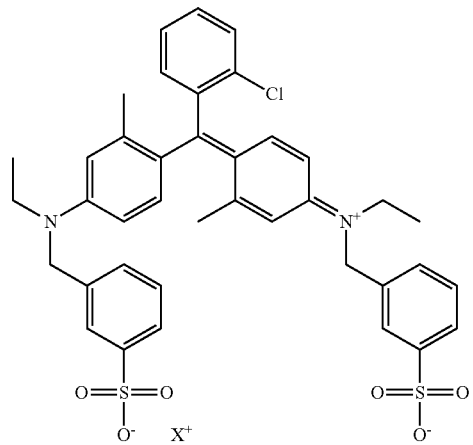<br>(belongs to formula (VI)) |
| Acid Red 52 | 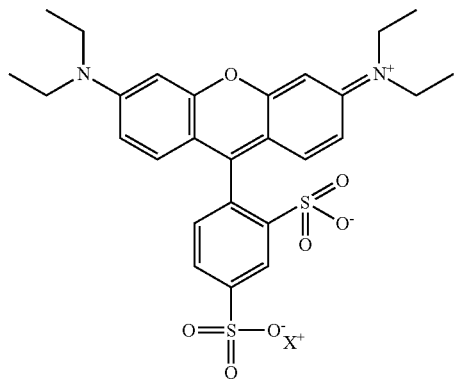<br>(belongs to formula (VII)) |
| Indigo disulfonate | 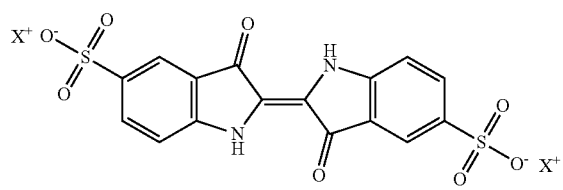<br>(belongs to formula (VIII)) |
| Indigo carmine | 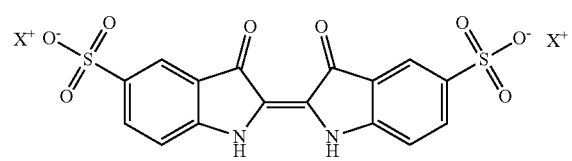<br>(belongs to formula (VIII')) |

-continued

| Anionic part "derived" from a commercial dye | Corresponding structures |
|---|---|
| Acid Yellow 3 | 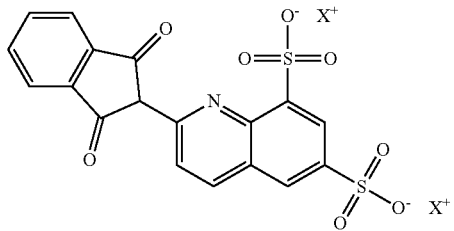<br>(belongs to formula (IX)) |
| Fluorescent brightener 71 | 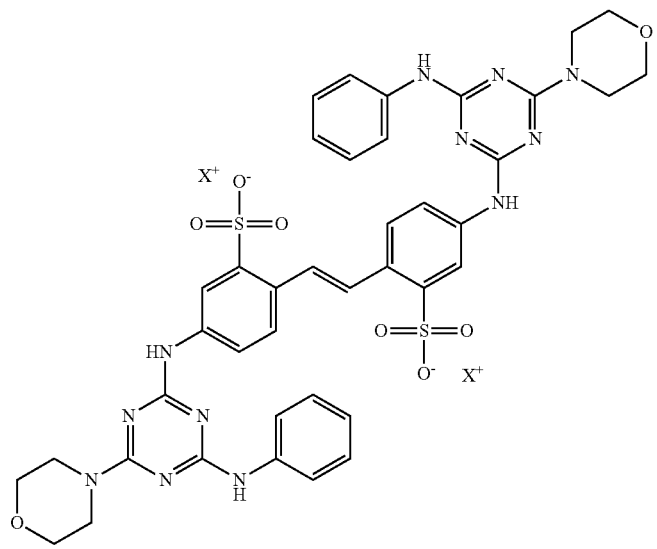<br>(belongs to formula (X)) | with $X^+$, which may be identical or different, as defined previously, when the part Col- or Azu-comprises several anionic charges (m=2 or 3) then $2X^+$ or $3X^+$ may correspond to a dication or trication as defined previously.

The dyes of formula (Ia) are derived from anionic dyes that are either commercially available or available via synthesis using standard synthetic techniques known to those skilled in the art. This is likewise the case for the optical brighteners of formula (Ib). The "known" dyes and brighteners comprise a cationic counterion that is generally mineral (alkali metal or alkaline-earth metal cation) which is replaced with an organic counterion $X^+$ as defined previously. This substitution of cationic counterions may be performed via a standard ion-exchange method, for example by ion-exchange resin or ion-exchange column (ion-exchange methodology: see, for example, http://www.sigmaaldrich.com/analytical-chromatography/sample-preparation/spe/ionexchange-methodology.html and "*Ion Exchange Material—Properties and Applications*", Andrei. A. Zagorodni, 1st Ed. 2007, Oxford, Elsevier BV; "Ion Exchange", H. Friedrich G, 1995, NY: MacGraw-Hill, chapt. 2.3 p. 12: Ion Exchange Resins, chapt. 3, p. 29: Cation Exchangers; Chapt. 9, p. 421: Ion Exchange Column; *Ullmann's Encyclopedia of Industrial Chemistry* "Ion Exchange" F. Dardel and Thomas V. Arden, Published Online: 15/04/2008, DOI: 10.1002/14356007.a14_393.pub2; *Kirk-Othmer Encyclopedia of Chemical Technology*, "Ion Exchange" C. Dickert, Published Online: 4/12/2000, DOI: 10.1002/0471238961.09151404090311.a01)

Another method consists in dissolving the known anionic dye in a water-immiscible organic solvent, such as halogenated organic solvents, for instance dichloromethane, chloroform or methyl tetrachloride, or aromatic organic solvents such as toluene, tetrahydrofuran (THF) or methyltetrahydrofuran (MeTHF), and in adding thereto an aqueous solution comprising salts of $X^+$.

Depending on the added amount of salt of $X^+$ in the aqueous solution and of the number of sulfonate, phosphonate or carboxylate anionic groups, it is possible to replace one or more cationic counterions. If, for example, all of the cationic counterions must be replaced, then it is chosen to use an aqueous solution saturated with salt of $X^+$. The resulting mixture (aqueous solution+salt of $X^+$+organic solvent+"known" anionic dye) is then left stirring at room temperature for between 1 minute and one week, such as from 30 minutes to 48 hours, in particular one day and preferentially between 2 and 4 hours. Next, the organic phase is separated from the aqueous phase (by settling) and then optionally washed and separated again (by settling). The organic phase is optionally dried using a standard drying agent such as alkali metal or alkaline-earth metal sulfate salts such as sodium sulfate, and is then filtered. The starting organic solvent is then evaporated off, for example using a rotary evaporator of Rotavapor® type.

II. Composition Comprising at least One Anionic Dye of Formula (Ia) and/or at least One Optical Brightener of Formula (Ib)

Another subject of the invention is a composition comprising, in a cosmetic medium, at least one anionic dye of formula (Ia) and/or at least one optical brightener of formula (Ib) as defined previously.

According to a particularly advantageous mode of the invention, the cosmetic composition comprising one or more compounds of formula (Ia) and/or (Ib) does not contain any chemical oxidizing agent.

The term "chemical oxidizing agent" means any chemical or enzymatic oxidizing agent other than atmospheric oxygen.

The dye composition that is useful in the invention generally contains an amount of dye of formula (Ia) and/or (Ib) (in total when (Ia) and (Ib) are together) of between 0.001% and 50% relative to the total weight of the composition. Preferably, this amount is between 0.005% and 20% by weight and even more preferentially between 0.01% and 5% by weight relative to the total weight of the composition.

The dye composition may also contain additional direct dyes other than those of formula (Ia). These direct dyes are chosen, for example, from neutral, anionic or cationic nitrobenzene direct dyes, neutral, anionic or cationic azo direct dyes, tetraazapentamethine dyes, neutral, anionic or cationic quinone and in particular anthraquinone dyes, azine direct dyes, triarylmethane direct dyes, indoamine direct dyes and natural direct dyes.

Among the natural direct dyes, mention may be made of lawsone, juglone, alizarin, purpurin, carminic acid, kermesic acid, purpurogallin, protocatechaldehyde, indigo, isatin, curcumin, spinulosin and apigenidin. Use may also be made of extracts or decoctions comprising these natural dyes and especially henna-based poultices or extracts.

The dye composition may contain one or more oxidation bases and/or one or more couplers conventionally used for the dyeing of keratin fibres.

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols, naphthalene couplers and heterocyclic couplers, and the addition salts thereof.

The coupler(s) are each generally present in an amount of between 0.001% and 10% by weight and preferably between 0.005% and 6% by weight relative to the total weight of the dye composition.

The oxidation base(s) present in the dye composition are each generally present in an amount of between 0.001% and 10% by weight and preferably between 0.005% and 6% by weight relative to the total weight of the dye composition.

In general, the addition salts of the oxidation bases and couplers which may be used in the context of the invention are especially chosen from the salts of addition with an acid, such as the hydrochlorides, hydrobromides, sulfates, citrates, succinates, tartrates, lactates, tosylates, benzenesulfonates, phosphates and acetates, and the salts of addition with a base, such as alkali metal hydroxides, for instance sodium hydroxide, potassium hydroxide, ammonia, amines or alkanolamines.

The medium that is suitable for dyeing, also known as the dye support, is a cosmetic medium generally formed from water or a mixture of water and of at least one organic solvent. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

When they are present, the solvents are preferably present in proportions preferably of between 1% and 99% by weight approximately and even more preferentially between 5% and 95% by weight approximately relative to the total weight of the dye composition.

The dye composition may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones such as amino silicones, film-forming agents, ceramides, preserving agents, opacifiers and conductive polymers.

The above adjuvants are generally present in an amount for each of them of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

The pH of the dye composition is generally between 3 and 14 approximately, preferably between 4 and 11 approximately and more particularly between 5 and 10. It may be adjusted to the desired value by means of acidifying or basifying agents usually used in the dyeing of keratin fibres, or alternatively using standard buffer systems.

Among the acidifying agents that may be mentioned, for example, are mineral or organic acids such as those chosen from: i) hydrochloric acid HCl, ii) hydrobromic acid HBr, iii) sulfuric acid $H_2SO_4$, iv) alkylsulfonic acids: Alk-S$(O)_2$OH such as methanesulfonic acid and ethanesulfonic acid; v) arylsulfonic acids: Ar—$S(O)_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3COOH$; xiv) triflic acid $CF_3SO_3H$; and xv) tetrafluoroboric acid $HBF_4$.

They are more particularly chosen from hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include mineral and organic bases, more particularly ammonia, alkali metal carbonates, alkanolamines, such as mono-, di- and triethanolamines and derivatives thereof, sodium hydroxide, potassium hydroxide and the compounds of formula (γ) below:

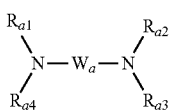
(γ)

in which formula (γ):
- $W_a$ is a $(C_1$-$C_{10})$alkylene radical, optionally substituted with a hydroxyl group or a $C_1$-$C_4$ alkyl radical and/or optionally interrupted with one or more heteroatoms such as O or N; preferentially, W is a propylene;
- $R_{a1}$, $R_{a2}$, $R_{a3}$ and $R_{a4}$, which may be identical or different, represent a hydrogen atom or a $C_1$-$C_4$ alkyl or $C_1$-$C_4$ hydroxyalkyl radical.

The dye composition may be in various forms, such as in the form of a liquid, a cream or gel, or in any other form that is suitable for dyeing keratin fibres, and especially the hair.

III. Dyeing and/or Lightening Process Using an Anionic Dye of Formula (Ia) and/or (Ib)

Another subject of the invention is a process for treating keratin fibres, which consists in applying to the said fibres a composition comprising at least one anionic dye of formula (Ia) and/or an optical brightener of formula (Ib) as defined previously. The treatment process according to the invention may make it possible to optically lighten keratin fibres, especially dark keratin fibres such as keratin fibres with a tone depth of less than or equal to 6 and particularly less than or equal to 4, by using a composition comprising at least one fluorescent anionic dye of formula (Ia), which are preferentially dyes in the orange range. Mention may be made particularly of the xanthene-based fluorescent dyes (VII) as defined previously, especially the ammonium derivatives of: Acid Yellow 73; Acid Red 51; Acid Red 87 and Acid Red 92. According to a particularly advantageous embodiment of the invention, the dyeing or optical lightening process does not involve any chemical oxidizing agent. These dyes may be combined with optical brighteners of formula (Ib). The optical brighteners preferentially used according to the invention are those derived from sodium 4,4'-bis[(4,6-di-anilino-1,3,5-triazin-2-yl)amino]stilbene-2,2'-disulfonate, disodium distyryl-4,4'-biphenyl sulfonate or the Fluorescent Brightener 71, preferably in which the cationic counterion is an ammonium of formula (1), such as tetrabutylammonium, and/or mixtures thereof.

According to one variant of the dyeing process, once the composition containing at least one anionic compound of formula (Ia) and/or (Ib) is applied to the keratin fibres, the composition is left on for a certain amount of time, and the keratin fibres are then rinsed and/or drained dry and then air-dried or dried using a hairdryer. The duration of the treatment after application of the composition containing at least one compound of formula (Ia) and/or (Ib) may be short, for example from 0.1 second to 1 hour, particularly between 5 minutes and 50 minutes and more particularly between 10 and 45 minutes, and preferentially the leave-on time is 30 minutes.

The examples that follow serve to illustrate the invention without, however, being limiting in nature.

The anionic compounds of the examples hereinbelow were fully characterized by the standard spectroscopic and spectrometric methods.

EXAMPLE OF PREPARATION

General Preparation of the Dyes of the Invention: Counterion Exchange

A "known" anionic compound containing an alkali metal counterion such as sodium is suspended in dichloromethane. Water saturated with tetrabutylammonium hydrogen sulfate is then added (equivalent volume), and the mixture is then stirred for 3 hours at room temperature. The organic phase is recovered and then washed several times with distilled water to remove the traces of starting dye. The organic phase is then dried with sodium sulfate, filtered and then evaporated to dryness. Powders are obtained. The analyses are in accordance with the expected structures. The compounds synthesized are below:

Preparation of Compound (B)

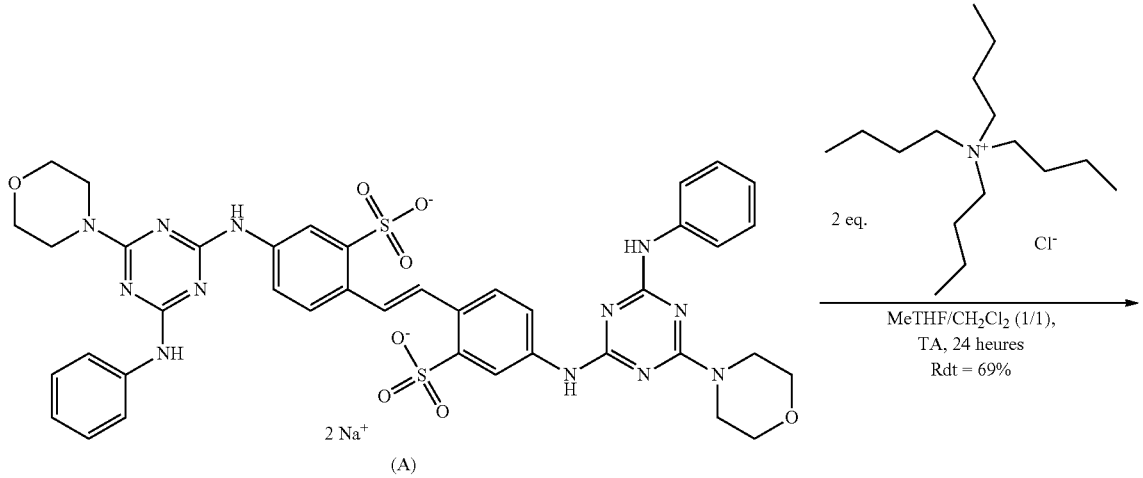

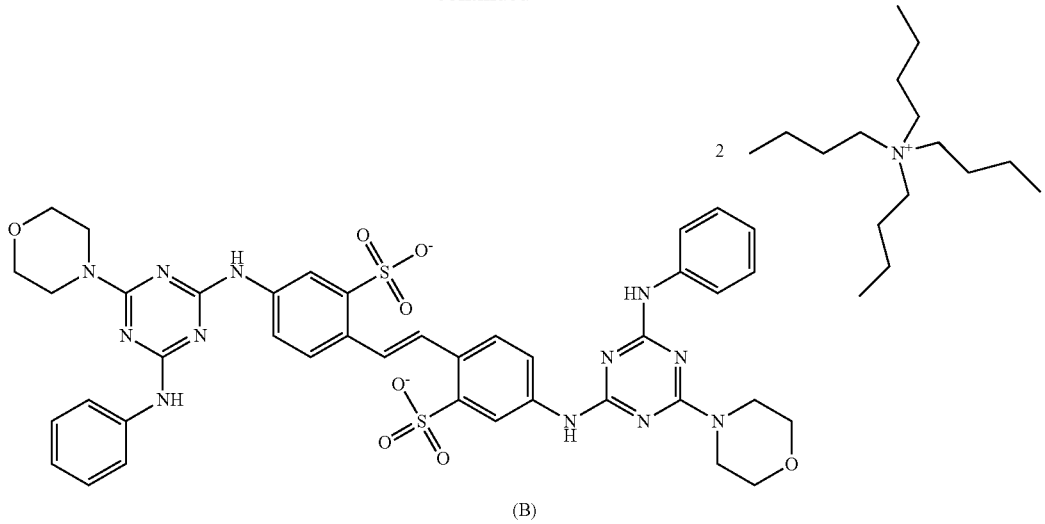

(B)

10 g of Fluorescent Brightener 71 are suspended in a mixture consisting of 150 ml of dichloromethane/150 ml of THF in the presence of two equivalents of tetrabutylammonium chloride, in a conical flask. The reaction medium is stirred for 48 hours at room temperature and then filtered. The filtrate is then cleaned twice with water. The analyses performed confirm the structure of the product obtained.

Dyeing Hair Example

Example 1

409 mg (5×10$^{-3}$ mol %) of compound (B) is solubilized in a mixture containing water (1 ml), benzyl alcohol (4 ml), ethanol (1 ml) with sonication in a warm bath (40° C.) for 35 minutes. 2 ml of slightly colored solution is applied on one lock of keratin fibers (1 g, Caucasian White natural hair 90%, Caucasian natural hair of tone height HT4, and Japanese hair of tone height HT=2). After locks are rinced with lukewarm water, and dried for 10 minutes. The compound (A) is applied under the same condition. Colorimetric measurement are realized with the aid of spectrocolorimeter Konica, 24 hours after dyeing treatment.

Color Evaluation on Keratin Fibers

The colour of the hair was determined by using the L*a*b* system, with a Konica spectrophotometer.

According to this system, L* indicates the lightness. The lowest is the value of L*, the most intense is the color of the hair. The chromaticity coordinates are expressed by the parameters a* and b*, a* indicating the axis of red/green shades and b* the axis of yellow/blue shades.

The results are expressed in the following table.

ΔE, which is the color variation between or uptake a colored lock and a colored lock after shampoos, is obtained from the following formula:

$$\Delta E = \sqrt{(L^*-L_o^*)^2+(a^*-a_o^*)^2+(b^*-b_o^*)^2}$$

wherein L* indicates lightness and a* and b* are the chromaticity coordinates of the colored locks after hair dyeing step whereas $L_o^*$ indicates the lightness and $a_o^*$ et $b_o^*$ are the initial color of the locks of undyed hair. The highest is the value of ΔE, the most uptake fluorescence or colour on the hair.

On Caucasian 90% White Natural Hair:

brightening effect of anionic dyes with cationic counter-ion according to the invention vs. same anionic dyes with cationic metal (sodium, out of the invention)

ΔE*, is the color variation or uptake between a colored lock and a uncolored lock (reference) with compound of the invention, obtained from the following formula:

$$\Delta E^* = \sqrt{(L^*-L_o^*)^2+(a^*-a_o^*)^2+(b^*-b_o^*)^2}$$

wherein L* indicates lightness and a* and b* are the chromaticity coordinates of the colored locks after hair dyeing step whereas $L_o^*$ indicates the lightness and $a_o^*$ et $b_o^*$ are the initial color of the locks of undyed hair. The higest is the value of ΔE*, the most visual lightening effect is the color of the hair.

TABLE 1

| | L* | a* | b* | ΔE* |
|---|---|---|---|---|
| Before dyeing hair (reference) | 53.95 | 0.72 | 14.63 | 1.52 |
| After dyeing hair with dye out of the invention (sodium) (A) | 55.13 | 0.12 | 14.28 | |

TABLE 2

| | L* | a* | b* | ΔE* |
|---|---|---|---|---|
| Before dyeing hair (reference) | 53.95 | 0.72 | 14.63 | 3.36 |
| After dyeing hair with compound (B) according to the invention | 52.99 | 0.82 | 11.41 | |

Composition containing compound (B) fold the yellow shade (b* data are significantly lower than the untreated hair (reference)) (ΔE=3.36) more efficiently than comparative compound bearing a sodium counter cation (see b* data and ΔE* which are higher than composition which contains compound (A) (reference)).

Moreover the exchange of the counter anion exarcerbates the fuorescence property on hair i.e. the lightening effect.

The invention claimed is:

1. A method for treating keratin fibres comprising applying a cosmetic composition to said fibers, said composition comprising:

at least one compound chosen from anionic compounds of formula (Ia) and formula (Ib):

$$Col^{(-)}{}_m[X^+]_n \qquad (Ia)$$

$$Azu^{(-)}{}_m[X^+]_n \qquad (Ib)$$

optical isomers, geometrical isomers, and solvates thereof; wherein:

Col$^{(-)}$ represents the anionic part of an anionic direct dye comprising m anionic charges chosen from acidic nitro direct dyes, acidic azo dyes, acidic azine dyes, acidic triarylmethane dyes, acidic indoamine dyes, acidic anthraquinone dyes, anionic styryl dyes, indigoids, or acidic natural dyes;

Azu$^{(-)}$ represents the anionic part of an anionic optical brightener comprising m anionic charges chosen from stilbene derivatives, coumarin derivatives, (benz)oxazole derivatives, (benz)imidazole derivatives, (benz)oxazole derivatives, (benzo)furan derivatives, pyrazoline derivatives, or naphthalimide derivatives;

m and n are independently chosen from an integer ranging from 1 to 10, inclusive;

X$^+$ represents a monocationic or polycationic counterion or mixture of counterions chosen from:

a) the ammoniums and phosphoniums of formulae (1) and (2) below:

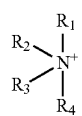

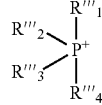

b) optionally substituted heteroaromatic groups bearing exocyclic or endocyclic, cationic charges, including (benz)imidazolium, indolinium, (benzo)triazolium, (benzo)pyrylium and (benzo)pyridinium groups, of formulae (3) and (4) below:

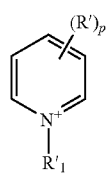

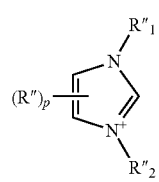

c) symmetrical or dissymmetrical dimers of formulae (1), (2), (3) and (4) chosen from those of formulae (1') to (8'):

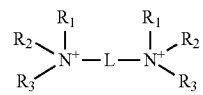

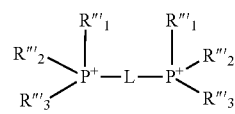

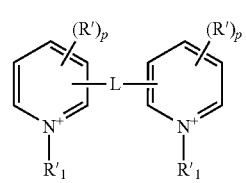

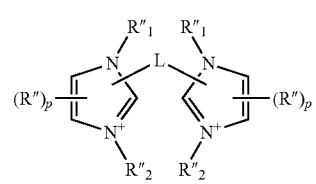

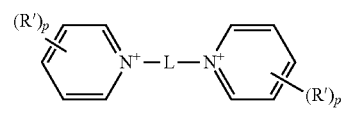

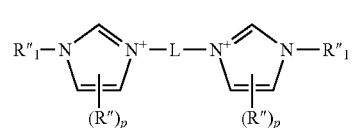

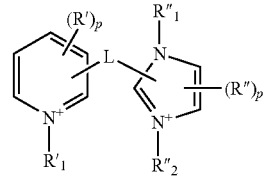

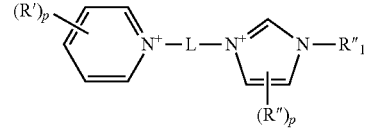

d) metallic cations of copper, iron, lithium, magnesium, manganese, gold and zinc, chosen from: Cu$^+$, Cu$^{2+}$, Fe$^{2+}$, Fe$^{3+}$, Li$^+$, Mg$^{2+}$, Mn$^{4+}$, Au$^{3+}$ and Zn$^{2+}$; and e) cationic oligomers or polymers;

wherein, in formulae (1) to (4) and (1') to (8'):

R$_1$, R$_2$, R$_3$ and R$_4$ are independently chosen from
i) linear or branched (C$_1$-C$_{20}$)alkyl;
ii) (C$_2$-C$_{20}$)alkenyl;
iii) (hetero)aryl(C$_1$-C$_{20}$)alkyl; (hetero)cycloalkyl (C$_1$-C$_{20}$)alkyl, or
iv) (hetero)aryl;

the alkyl or alkenyl group of the groups of i), ii), iii) or iv) optionally interrupted with one or more identical or different heteroatoms chosen from an oxygen or sulfur atom, the amino —N(R)—, ammonium —N$^+$(R$_a$)(R$_b$)—, —C(O)—, —C(S)— group or a combination thereof, wherein R, R$_a$ and R$_b$ are independently chosen from hydrogen atoms or alkyl groups;

or alternatively the radicals R$_1$ and R$_2$ form, together with the quaternized nitrogen or phosphorus atom, a saturated 5- or 6-membered heterocycle, the said heterocycle optionally partially unsaturated, optionally interrupted with a heteroatom chosen from an oxygen atom, the group —N(R)—, or ammonium —N$^+$(R$_a$)(R$_b$)— wherein R, R$_a$ and R$_b$ are independently chosen from hydrogen atoms or alkyl groups, and/or the said heterocycle optionally substituted with one or more alkyl groups;

R'$_1$, R"$_1$ and R"$_2$ are independently chosen from
  i) linear or branched (C$_1$-C$_{20}$)alkyl;
  ii) (C$_2$-C$_{20}$)alkenyl;
the alkyl or alkenyl group of the groups of i) and ii) optionally interrupted with one or more identical or different heteroatoms chosen from an oxygen or sulfur atom or ammonium —N$^+$(R$_a$)(R$_b$)—, —C(O)—, —C(S)— or a combination thereof, wherein R, R$_a$ and R$_b$ are independently chosen from hydrogen atoms or alkyl groups;

wherein R'$_1$, R"$_1$ and R"$_2$, may optionally be substituted with at least one hydroxyl, hydroxycarbonyl or carboxyl, (C$_1$-C$_6$)alkoxycarbonyl, alkyl(C$_1$-C$_6$)carbonyloxy, carbamoyloxy, (di)(C$_1$-C$_6$)(alkyl)silyl or tri(C$_1$-C$_5$)alkylsilyl group;

R' and R" are independently chosen from
  i) (C$_1$-C$_5$)alkyl optionally substituted with one or more radicals chosen from hydroxyl radicals,
  ii) (C$_1$-C$_5$)alkoxycarbonyl,
  iii) hydroxyl,
  iv) halogen,
  v) (C$_1$-C$_5$)alkoxy,
  vi) (poly)hydroxy(C$_1$-C$_5$)alkoxy,
  vii) (di)(C$_1$-C$_5$)(alkyl)amino,
  viii) nitro,
  ix) acylamino (—N(R)—C(O)R') with R chosen from a hydrogen atom or a (hydroxy)(C$_1$-C$_5$)alkyl radical,
  x) carbamoyl ((R)$_2$N—C(O)—) with R as defined for ix),
  xi) carboxylic acid or ester, (—O—C(O)R') or (—C(O)OR') with R' as defined for ix) the carboxylic radical optionally in acid or salified form,
  xii) alkylsulfonylamino (R'S(O)$_2$—N(R)—) or aminosulfonyl ((R)$_2$N—S(O)$_2$—) with R as defined for ix),
  xiii) (poly)haloalkyl;
or alternatively when p is greater than or equal to 2, two groups R' or R" borne by two contiguous carbon atoms together form a (hetero)cycle or a (hetero)aryl;

R'''$_1$, R'''$_2$, R'''$_3$ and R'''$_4$ independently chosen from
  i) linear or branched (C$_1$-C$_{20}$)alkyl;
  ii) (C$_2$-C$_{20}$)alkenyl;
the alkyl or alkenyl group of the groups of i) and ii) optionally substituted and/or interrupted with one or more identical or different heteroatoms chosen from an oxygen or sulfur atom, the amino —N(R)—, ammonium —N$^+$(R$_a$)(R$_b$)—, —C(O)—, —C(S)— group or a combination thereof, with R, R$_a$ and R$_b$ independently chosen from hydrogen atoms or alkyl groups;

p is equal to 0, 1, 2, 3 or 4;

L represents a linear or branched, saturated or unsaturated divalent C$_1$-C$_{30}$ hydrocarbon-based chain, optionally interrupted and/or optionally terminated at one or both of its ends with one or more divalent groups or combinations thereof chosen from:
  —N(R$_a$)—; —N$^+$(R$_a$)(R$_b$)—, Q$^-$; —O—; —S—; —S(O)—, —S(O)$_2$—, —C(O)— and —C(S)— with R$_a$ and R$_b$ independently chosen from hydrogen atoms and a C$_1$-C$_4$ alkyl, hydroxy(C$_1$-C$_8$)alkyl or amino(C$_1$-C$_8$)alkyl radicals and Q$^-$ represents an organic or mineral anionic counterion;
  an aromatic or non-aromatic, saturated or unsaturated, fused or non-fused, cationic or non-cationic (hetero)cyclic radical optionally comprising one or more identical or different, optionally substituted heteroatoms;

wherein:
  when the dyes of formula (Ia) are such that R$_1$, R$_2$, R$_3$ and R$_4$ are independently chosen from i) linear or branched (C$_1$-C$_{20}$)alkyl; ii) (C$_2$-C$_{20}$)alkenyl; the alkyl or alkenyl group of the groups of i) and ii) optionally interrupted with one or more identical or different heteroatoms chosen from an oxygen or sulfur atom or the amino —N(R)— group, then at least one of the said radicals R$_1$, R$_2$, R$_3$ and R$_4$ is substituted with at least one hydroxyl, hydroxycarbonyl or carboxyl, (C$_1$-C$_6$)alkoxycarbonyl, (C$_1$-C$_6$)alkylcarbonyloxy, carbamoyloxy, (di)(C$_1$-C$_6$)(alkyl)silyl or tri(C$_1$-C$_5$)alkylsilyl group;
  when p is equal to 2, 3 or 4, then the groups R' are identical or different and R" are identical or different;
  when the anionic part of the anionic direct dye or of the anionic optical brightener contains a sulfonate group or a carboxylate group, then m=n=1; and
  when the anionic part of the anionic direct dye or of the anionic optical brightener contains anionic groups other than the sulfonate or carboxylate group, it is combined with one or more organic or mineral cationic counterions or X$^+$ for affording the electrical neutrality of formula (Ia) or (Ib).

2. The method of claim 1, wherein the composition comprises at least one anionic compound of formula (Ib) wherein the anionic counterion(s) X$^+$ are of ammonium type R$_1$R$_2$R$_3$R$_4$N$^+$ and wherein R$_1$, R$_2$, R$_3$ and R$_4$ are independently chosen from i) (C$_1$-C$_{20}$)alkyl; ii) (C$_2$-C$_{20}$)alkenyl; the alkyl or alkenyl group of the groups i) and ii) optionally interrupted with one or more identical or different heteroatoms chosen from oxygen, sulfur or N(Rα) with Rα representing a hydrogen atom or an alkyl group.

3. The method of claim 2, wherein the composition comprises at least one anionic compound of formula (Ib) wherein the anionic counterion(s) X$^+$ are ammonium R$_1$R$_2$R$_3$R$_4$N$^+$ with R$_1$, R$_2$, R$_3$, and R$_4$ independently chosen from linear (C$_1$-C$_{20}$)alkyl groups.

4. The method of claim 1, wherein the composition comprises at least one anionic compound of at least one of formula (Ia) and (Ib), wherein the counterions X$^+$ are chosen from 1 to 172:

| N,N,N-trimethyl-1-hexanaminium | N,N-dimethylpyrrolidinium |
|---|---|
| 1 | 2 |
| 1-ethyl-1-methylpyrrolidinium | N-ethyl-N-methyl-N-(1-methylethyl)-2-propanaminium |
| 3 | 4 |

-continued

| | |
|---|---|
| N,N,N-tributyl-1-heptanaminium 5 | N,N,N-tributyl-1-hexanaminium 6 |
| N,N,N-triethyl-1-octanaminium 7 | 1-methyl-1-pentylpyrrolidinium 8 |
| 1-hexyl-1-methylpyrrolidinium 9 | N,N,N-trimethyl-1-octanaminium 10 |
| cocoalkylpentaethoxymethyl-ammonium 11 | N-hexyl-N,N,N-triethylammonium 12 |
| Cetyltrimethylammonium 13 | N,N,N-triethyl-1-heptanaminium 14 |
| N,N,N-tributyl-1-hexanaminium 15 | N-ethyl-N,N-bis(1-methylethyl)-1-heptanaminium 16 |
| N,N,N-tributyl-1-octanaminium 17 | |

-continued

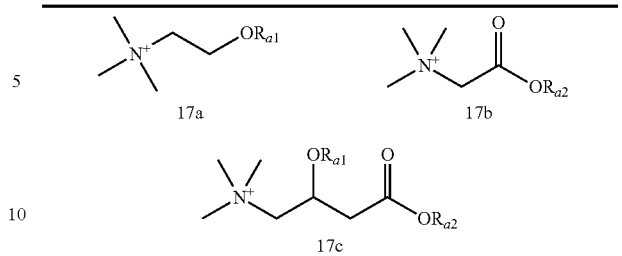

in which formulae 17a, b and c $R_{a1}$ represents a hydrogen atom or a $(C_1-C_{10})$alkyl or $(C_1-C_{10})$alkylcarbonyl radical; and $R_{a2}$ represents a hydrogen atom or a $(C_1-C_{10})$alkyl radical $(CH_3)_3N^+—(CH_2)_5—N^+(CH_3)_3$
18

$(CH_3)_3N^+—(CH_2)_6—N^+(CH_3)_3$
19

$(CH_3)_3N^+—(CH_2)_7—N^+(CH_3)_3$
20

$(CH_3)_3N^+—(CH_2)_8—N^+(CH_3)_3$
21

$(CH_3)_3N^+—(CH_2)_9—N^+(CH_3)_3$
22

$(CH_3)_3N^+—(CH_2)_{10}—N^+(CH_3)_3$
23

$(n-Bu)_3N^+—(CH_2)_6—N^+(n-Bu)_3$
24

$[CH_3—(CH_2)_7—N^+(CH_3)_2—(CH_2)_2—]_2$
25

$n-oct-N^+(CH_3)_2—(CH_2)_3—N^+(CH_3)_2-n-oct$
26

$[CH_3—(CH_2)_7—N^+(CH_3)_2—(CH_2)_2—]_2$
27

$n-oct-N^+(CH_3)_2—(CH_2)_5—N^+(CH_3)_2-n-oct$
28

$[CH_3—(CH_2)_7—N^+(CH_3)_2—(CH_2)_3—]_2$
29

$n-oct-N^+(CH_3)_2—(CH_2)_7—N^+(CH_3)_2-n-oct$
30

$n-hex-N^+(CH_3)_2—(CH_2)_4—N^+(CH_3)_2-n-hex$
31

$n-hex-N^+(CH_3)_2—(CH_2)_8—N^+(CH_3)_2-n-hex$
32

$CH_3—N^+(CH_3CH_2)_2—(CH_2)_3—N^+(CH_3)_2-n-Bu$
33

$(CH_3)_3N^+—CH_2—CH(OH)—CH_2—N^+(CH_3)_3$
34

$HO—CH_2—CH_2—N^+(CH_3)_2—CH_2—CH(OH)—CH_2—N^+(CH_3)_2—CH_2—CH_2—OH$
35

$(CH_3)_3N^+—(CH_2)_2—O—C(O)—CH_2—]_2$
36

$(CH_3)_3N^+—(CH_2)_2—O—C(O)—(CH_2)_3—]_2$
37

$(CH_3)_3N^+—(CH_2)_2—O—C(O)—(CH_2)_2—N^+(CH_3)_3$
38

$[CH_3CH_2O—C(O)—CH_2—N^+(CH_3)_2—(CH_2)_3—]_2$
39

$CH_3O—C(O)—CH_2—N^+(CH_3)_2—(CH_2)_3—N^+(CH_3)_2—CH_2—C(O)—OCH_3$
40

$[H_2N—C(O)—CH_2—N^+(CH_3)_2—CH_2—]_2$
41

$[HO—CH_2—NH—C(O)—CH_2—N^+(CH_3)_2—CH_2—]_2$
42

$[CH_3—(CH_2)_6—N^+(CH_3)_2—(CH_2)_2—S]_2$
43

$(CH_3)_3N^+—(CH_2)_2—S—S—(CH_2)_2—N^+(CH_3)_3$
44

$[CH_3—(CH_2)_{15}—N^+(CH_3)_2—CH_2—C(O)—NH—(CH_2)_2—S—]_2$
45

$[HO—CH_2—NH—C(O)—CH_2—N^+(CH_3)_2—(CH_2)_2—S—]_2$
46

$(CH_3—CH_2)_3N^+—CH_2—CH_2—O—CH_2—CH_2—N^+(CH_2—CH_3)_3$
47

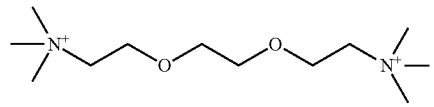

48

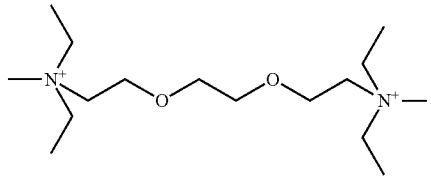

49

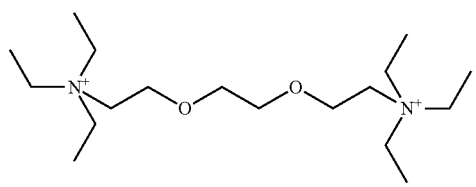 [SMILES: CC[N+](CC)(CC)CCOCCOCC[N+](CC)(CC)CC]

50

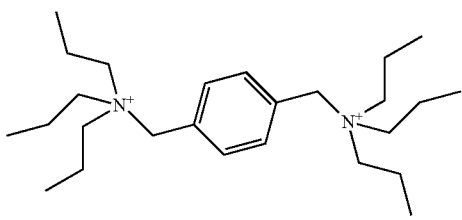 [SMILES: CCC[N+](CCC)(CCC)Cc1ccc(C[N+](CCC)(CCC)CCC)cc1]

51

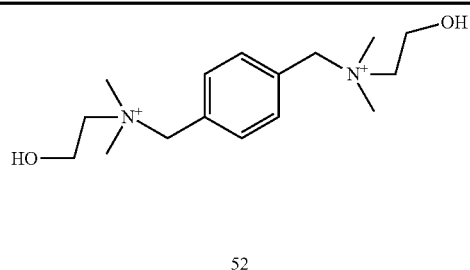

52

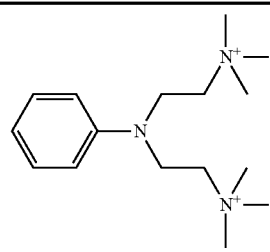

53

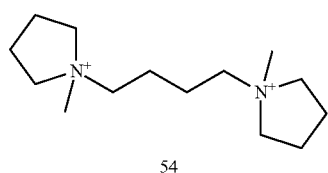

54

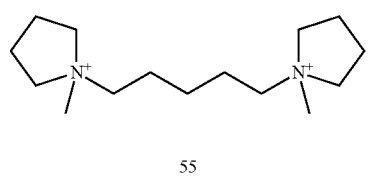

55

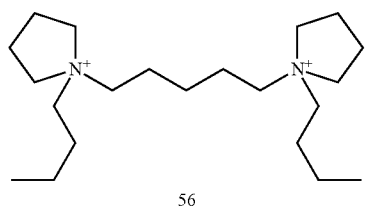

56

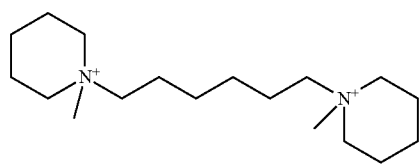 [SMILES: C[N+]1(CCCCCC[N+]2(C)CCCCC2)CCCCC1]

57

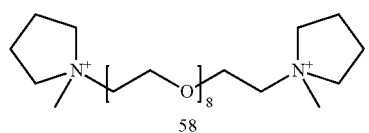

58

N-ethylpyridinium
59
1-ethyl-3-methylpyridinium
60
N-butylpyridinium
61
4-(dimethylamino)-1-ethylpyridinium
62
1-ethylnicotinic acid ethyl ester
63
1-hexyl-3-methylpyridinium
64
1-butyl-3-methylpyridinium
65
1-hexyl-3,5-dimethylpyridinium
66
4-(dimethylamino)-1-hexylpyridinium
67
1-butylnicotinic acid butyl ester
68
1-methyl-3-octylpyridinium; 1-
69
1-hexyl-3-methyl-4-(dimethylamino)pyridinium
70
1-hexyl-4-(4-methylpiperidino)pyridinium
71
1-hexyl-4-(4-methylpiperidino)pyridinium
72

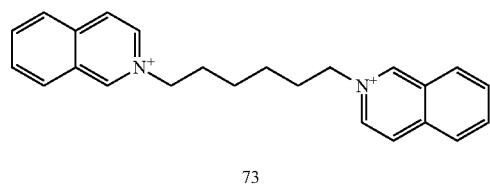

73

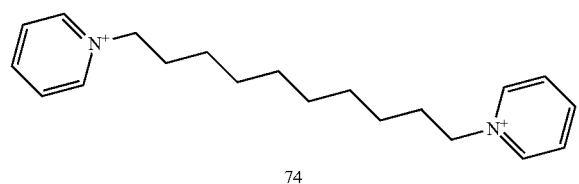

74

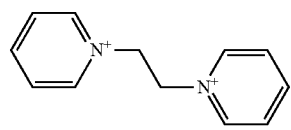

75

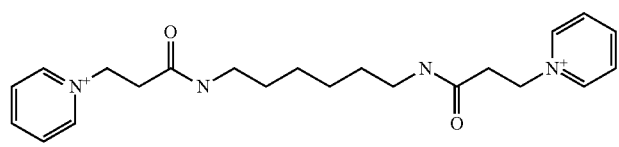 [SMILES: O=C(CC[n+]1ccccc1)NCCCCCCNC(=O)CC[n+]1ccccc1]

76

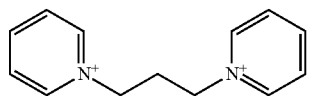 [SMILES: c1cc[n+](CCC[n+]2ccccc2)cc1]
77
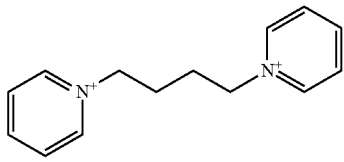 [SMILES: c1cc[n+](CCCC[n+]2ccccc2)cc1]
78
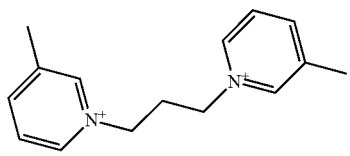 [SMILES: Cc1ccc[n+](CCC[n+]2cccc(C)c2)c1]
79
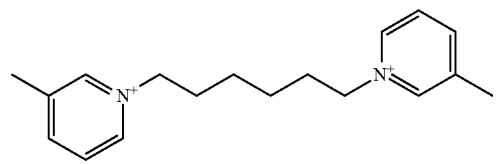
80
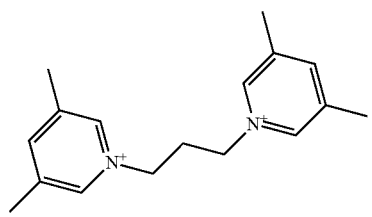
81
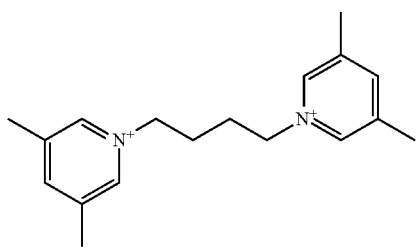
82
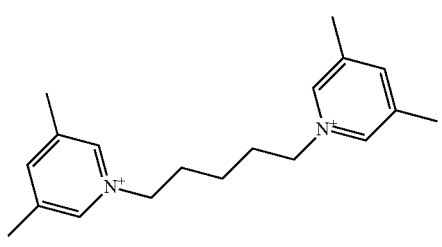
83
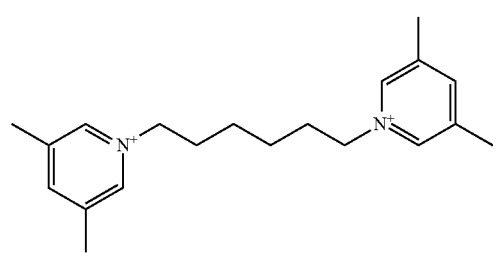
84
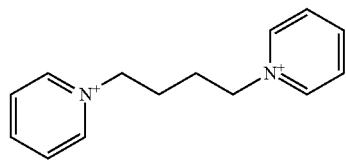 [SMILES: c1cc[n+](CCCC[n+]2ccccc2)cc1]
85
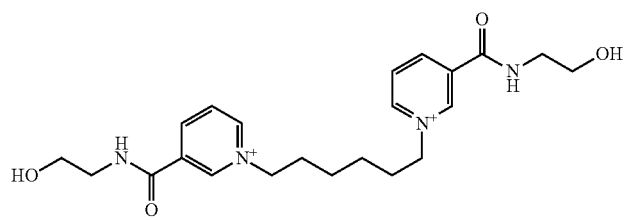 [SMILES: O=C(NCCO)c1ccc[n+](CCCCCC[n+]2cccc(C(=O)NCCO)c2)c1]
86
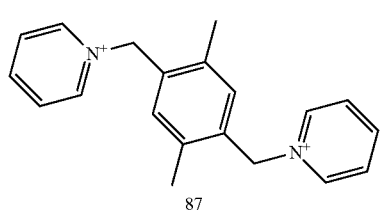
87
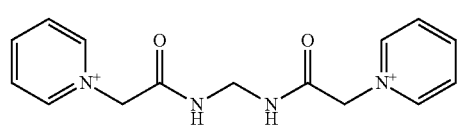 [SMILES: O=C(C[n+]1ccccc1)NCNC(=O)C[n+]1ccccc1]
88
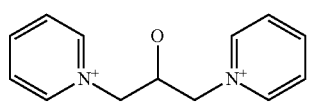 [SMILES: OC(C[n+]1ccccc1)C[n+]1ccccc1]
89
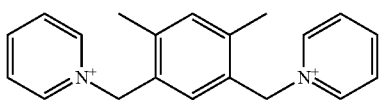
90

-continued
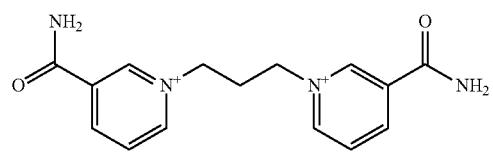 [SMILES: NC(=O)c1ccc[n+](CCC[n+]2cccc(C(N)=O)c2)c1]
91
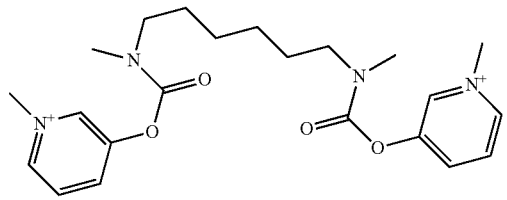 [SMILES: CN(CCCCCCN(C)C(=O)Oc1ccc[n+](C)c1)C(=O)Oc1ccc[n+](C)c1]
92
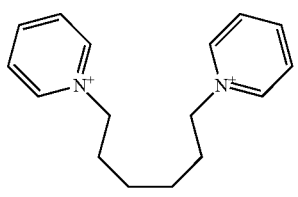 [SMILES: c1cc[n+](CCCCCC[n+]2ccccc2)cc1]
93
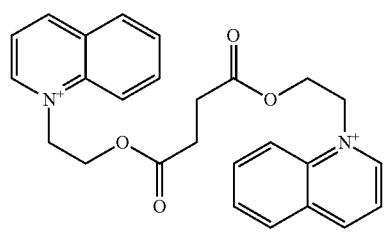 [SMILES: O=C(CCC(=O)OCC[n+]1cccc2ccccc21)OCC[n+]1cccc2ccccc21]
94
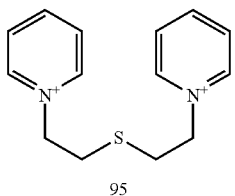
95
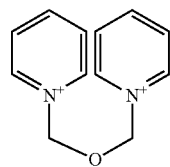 [SMILES: c1cc[n+](COC[n+]2ccccc2)cc1]
96
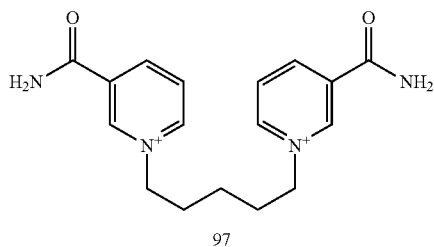
97
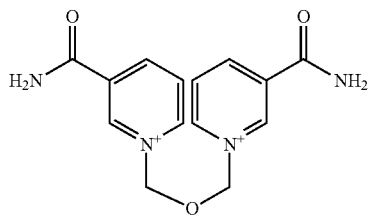 [SMILES: NC(=O)c1ccc[n+](COC[n+]2cccc(C(N)=O)c2)c1]
98
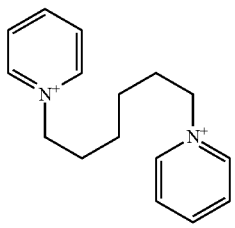 [SMILES: c1cc[n+](CCCCCC[n+]2ccccc2)cc1]
99
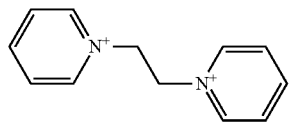
100
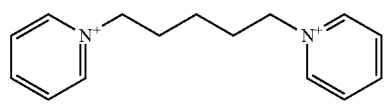 [SMILES: c1cc[n+](CCCCC[n+]2ccccc2)cc1]
101
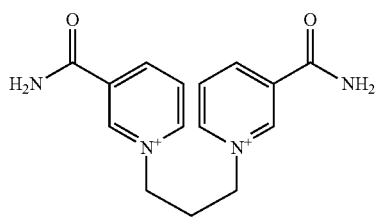 [SMILES: NC(=O)c1ccc[n+](CCC[n+]2cccc(C(N)=O)c2)c1]
102

-continued

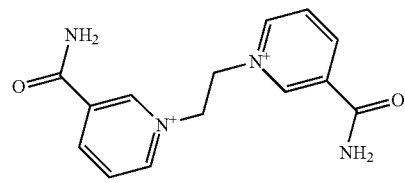 [SMILES: NC(=O)c1ccc[n+](CC[n+]2cccc(C(N)=O)c2)c1]

103

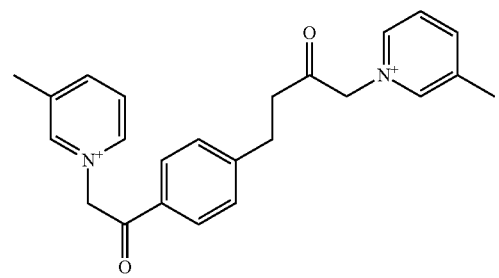

104

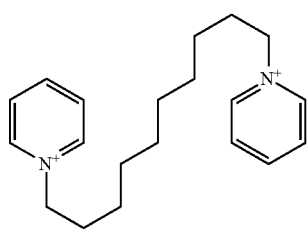 [SMILES: c1cc[n+](CCCCCCCCCC[n+]2ccccc2)cc1]

105

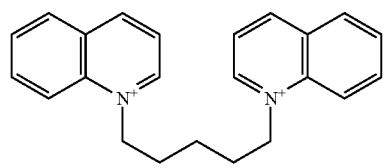 [SMILES: c1ccc2c(c1)ccc[n+]2CCCCC[n+]1cccc2ccccc21]

106

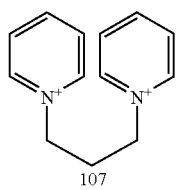

107

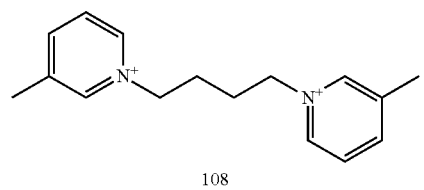

108

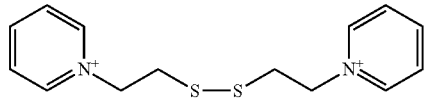 [SMILES: c1cc[n+](CCSSCC[n+]2ccccc2)cc1]

109

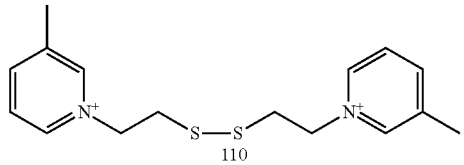

110

1,3-dimethylimidazolium
111
2,4,5-trimethylimidazolium
113
1,3-diethylimidazolium
115
1-ethyl-2,3-dimethylimidazolium
117
1-butyl-3-methylimidazolium
119
1,2-dimethyl-3-propylimidazolium
121
1-butyl-2,3-dimethylimidazolium
123
1-butyl-3-ethylimidazolium
125
1-hexyl-2,3-dimethylimidazolium
127
1-octyl-3-methylimidazolium
129
1-decyl-3-methylimidazolium
131

1-ethyl-3-methylimidazolium
112
1-(2-hydroxyethyl)-3-methylimidazolium
114
1-propyl-3-methylimidazolium
116
1-methyl-3-(1-methylethyl)imidazolium
118
1-methyl-3-(2-methylprop-1-enyl)imidazolium
120
1,2,3,4,5-pentamethylimidazolium
122
1-pentyl-3-methylimidazolium
124
1-hexyl-3-methylimidazolium
126
1-heptyl-3-methylimidazolium
128
1-methyl-3-nonylimidazolium
130
1-dodecyl-3-methylimidazolium
132

1-dodecyl-3-methylimidazolium
133

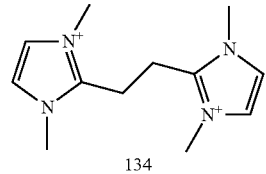

134

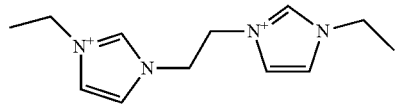 [SMILES: CCn1cc[n+](CCn2cc[n+](CC)c2)c1]

135

-continued 136
137
138
139
140
141
142
143
144
145
146
147
148
149
150
151

-continued
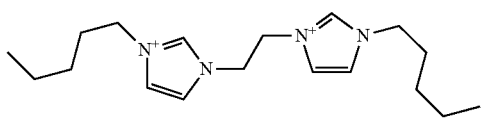
152
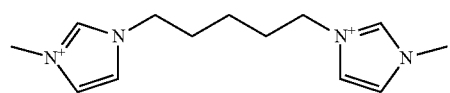
153
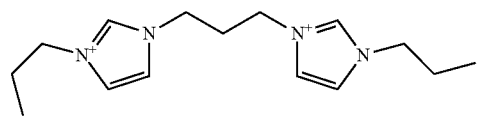 [SMILES: CCCn1cc[n+](CCCn2cc[n+](CCC)c2)c1]
154
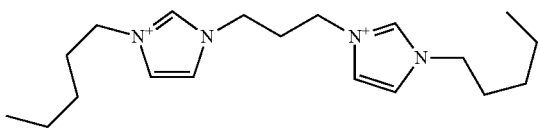 [SMILES: CCCCCn1cc[n+](CCCn2cc[n+](CCCCC)c2)c1]
155
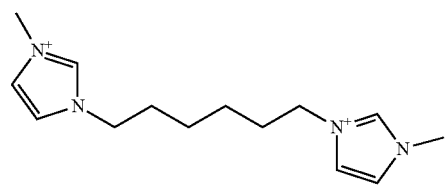 [SMILES: Cn1cc[n+](CCCCCCn2cc[n+](C)c2)c1]
156
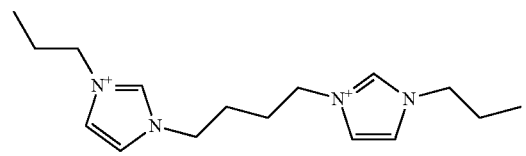 [SMILES: CCCn1cc[n+](CCCCn2cc[n+](CCC)c2)c1]
157
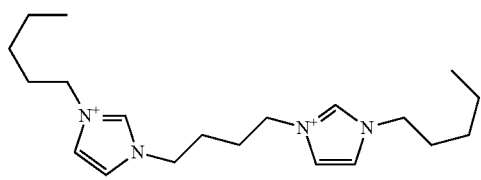 [SMILES: CCCCCn1cc[n+](CCCCn2cc[n+](CCCCC)c2)c1]
158
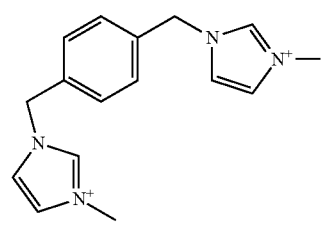 [SMILES: C[n+]1ccn(Cc2ccc(Cn3cc[n+](C)c3)cc2)c1]
159
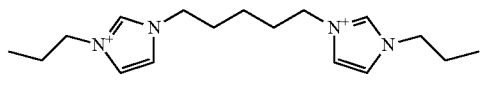 [SMILES: CCCn1cc[n+](CCCCCn2cc[n+](CCC)c2)c1]
160
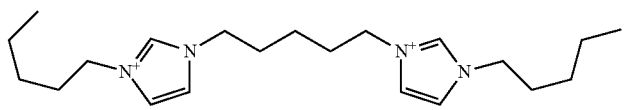 [SMILES: CCCCCn1cc[n+](CCCCCn2cc[n+](CCCCC)c2)c1]
161
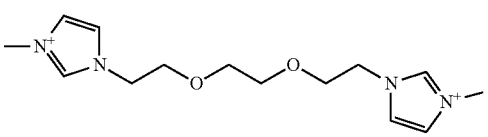
162
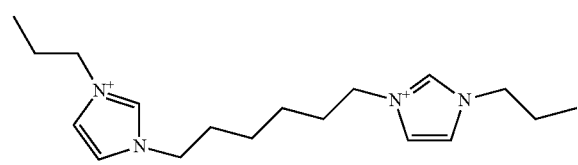 [SMILES: CCCn1cc[n+](CCCCCCn2cc[n+](CCC)c2)c1]
163
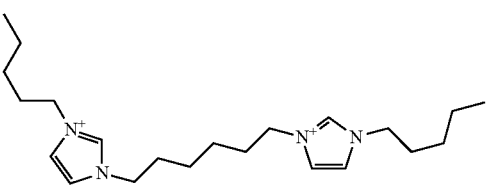 [SMILES: CCCCCn1cc[n+](CCCCCCn2cc[n+](CCCCC)c2)c1]
164
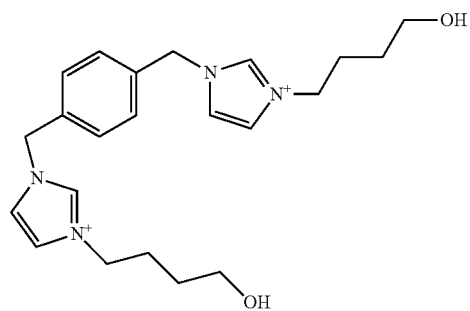 [SMILES: OCCCC[n+]1ccn(Cc2ccc(Cn3cc[n+](CCCCO)c3)cc2)c1]
165

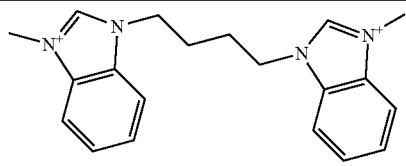

166
triisobutylmethylphosphonium
168
tetrabutylphosphonium
170

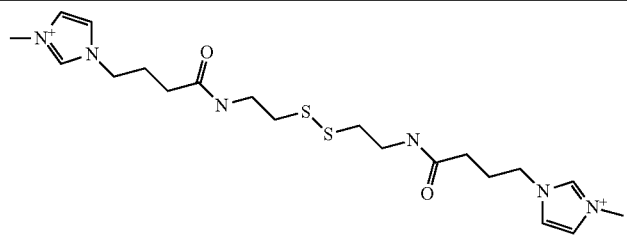

167
trihexyl(tetradecyl)phosphonium
169
tri-i-butyl(methyl)phosphonium
171
tributyl(tetradecyl)phosphonium
172
tetrabutylammonium.
173

5. The method of claim 1, wherein the composition comprises at least one anionic compound of at least one of formula (Ia) and (Ib), wherein m is equal to n.

6. The method of claim 1, wherein the composition comprises at least one anionic compound of at least one of formula (Ia) and (Ib), wherein m and n are equal to 1, 2 or 3.

7. The method of claim 1, wherein the composition comprises at least one anionic compound of at least one of formula (Ia) and (Ib), wherein at least one of $Col^{(-)}m$ and $Azu^{(-)}m$ comprises:
- at least one sulfonate group and at least one (hetero)aryl group, it being understood that at least one sulfonate group is directly bonded to a (hetero)aryl group; and optionally
- at least one anionic group $G^-$ with $G^-$ independently chosen from anionic groups chosen from alkoxide $O^-$, thioalkoxide $S^-$, carboxylate and thiocarboxylate: C(Q)Q'$^-$ wherein Q and Q' independently chosen from oxygen or sulfur atoms.

8. The method of claim 1, wherein the composition comprises at least one anionic compound of at least one of formula (Ia) and (Ib), wherein at least one of $Col^{(-)}m$ and $Azu^{(-)}m$ comprises at least one carboxylate group and at least one (hetero)aryl group, it being understood that at least one carboxylate group is directly bonded to a (hetero)aryl group.

9. The method of claim 1, wherein the composition comprises at least one anionic compound of at least one of formula (Ia) and formula (Ib);
wherein the at least one anionic compound of formula (Ia) is derived from acidic nitro direct dyes, acidic azo dyes, acidic azine dyes, acidic triarylmethane dyes, acidic indoamine dyes, acidic anthraquinone dyes, indigoids and acidic natural dyes;
wherein the at least one anionic compound of formula (Ib) is derived from stilbene;
wherein the at least one anionic compound of formula (Ia) and formula (Ib) comprises a sulfonate or carboxylate group bearing a cationic counterion $X^+$,
wherein $X^+$ represents a monocationic or polycationic counterion or mixture of counterions chosen from:
f) the ammoniums and phosphoniums of formulae (1) and (2) below:

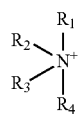

(1)

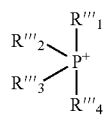

(2)

g) optionally substituted heteroaromatic groups bearing exocyclic or endocyclic, cationic charges, including (benz)imidazolium, indolinium, (benzo)triazolium, (benzo)pyrylium and (benzo)pyridinium groups, of formulae (3) and (4) below:

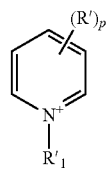

(3)

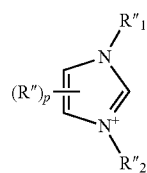

(4)

h) symmetrical or dissymmetrical dimers of formulae (1), (2), (3) and (4) chosen from those of formulae (1') to (8'):

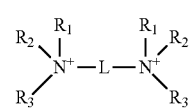

(1')

-continued

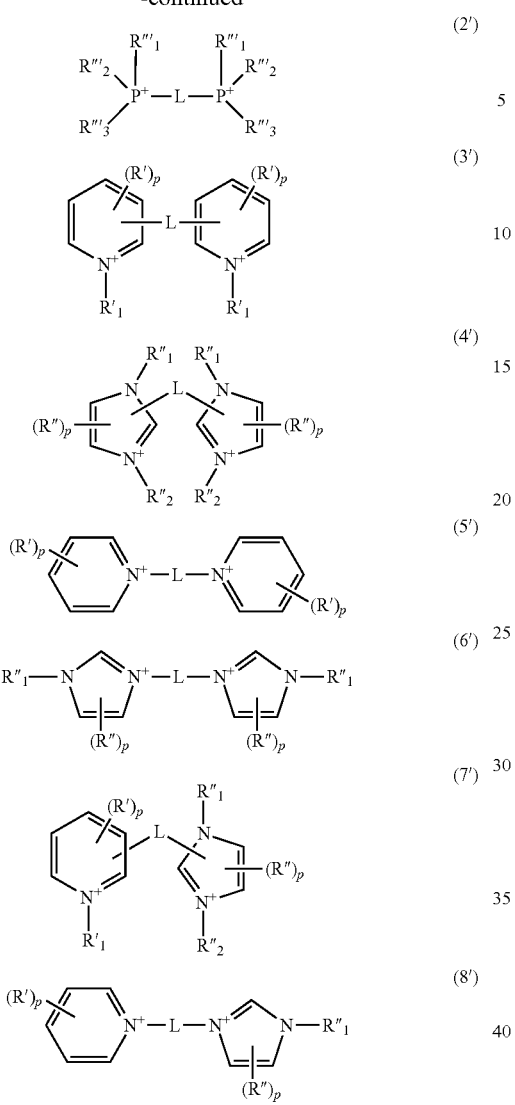

i) metallic cations of copper, iron, lithium, magnesium, manganese, gold and zinc, chosen from: $Cu^+$, $Cu^{2+}$, $Fe^{2+}$, $Fe^{3+}$, $Li^+$, $Mg^{2+}$, $Mn^{4+}$, $Au^{3+}$ and $Zn^{2+}$; and j) cationic oligomers or polymers;

wherein, in formulae (1) to (4) and (1') to (8'):
  $R_1$, $R_2$, $R_3$ and $R_4$ are independently chosen from
    v) linear or branched $(C_1-C_{20})$alkyl;
    vi) $(C_2-C_{20})$alkenyl;
    vii) (hetero)aryl$(C_1-C_{20})$alkyl; (hetero)cycloalkyl $(C_1-C_{20})$alkyl, or
    viii) (hetero)aryl;
  the alkyl or alkenyl group of the groups of i), ii), iii) or iv) optionally interrupted with one or more identical or different heteroatoms chosen from an oxygen or sulfur atom, the amino —N(R)—, ammonium —$N^+(R_a)(R_b)$—, —C(O)—, —C(S)— group or a combination thereof, wherein R, $R_a$ and $R_b$ are independently chosen from hydrogen atoms or alkyl groups;
  or alternatively the radicals $R_1$ and $R_2$ form, together with the quaternized nitrogen or phosphorus atom, a saturated 5- or 6-membered heterocycle, the said heterocycle optionally partially unsaturated, optionally interrupted with a heteroatom chosen from an oxygen atom, the group —N(R)—, or ammonium —$N^+(R_a)(R_b)$— wherein R, $R_a$ and $R_b$ are independently chosen from hydrogen atoms or alkyl groups, and/or the said heterocycle optionally substituted with one or more alkyl groups;

$R'_1$, $R''_1$ and $R''_2$ are independently chosen from
  iii) linear or branched $(C_1-C_{20})$alkyl;
  iv) $(C_2-C_{20})$alkenyl;
the alkyl or alkenyl group of the groups of i) and ii) optionally interrupted with one or more identical or different heteroatoms chosen from an oxygen or sulfur atom or ammonium —$N^+(R_a)(R_b)$—, —C(O)—, —C(S)— or a combination thereof, wherein R, $R_a$ and $R_b$ are independently chosen from hydrogen atoms or alkyl groups;

wherein $R'_1$, $R''_1$ and $R''_2$, may optionally be substituted with at least one hydroxyl, hydroxycarbonyl or carboxyl, $(C_1-C_6)$alkoxycarbonyl, alkyl$(C_1-C_6)$carbonyloxy, carbamoyloxy, (di)$(C_1-C_6)$(alkyl)silyl or tri $(C_1-C_5)$alkylsilyl group;

R' and R" are independently chosen from
  xiv) $(C_1-C_5)$alkyl optionally substituted with one or more radicals chosen from hydroxyl radicals,
  xv) $(C_1-C_5)$alkoxycarbonyl,
  xvi) hydroxyl,
  xvii) halogen,
  xviii) $(C_1-C_5)$alkoxy,
  xix) (poly)hydroxy$(C_1-C_5)$alkoxy,
  xx) (di)$(C_1-C_5)$(alkyl)amino,
  xxi) nitro,
  xxii) acylamino (—N(R)—C(O)R') with R chosen from a hydrogen atom or a (hydroxy)$(C_1-C_5)$alkyl radical,
  xxiii) carbamoyl $((R)_2N—C(O)—)$ with R as defined for ix),
  xxiv) carboxylic acid or ester, (—O—C(O)R') or (—C(O)OR') with R' as defined for ix) the carboxylic radical optionally in acid or salified form,
  xxv) alkylsulfonylamino $(R'S(O)_2—N(R)—)$ or aminosulfonyl $((R)_2N—S(O)_2—)$ with R as defined for ix),
  xxvi) (poly)haloalkyl;
or alternatively when p is greater than or equal to 2, two groups R' or R" borne by two contiguous carbon atoms together form a (hetero)cycle or a (hetero)aryl;

$R'''_1$, $R'''_2$, $R'''_3$ and $R'''_4$ independently chosen from
  iii) linear or branched $(C_1-C_{20})$alkyl;
  iv) $(C_2-C_{20})$alkenyl;
the alkyl or alkenyl group of the groups of i) and ii) optionally substituted and/or interrupted with one or more identical or different heteroatoms chosen from an oxygen or sulfur atom, the amino —N(R)—, ammonium —$N^+(R_a)(R_b)$—, —C(O)—, —C(S)— group or a combination thereof, with R, $R_a$ and $R_b$ independently chosen from hydrogen atoms or alkyl groups;

p is equal to 0, 1, 2, 3 or 4;

L represents a linear or branched, saturated or unsaturated divalent $C_1-C_{30}$ hydrocarbon-based chain, optionally interrupted and/or optionally terminated at one or both of its ends with one or more divalent groups or combinations thereof chosen from:
  —$N(R_a)$—; —$N^+(R_a)(R_b)$—, $Q^-$; —O—, —S—; —S(O)—, —$S(O)_2$—, —C(O)— and —C(S)— with $R_a$ and $R_b$ independently chosen from hydrogen atoms and a $C_1-C_4$ alkyl, hydroxy$(C_1-C_8)$ alkyl or amino$(C_1-C_8)$alkyl radicals and $Q^-$ represents an organic or mineral anionic counterion;

an aromatic or non-aromatic, saturated or unsaturated, fused or non-fused, cationic or non-cationic (hetero)cyclic radical optionally comprising one or more identical or different, optionally substituted heteroatoms.

10. The method of claim 1, wherein the composition comprises at least one anionic compound of at least one of formula (Ia) and (Ib) chosen from the following compounds:

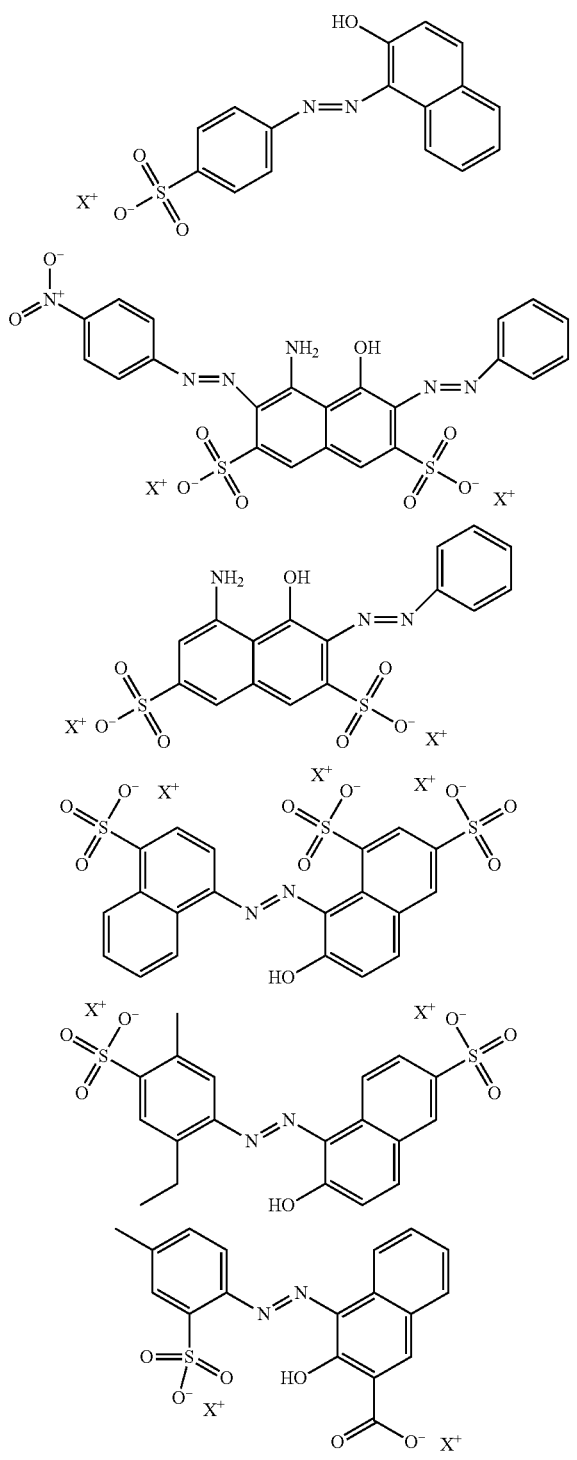
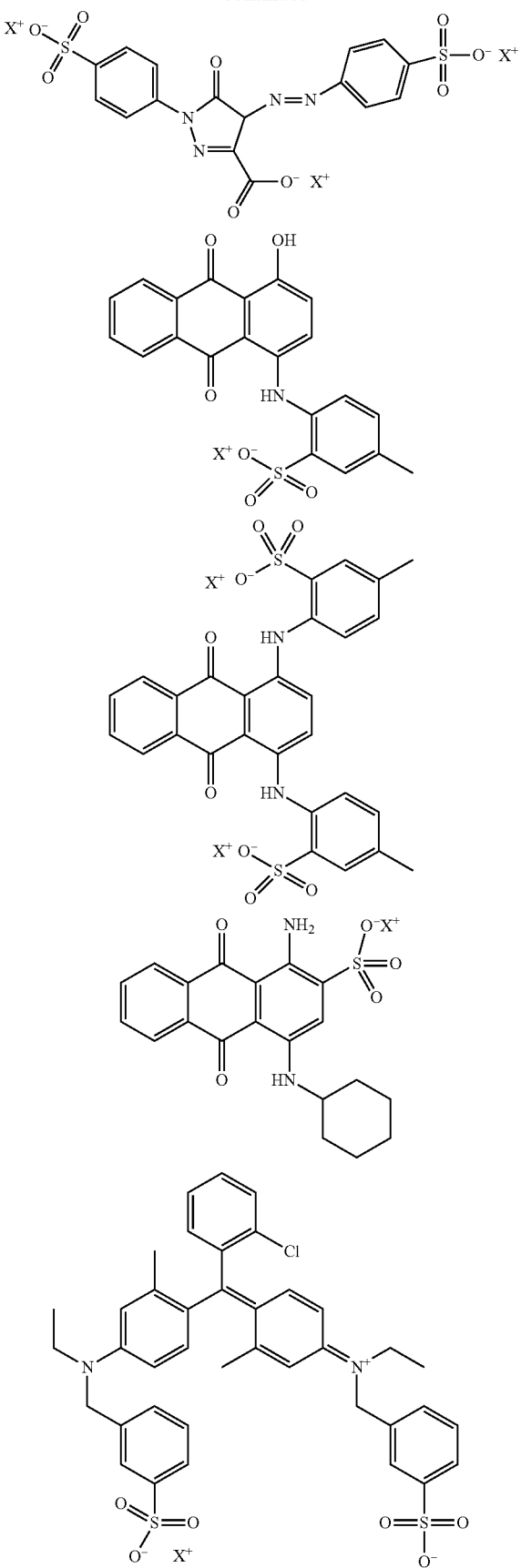

-continued

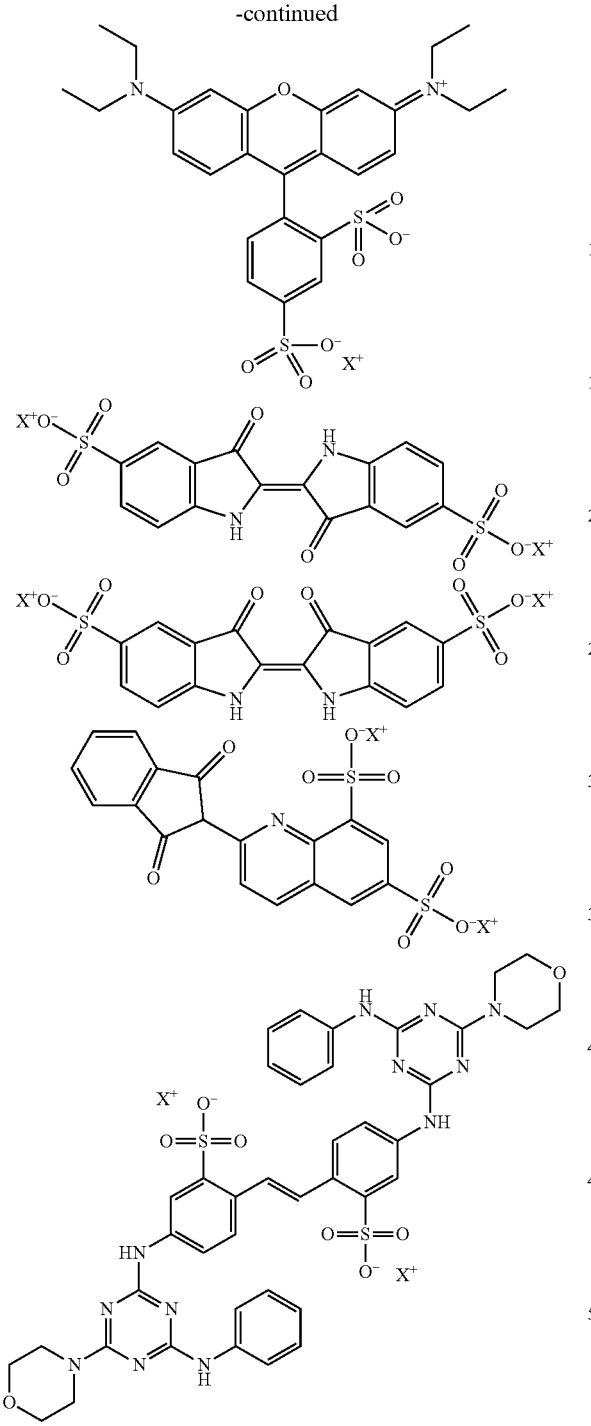

wherein X⁺ represents a monocationic or polycationic counterion or mixture of counterions chosen from:
a) the ammoniums and phosphoniums of formulae (1) and (2) below:

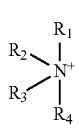
(1)

-continued

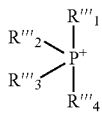
(2)

b) optionally substituted heteroaromatic groups bearing exocyclic or endocyclic, cationic charges, including (benz)imidazolium, indolinium, (benzo)triazolium, (benzo)pyrylium and (benzo)pyridinium groups, of formulae (3) and (4) below:

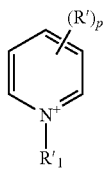
(3)

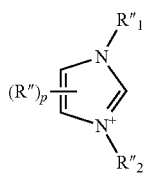
(4)

c) symmetrical or dissymmetrical dimers of formulae (1), (2), (3) and (4) chosen from those of formulae (1') to (8'):

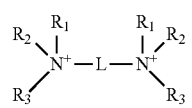
(1')

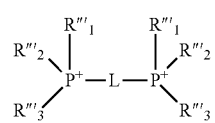
(2')

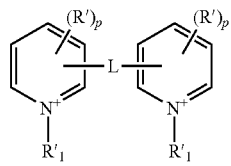
(3')

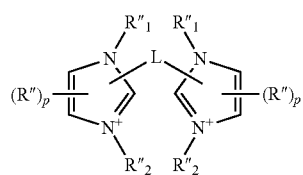
(4')

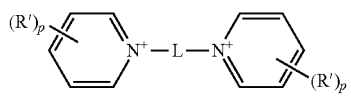
(5')

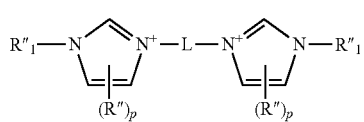
(6')

-continued

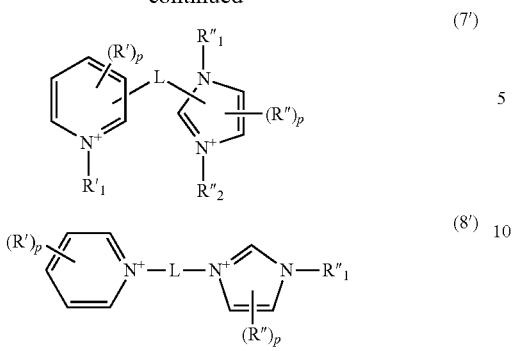

d) metallic cations of copper, iron, lithium, magnesium, manganese, gold and zinc, chosen from: $Cu^+$, $Cu^{2+}$, $Fe^{2+}$, $Fe^{3+}$, $Li^+$, $Mg^{2+}$, $Mn^{4+}$, $Au^{3+}$ and $Zn^{2+}$; and e) cationic oligomers or polymers;

wherein, in formulae (1) to (4) and (1') to (8'):

$R_1$, $R_2$, $R_3$ and $R_4$ are independently chosen from
  ix) linear or branched ($C_1$-$C_{20}$)alkyl;
  x) ($C_2$-$C_{20}$)alkenyl;
  xi) (hetero)aryl($C_1$-$C_{20}$)alkyl; (hetero)cycloalkyl ($C_1$-$C_{20}$)alkyl, or
  xii) (hetero)aryl;
the alkyl or alkenyl group of the groups of i), ii), iii) or iv) optionally interrupted with one or more identical or different heteroatoms chosen from an oxygen or sulfur atom, the amino —N(R)—, ammonium —$N^+(R_a)(R_b)$—, —C(O)—, —C(S)— group or a combination thereof, wherein R, $R_a$ and $R_b$ are independently chosen from hydrogen atoms or alkyl groups;
or alternatively the radicals $R_1$ and $R_2$ form, together with the quaternized nitrogen or phosphorus atom, a saturated 5- or 6-membered heterocycle, the said heterocycle optionally partially unsaturated, optionally interrupted with a heteroatom chosen from an oxygen atom, the group —N(R)—, or ammonium —$N^+(R_a)(R_b)$— wherein R, $R_a$ and $R_b$ are independently chosen from hydrogen atoms or alkyl groups, and/or the said heterocycle optionally substituted with one or more alkyl groups;

$R'_1$, $R''_1$ and $R''_2$ are independently chosen from
  v) linear or branched ($C_1$-$C_{20}$)alkyl;
  vi) ($C_2$-$C_{20}$)alkenyl;
the alkyl or alkenyl group of the groups of i) and ii) optionally interrupted with one or more identical or different heteroatoms chosen from an oxygen or sulfur atom or ammonium —$N^+(R_a)(R_b)$—, —C(O)—, —C(S)— or a combination thereof, wherein R, $R_a$ and $R_b$ are independently chosen from hydrogen atoms or alkyl groups;
wherein $R'_1$, $R''_1$ and $R''_2$, may optionally be substituted with at least one hydroxyl, hydroxycarbonyl or carboxyl, ($C_1$-$C_6$)alkoxycarbonyl, alkyl($C_1$-$C_6$)carbonyloxy, carbamoyloxy, (di)($C_1$-$C_6$)(alkyl)silyl or tri ($C_1$-$C_5$)alkylsilyl group;

R' and R'' are independently chosen from
  xxvii) ($C_1$-$C_5$)alkyl optionally substituted with one or more radicals chosen from hydroxyl radicals,
  xxviii) ($C_1$-$C_5$)alkoxycarbonyl,
  xxix) hydroxyl,
  xxx) halogen,
  xxxi) ($C_1$-$C_5$)alkoxy,
  xxxii) (poly)hydroxy($C_1$-$C_5$)alkoxy,
  xxxiii) (di)($C_1$-$C_5$)(alkyl)amino,
  xxxiv) nitro,
  xxxv) acylamino (—N(R)—C(O)R') with R chosen from a hydrogen atom or a (hydroxy)($C_1$-$C_5$)alkyl radical,
  xxxvi) carbamoyl ((R)$_2$N—C(O)—) with R as defined for ix),
  xxxvii) carboxylic acid or ester, (—O—C(O)R') or (—C(O)OR') with R' as defined for ix) the carboxylic radical optionally in acid or salified form,
  xxxviii) alkylsulfonylamino (R'S(O)$_2$—N(R)—) or am inosulfonyl ((R)$_2$N—S(O)$_2$—) with R as defined for ix),
  xxxix) (poly)haloalkyl;
or alternatively when p is greater than or equal to 2, two groups R' or R'' borne by two contiguous carbon atoms together form a (hetero)cycle or a (hetero)aryl;

$R'''_1$, $R'''_2$, $R'''_3$ and $R'''_4$ independently chosen from
  v) linear or branched ($C_1$-$C_{20}$)alkyl;
  vi) ($C_2$-$C_{20}$)alkenyl;
the alkyl or alkenyl group of the groups of i) and ii) optionally substituted and/or interrupted with one or more identical or different heteroatoms chosen from an oxygen or sulfur atom, the amino —N(R)—, ammonium —$N^+(R_a)(R_b)$13 , —C(O)—, —C(S)— group or a combination thereof, with R, $R_a$ and $R_b$ independently chosen from hydrogen atoms or alkyl groups;

p is equal to 0, 1, 2, 3 or 4;

L represents a linear or branched, saturated or unsaturated divalent $C_1$-$C_{30}$ hydrocarbon-based chain, optionally interrupted and/or optionally terminated at one or both of its ends with one or more divalent groups or combinations thereof chosen from:
  —N($R_a$)—; —$N^+(R_a)(R_b)$—, $Q^-$; —O—; —S—; —S(O)—, —S(O)$_2$—, —C(O)— and —C(S)— with $R_a$ and $R_b$ independently chosen from hydrogen atoms and a $C_1$-$C_4$ alkyl, hydroxy($C_1$-$C_8$) alkyl or amino($C_1$-$C_8$)alkyl radicals and $Q^-$ represents an organic or mineral anionic counterion;
  an aromatic or non-aromatic, saturated or unsaturated, fused or non-fused, cationic or non-cationic (hetero)cyclic radical optionally comprising one or more identical or different, optionally substituted heteroatoms;

wherein, when the part $Col^-$ or $Azu^-$ comprises several anionic charges (m=2 or 3) then $2X^+$ or $3X^+$ may correspond to a dication or a trication.

11. The method of claim 1, wherein the fibers comprise a tone depth of less than or equal to 6, comprising:
applying to the said fibers a composition comprising at least one of
at least one fluorescent dye of formula (Ia), and
at least one optical brightener of formula (Ib).

12. A compound of formula (Ia) or (Ib)

$$Col^{(-)}{}_m[X^+]_n \qquad (Ia)$$

$$Azu^{(-)}{}_m[X^+]_n \qquad (Ib)$$

and optical isomers, geometrical isomers, and solvates thereof;
wherein:
  $Col^{(-)}$ represents the anionic part of an anionic direct dye comprising m anionic charges chosen from acidic nitro direct dyes, acidic azo dyes, acidic azine dyes, acidic triarylmethane dyes, acidic indoamine dyes, acidic anthraquinone dyes, anionic styryl dyes, indigoids, or acidic natural dyes;
  $Azu^{(-)}$ represents the anionic part of an anionic optical brightener comprising m anionic charges chosen from stilbene derivatives, coumarin derivatives, (benz)oxazole derivatives, (benz)imidazole derivatives, (benz)oxazole derivatives, (benzo)furan derivatives, pyrazoline derivatives, or naphthalimide derivatives;

m and n are independently chosen from an integer ranging from 1 to 10, inclusive;

$X^+$ represents a monocationic or polycationic counterion or mixture of counterions chosen from:

k) the ammoniums and phosphoniums of formulae (1) and (2) below:

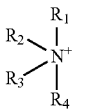

(1)

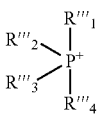

(2)

l) optionally substituted heteroaromatic groups bearing exocyclic or endocyclic, cationic charges, including (benz)imidazolium, indolinium, (benzo)triazolium, (benzo)pyrylium and (benzo)pyridinium groups, of formulae (3) and (4) below:

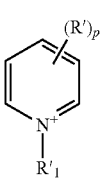

(3)

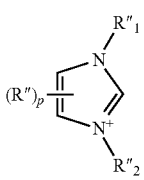

(4)

m) symmetrical or dissymmetrical dimers of formulae (1), (2), (3) and (4) chosen from those of formulae (1') to (8'):

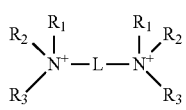

(1')

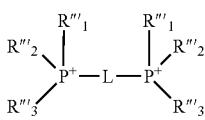

(2')

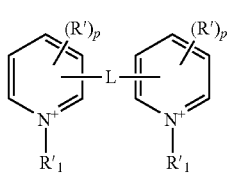

(3')

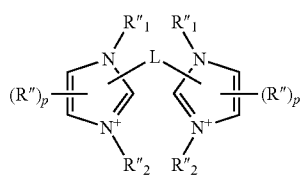

(4')

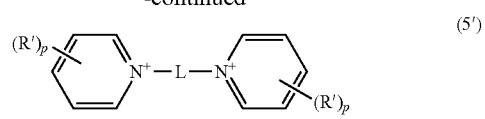

(5')

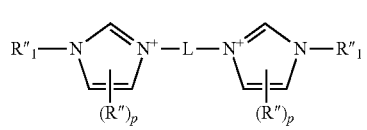

(6')

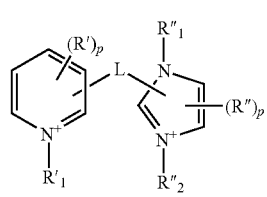

(7')

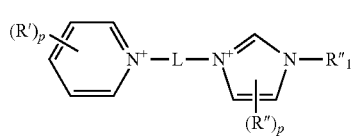

(8')

n) metallic cations of copper, iron, lithium, magnesium, manganese, gold and zinc, chosen from: $Cu^+$, $Cu^{2+}$, $Fe^{2+}$, $Fe^{3+}$, $Li^+$, $Mg^{2+}$, $Mn^{4+}$, $Au^{3+}$ and $Zn^{2+}$; and o) cationic oligomers or polymers;

wherein, in formulae (1) to (4) and (1') to (8'):

$R_1$, $R_2$, $R_3$ and $R_4$ are independently chosen from
  xiii) linear or branched ($C_1$-$C_{20}$)alkyl;
  xiv) ($C_2$-$C_{20}$)alkenyl;
  xv) (hetero)aryl($C_1$-$C_{20}$)alkyl; (hetero)cycloalkyl ($C_1$-$C_{20}$)alkyl, or
  xvi) (hetero)aryl;

the alkyl or alkenyl group of the groups of i), ii), iii) or iv) optionally interrupted with one or more identical or different heteroatoms chosen from an oxygen or sulfur atom, the amino —N(R)—, ammonium —N$^+$(R$_a$)(R$_b$)—, —C(O)—, —C(S)— group or a combination thereof, wherein R, R$_a$ and R$_b$ are independently chosen from hydrogen atoms or alkyl groups;

or alternatively the radicals $R_1$ and $R_2$ form, together with the quaternized nitrogen or phosphorus atom, a saturated 5- or 6-membered heterocycle, the said heterocycle optionally partially unsaturated, optionally interrupted with a heteroatom chosen from an oxygen atom, the group —N(R)—, or ammonium —N$^+$(R$_a$)(R$_b$)— wherein R, R$_a$ and R$_b$ are independently chosen from hydrogen atoms or alkyl groups, and/or the said heterocycle optionally substituted with one or more alkyl groups;

R'$_1$, R"$_1$ and R"$_2$ are independently chosen from
  vii) linear or branched ($C_1$-$C_{20}$)alkyl;
  viii) ($C_2$-$C_{20}$)alkenyl;

the alkyl or alkenyl group of the groups of i) and ii) optionally interrupted with one or more identical or different heteroatoms chosen from an oxygen or sulfur atom or ammonium —N$^+$(R$_a$)(R$_b$)—, —C(O)—, —C(S)— or a combination thereof, wherein R, R$_a$ and R$_b$ are independently chosen from hydrogen atoms or alkyl groups;

wherein R'$_1$, R"$_1$ and R"$_2$, may optionally be substituted with at least one hydroxyl, hydroxycarbonyl or carboxyl, $(C_1-C_6)$alkoxycarbonyl, alkyl$(C_1-C_6)$carbonyloxy, carbamoyloxy, (di)$(C_1-C_6)$(alkyl)silyl or tri$(C_1-C_5)$alkylsilyl group;

R' and R" are independently chosen from xl) $(C_1-C_5)$alkyl optionally substituted with one or more radicals chosen from hydroxyl radicals, xli) $(C_1-C_5)$alkoxycarbonyl, xlii) hydroxyl, xliii) halogen, xliv) $(C_1-C_5)$alkoxy, xlv) (poly)hydroxy$(C_1-C_5)$alkoxy, xlvi) (di)$(C_1-C_5)$(alkyl)amino, xlvii) nitro, xlviii) acylamino (—N(R)—C(O)R') with R chosen from a hydrogen atom or a (hydroxy)$(C_1-C_5)$alkyl radical, xlix) carbamoyl ($(R)_2N$—C(O)—) with R as defined for ix), l) carboxylic acid or ester, (—O—C(O)R') or (—C(O)OR' with R' as defined for ix) the carboxylic radical optionally in acid or salified form, li) alkylsulfonylamino (R'S(O)$_2$—N(R)—) or aminosulfonyl (($(R)_2N$—S(O)$_2$—) with R as defined for ix), lii) (poly)haloalkyl;

or alternatively when p is greater than or equal to 2, two groups R' or R" borne by two contiguous carbon atoms together form a (hetero)cycle or a (hetero)aryl;

R'''$_1$, R'''$_2$, R'''$_3$ and R'''$_4$ independently chosen from vii) linear or branched $(C_1-C_{20})$alkyl;

viii) $(C_2-C_{20})$alkenyl;

the alkyl or alkenyl group of the groups of i) and ii) optionally substituted and/or interrupted with one or more identical or different heteroatoms chosen from an oxygen or sulfur atom, the amino —N(R)—, ammonium —N$^+$(R$_a$)(R$_b$)—, —C(O)—, —C(S)— group or a combination thereof, with R, R$_a$ and R$_b$ independently chosen from hydrogen atoms or alkyl groups;

p is equal to 0, 1, 2, 3 or 4;

L represents a linear or branched, saturated or unsaturated divalent $C_1-C_{30}$ hydrocarbon-based chain, optionally interrupted and/or optionally terminated at one or both of its ends with one or more divalent groups or combinations thereof chosen from:

—N(R$_a$)—; —N$^+$(R$_a$)(R$_b$)—, Q$^-$; —O—, —S—; —S(O)—, —S(O)$_2$—, —C(S)— and —C(S)— with R$_a$ and R$_b$ independently chosen from hydrogen atoms and a $C_1-C_4$ alkyl, hydroxy$(C_1-C_8)$alkyl or amino$(C_1-C_8)$alkyl radicals and Q$^-$ represents an organic or mineral anionic counterion;

an aromatic or non-aromatic, saturated or unsaturated, fused or non-fused, cationic or non-cationic (hetero)cyclic radical optionally comprising one or more identical or different, optionally substituted heteroatoms;

wherein:

when the dyes of formula (Ia) are such that R$_1$, R$_2$, R$_3$ and R$_4$ are independently chosen from i) linear or branched $(C_1-C_{20})$alkyl; ii) $(C_2-C_{20})$alkenyl; the alkyl or alkenyl group of the groups of i) and ii) optionally interrupted with one or more identical or different heteroatoms chosen from an oxygen or sulfur atom or the amino —N(R)— group, then at least one of the said radicals R$_1$, R$_2$, R$_3$ and R$_4$ is substituted with at least one hydroxyl, hydroxycarbonyl or carboxyl, $(C_1-C_6)$alkoxycarbonyl, $(C_1-C_6)$alkylcarbonyloxy, carbamoyloxy, (di)$(C_1-C_6)$(alkyl)silyl or tri$(C_1-C_5)$alkylsilyl group;

when p is equal to 2, 3 or 4, then the groups R' are identical or different and R" are identical or different;

when the anionic part of the anionic direct dye or of the anionic optical brightener contains a sulfonate group or a carboxylate group, then m=n=1; and when the anionic part of the anionic direct dye or of the anionic optical brightener contains anionic groups other than the sulfonate or carboxylate group, it is combined with one or more organic or mineral cationic counterions or X$^+$ for affording the electrical neutrality of formula (Ia) or (Ib);

it being understood that the compound of formula (Ia) cannot represent compound (A), (B) or (C):

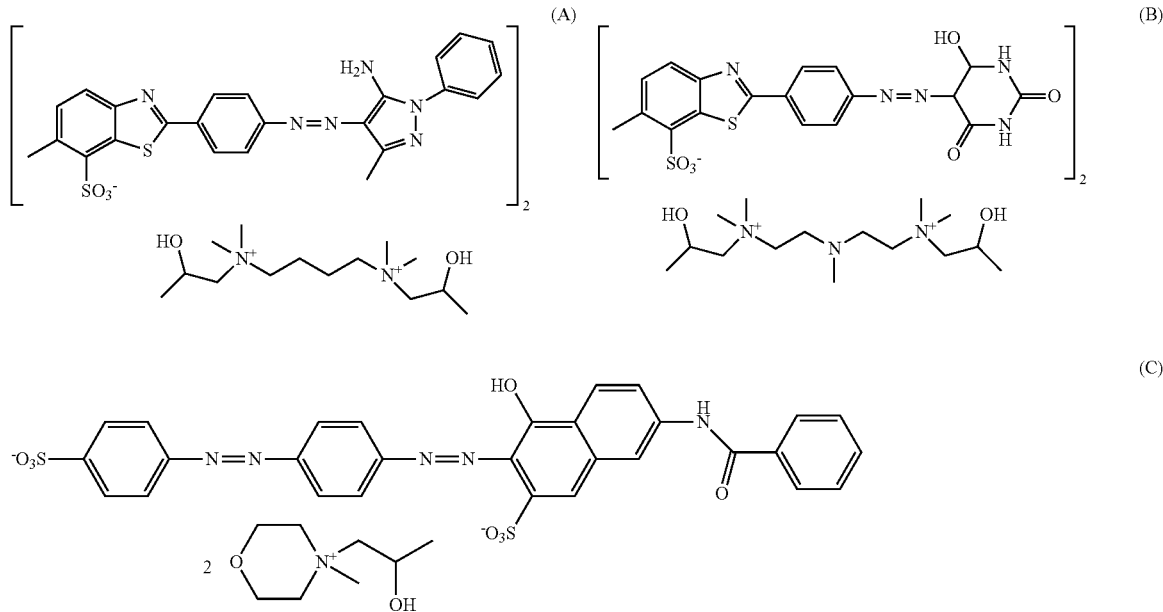

and Col$^{(-)}_m$ cannot represent:
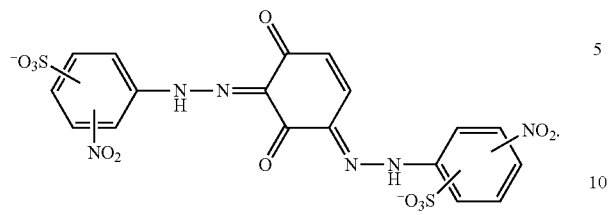
13. A cosmetic composition comprising the compound of claim 12.
* * * * *